US009631202B2

(12) United States Patent
Mason et al.

(10) Patent No.: US 9,631,202 B2
(45) Date of Patent: Apr. 25, 2017

(54) ELITE EVENT EE-GM3 AND METHODS AND KITS FOR IDENTIFYING SUCH EVENT IN BIOLOGICAL SAMPLES

(75) Inventors: Justin Thomas Mason, Granger, IA (US); Leslie James Lettow, Guthrie Center, IA (US); Mark Alan Eby, Adel, IA (US); William H. Eby, Panora, IA (US); Günter Welz, Wolfenbüttel (DE); Steven Verhaeghe, Grammene-Deinze (BE); Marc De Beuckeleer, Zwijnaarde (BE); Veerle Habex, Gullegem (BE); Jean-Marc Ferrulo, Soucy (FR)

(73) Assignees: M.S. TECHNOLOGIES LLC, West Point, IA (US); BAYER CROPSCIENCE N.V., Diegem (BE)

(*) Notice: Subject to any disclaimer, the term of this patent is extended or adjusted under 35 U.S.C. 154(b) by 1277 days.

(21) Appl. No.: 13/511,629

(22) PCT Filed: Nov. 23, 2010

(86) PCT No.: PCT/US2010/057869
§ 371 (c)(1),
(2), (4) Date: Aug. 7, 2012

(87) PCT Pub. No.: WO2011/063411
PCT Pub. Date: May 26, 2011

(65) Prior Publication Data
US 2012/0304330 A1 Nov. 29, 2012

Related U.S. Application Data

(60) Provisional application No. 61/263,690, filed on Nov. 23, 2009, provisional application No. 61/367,227, filed on Jul. 23, 2010.

(30) Foreign Application Priority Data

Nov. 23, 2009 (EP) .................... 09014564

(51) Int. Cl.
*C12Q 1/68* (2006.01)
*C12N 15/82* (2006.01)

(52) U.S. Cl.
CPC ..... *C12N 15/8274* (2013.01); *C12N 15/8275* (2013.01); *C12Q 1/6895* (2013.01); *C12Q 2600/13* (2013.01)

(58) Field of Classification Search
USPC ............................. 435/6.12, 91.2; 536/24.33
See application file for complete search history.

(56) References Cited

U.S. PATENT DOCUMENTS

| 5,510,471 A | 4/1996 | Lebrun et al. |
| 5,985,557 A | 11/1999 | Prudent et al. |
| 6,001,567 A | 12/1999 | Brow et al. |
| 6,245,968 B1 | 6/2001 | Boudec et al. |
| 6,313,282 B1* | 11/2001 | Atanassova et al. ........ 536/24.1 |
| 6,376,754 B1 | 4/2002 | Schillinger et al. |
| 6,566,587 B1 | 5/2003 | Lebrun et al. |
| 7,250,561 B1 | 7/2007 | Pallett et al. |
| 7,304,209 B2 | 12/2007 | Zink et al. |
| 8,592,650 B2 | 11/2013 | Mason et al. |
| 8,642,748 B2 | 2/2014 | Mason et al. |
| 2002/0100076 A1 | 7/2002 | Garcon et al. |
| 2002/0112260 A1 | 8/2002 | Schillinger et al. |
| 2003/0233675 A1 | 12/2003 | Cao et al. |
| 2004/0214272 A1 | 10/2004 | La Rosa et al. |
| 2006/0135758 A1 | 6/2006 | Wu |
| 2006/0282915 A1 | 12/2006 | Malven et al. |
| 2007/0061916 A1 | 3/2007 | Kovalic et al. |
| 2007/0083334 A1 | 4/2007 | Mintz et al. |
| 2007/0118921 A1 | 5/2007 | Boukharov et al. |
| 2008/0028481 A1 | 1/2008 | Pallett et al. |
| 2008/0163392 A1 | 7/2008 | Zink et al. |
| 2008/0196127 A1 | 8/2008 | De Beuckeleer et al. |
| 2008/0282429 A1* | 11/2008 | Tissot ................ C12N 15/8214 800/287 |
| 2008/0312082 A1 | 12/2008 | Kinney et al. |
| 2008/0320616 A1* | 12/2008 | De Beuckeleer ............. 800/312 |
| 2009/0013431 A1 | 1/2009 | Van Thournout et al. |
| 2009/0036308 A1 | 2/2009 | Guida, Jr. et al. |
| 2009/0093620 A1 | 4/2009 | Kovalic et al. |
| 2009/0130071 A1 | 5/2009 | Gao et al. |
| 2009/0191188 A1 | 7/2009 | Krieg et al. |

(Continued)

FOREIGN PATENT DOCUMENTS

| AU | 734878 | 6/2001 |
| DE | WO 2006/108674 | 10/2006 |

(Continued)

OTHER PUBLICATIONS

Privalle et al, Development of an Agricultural Biotechnology Crop Product: Testing from Discovery to Commercialization, J. of Agric. and Food Chem. (2012) 10179-10187.
Puchta et al, From centiMorgans to Base Pairs: Homologous Recombination in Plants, Trends in Plant Sci. (1996) 1:340-348.
Devine, M, Why are There Not More Herbicide-Tolerant Crops? Pest Mngmt. Sci. (2005) 61:312-317.
Japanese Office Action mailed Feb. 3, 2015, Patent Application No. 2012-541170.
Office Action for Mexican Patent Application No. MX/a/2012/005937 dated Feb. 21, 2014 (7 pages).
AIPO Patent Examination Report No. 1 for AU Patent Application No. 2010321584 mailed May 30, 2014.
Carrington and Freed, Journal of Virology, vol. 64, pp. 1590-1597 (1990).
Chaboute, et al., Plant Molecular Biology, vol. 8, pp. 179-191 (1987).
Chaubet, et al., Journal of Molecular Biology, vol. 225, pp. 569-574 (1992).
Depicker, et al., Journal of Molecular and Applied Genetics, vol. 1, pp. 561-573 (1982).

(Continued)

*Primary Examiner* — Aaron Priest
(74) *Attorney, Agent, or Firm* — Arent Fox LLP

(57) ABSTRACT

The invention provides specific transgenic soybean plants, plant material and seeds, characterized in that these products harbor a specific herbicide tolerance transformation event at a specific location in the soybean genome. Tools are also provided which allow rapid and unequivocal identification of the event in biological samples.

62 Claims, 3 Drawing Sheets

(56) References Cited

U.S. PATENT DOCUMENTS

2011/0239321 A1 9/2011 Mason et al.
2012/0304331 A1 11/2012 Mason et al.

FOREIGN PATENT DOCUMENTS

| DE | WO 2006/108675 | 10/2006 |
|---|---|---|
| EP | 1 186 666 | 3/2002 |
| EP | 1186666 | 3/2002 |
| FR | 2 770 854 | 5/1999 |
| WO | WO 97/04103 | 2/1997 |
| WO | WO 97/43618 | 11/1997 |
| WO | WO 98/02562 | 1/1998 |
| WO | WO 98-02562 | 1/1998 |
| WO | WO 01/88089 | 11/2001 |
| WO | WO 2005/098015 A2 | 10/2005 |
| WO | WO 2006/130436 | 12/2006 |
| WO | WO 2007-017186 | 2/2007 |
| WO | WO 2007/017186 | 2/2007 |
| WO | WO 2008/002872 | 1/2008 |
| WO | WO 2008/054747 | 5/2008 |
| WO | WO 2008-141154 | 11/2008 |
| WO | WO 2010/080829 | 7/2010 |
| WO | WO 2011/063413 | 5/2011 |

OTHER PUBLICATIONS

Edwards, et al., Nucleic Acid Research, vol. 19, p. 1349 (1991).
Elmore, et al., Agronomy Journal, vol. 93, pp. 408-412 (2001).
Hohe, et al. (2003) Plant Cell Rep. 21: 1135-1142.
Kaskey, Bloomberg Web Page downloaded from the Internet on Nov. 17, 2009 at: www.bloomberg.com/apps/news?pid=newsarchive&sid=ad4L0hH9MKwE.
Nelson, et al., Agronomy Journal, vol. 94, pp. 1270-1281 (2002).
Nickell, et al., Crop Sci., vol. 1365, p. 30 (1990).
Onishi, et al., "Development of a Multiplex Polymerase Chain Reaction Method for Simultaneous Detection of Eight Events of Genetically Modified Maize," Journal Agricultural and Food Chemistry, vol. 53, pp. 9713-9721 (2005).
Wilbur and Lipman, Proc. Nat. Acad. Sci. USA, vol. 80, p. 726 (1983).
USDA-APHIS Petition 06-354-01p (2006).
USDA-APHIS Petition 06-271-01p (2006).
USDA-APHIS Petition 06-178-01p (2006).
USDA-APHIS Petition 98-238-01p (1998).
USDA-APHIS Petition 98-014-01p (1998).
USDA-APHIS Petition 97-008-01p (1997).
USDA-APHIS Petition 96-068-01p (1996).
USDA-APHIS Petition 93-258-01p (1993).
International Search Report for International Application No. PCT/US2010/57886, mailed Jun. 15, 2011.
Written Opinion for International Application No. PCT/US2010/57886, mailed Jun. 15, 2011.
International Preliminary Report on Patentability for International Application No. PCT/US2010/57886, mailed Jun. 7, 2012.
International Preliminary Report on Patentability and Written Opinion for International Application No. PCT/US2010/057869, mailed Jun. 7, 2012.
Herouet-Guicheney, et al. (2009) Regulatory Toxicology and Pharmacology 54(2):143-153.
Green, Jerry M., "Evolution of Glyphosate-Resistant Crop Technology," Weed Science, vol. 57, pp. 108-117, 2009.
Supplemental European Search Report for International Patent Application No. PCT/US2010/057869, dated Apr. 25, 2013.
Canadian Office Action dated Oct. 31, 2016 issued in Canadian Patent Application No. 2,781,557.
GenBank Accession No. AB006705.2, "Aradiposis thaliana genomic DNA, chromosome 5, P1 clone:MTH12," https://www.ncbi.nlm.nih.gov/nuccore/AB006705, last updated date Feb. 14, 2004 (39 pages).
GenBank Accession No. AR177916.1, "Sequence 1 from U.S. Pat. No. 6,313,282," https://www.ncbi.nlm.nih.gov/nuccore/AR177916, last updated date Dec. 17, 2001 (2 pages).
GenBank Accession No. CS226408.1, "Sequence 191 from Patent WO2005098015," https://www.ncbi.nlm.nih.gov/nuccore/CS226408, last updated date Jul. 14, 2006 (3 pages).
GenBank Accession No. DD031069.1, "Herbicide-tolerant plants through bypassing metabolic pathway," https://www.ncbi.nlm.nih.gov/nuccore/DD031069, last updated date Nov. 4, 2005 (5 pages).
GenBank Accession No. EA327079.1, "Sequence 15 from U.S. Pat. No. 7,304,209," https://www.ncbi.nlm.nih.gov/nuccore/EA327079, last updated date Dec. 14, 2007 (3 pages).
GenBank Accession No. EA327083.1, "Sequence 1 from U.S. Pat. No. 7,304,209," https://www.ncbi.nlm.nih.gov/nuccore/EA327083, last updated date Dec. 14, 2007 (5 pages).

* cited by examiner

ELITE EVENT EE-GM3 AND METHODS AND KITS FOR IDENTIFYING SUCH EVENT IN BIOLOGICAL SAMPLES

CROSS-REFERENCE TO RELATED APPLICATIONS

This application is the national phase application of PCT/US2010/057869, filed Nov. 23, 2010, which claims the benefit of EP 09014564.0, filed Nov. 23, 2009, U.S. Provisional Application 61/263,690, filed Nov. 23, 2009 and U.S. Provisional Application 61/367,227 filed Jul. 23, 2010, the contents of each are hereby incorporated by reference in their entireties.

FIELD OF THE INVENTION

This invention relates to transgenic soybean plants, plant material and seeds, characterized by harboring a specific transformation event, particularly by the presence of genes encoding proteins that confer herbicide tolerance, at a specific location in the soybean genome. The soybean plants of the invention combine the herbicide tolerance phenotype with an agronomic performance, genetic stability and functionality in different genetic backgrounds equivalent to the non-transformed soybean line in the absence of herbicide(s). This invention further provides methods and kits for identifying the presence of plant material comprising specifically transformation event EE-GM3 in biological samples.

BACKGROUND OF THE INVENTION

The phenotypic expression of a transgene in a plant is determined both by the structure of the gene or genes itself and by its or their location in the plant genome. At the same time the presence of the transgenes or "foreign DNA" at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary. Specific tools for use in the identification of elite event EE-GM3 in biological samples are described herein.

In this invention, EE-GM3 has been identified as an elite event from a population of transgenic soybean plants in the development of herbicide tolerant soybean (*Glycine max*) comprising a gene coding for glyphosate tolerance combined with a gene conferring tolerance to 4-hydroxy phenylpyruvate dioxygenase (HPPD) inhibitors, each under control of a plant-expressible promoter.

Soybean plants comprising a herbicide tolerance gene have been disclosed in the art. However, none of the prior art disclosures teach or suggest the present invention.

It is known in the art that getting a commercial herbicide tolerant elite transformation event in soybean plants with acceptable agronomic performance, with no yield drag, and providing sufficient herbicide tolerance, certainly to 2 different classes of herbicides, is by no means straightforward.

Indeed, it has been reported that the first soybean event (event 40-3-2) released on the market with herbicide tolerance, had a significant yield drag compared to (near-) isogenic lines (Elmore et al. (2001) Agron. J. 93:408-412).

Also, Optimum GAT™ soybeans were made to combine tolerance to glyphosate with tolerance to ALS herbicides, but it has been reported by their developer that these soybeans were not meeting the standards for glyphosate tolerance by itself (without combination with another glyphosate tolerance soybean event such as event 40-3-2 (see, e.g., www.bloomberg.com/apps/news?pid=newsarchive&sid=ad4L0hH9MKWE)).

SUMMARY OF THE PREFERRED EMBODIMENTS OF THE INVENTION

The present invention relates to a transgenic soybean plant, or seed, cells or tissues thereof, comprising, stably integrated into its genome, an expression cassette which comprises a herbicide tolerance gene comprising the coding sequence of the 2mEPSPS gene and another herbicide tolerance gene comprising the coding sequence of HPPD-Pf W336 (both as described in Example 1.1 herein and as represented in SEQ ID No 1), which is tolerant to glyphosate and an HPPD inhibitor herbicide such as isoxaflutole, and, in the absence of herbicide(s), has an agronomic performance which is substantially equivalent to the non-transgenic isogenic line. After application of one or more herbicides to which tolerance is provided, the plant will have a superior agronomic phenotype compared to a non-transgenic plant.

According to the present invention the soybean plant or seed, cells or tissues thereof comprise elite event EE-GM3.

More specifically, the present invention relates to a transgenic soybean plant, seed, cells or tissues thereof, the genomic DNA of which is characterized by the fact that, when analyzed in a PCR Identification Protocol as described herein, using two primers directed to the 5' or 3' flanking region of EE-GM3 and the foreign DNA comprising herbicide tolerance genes, respectively, yields a fragment which is specific for EE-GM3. The primers may be directed against the 5' flanking region within SEQ ID NO: 2 and the foreign DNA comprising herbicide tolerance genes, respectively. The primers may also be directed against the 3' flanking region within SEQ ID NO: 3 and the foreign DNA comprising herbicide tolerance genes, respectively, such as the primers comprising or consisting (essentially) of the nucleotide sequence of SEQ ID NO: 5 and SEQ ID NO: 4 or SEQ ID No.: 7 respectively, and yield a DNA fragment of between 100 and 800 bp, such as a fragment of about 263 bp or 706 bp.

Reference seed comprising the elite event of the invention has been deposited at the NCIMB under accession number NCIMB 41659. One embodiment of the invention is the seed comprising elite event EE-GM3 deposited as accession number NCIMB 41659, which will grow into a soybean plant tolerant to herbicides, particularly tolerant to glyphosate and/or HPPD inhibitors such as isoxaflutole. The seed of NCIMB deposit number NCIMB 41659, is a seed lot consisting of at least about 95% transgenic seeds homozygous for the transferred DNA, comprising the elite event of the invention, which will grow into herbicide tolerant plants, whereby the plants are glyphosate and/or isoxaflutole tolerant. The seed or progeny seed obtainable or obtained from the deposited seed (e.g., following crossing with other soybean plants with a different genetic background) can be sown and the growing plants can be treated with glyphosate or isoxaflutole as described herein to obtain 100% glyphosate or isoxaflutole tolerant plants, comprising the elite event of the invention. The invention further relates to cells, tissues, progeny, and descendants from a plant comprising the elite event of the invention grown from the seed deposited at the NCIMB having accession number NCIMB 41659. The invention further relates to plants obtainable from (such as by propagation of and/or breeding with) a soybean plant comprising the elite event of the invention (such as a plant grown from the seed deposited at the NCIMB having accession number NCIMB 41659). The invention also relates to soybean plants comprising elite event EE-GM3.

The invention further relates to a method for identifying a transgenic plant, or cells or tissues thereof, comprising elite event EE-GM3 which method is based on identifying the presence of characterizing DNA sequences or amino acids encoded by such DNA sequences in the transgenic plant, cells or tissues. According to a preferred embodiment of the invention, such characterizing DNA sequences are sequences of 15 bp or at least 15 bp, preferably 20 bp or at least 20 bp, most preferably 30 bp or more which comprise the insertion site of the event, i.e. both a part of the inserted foreign DNA comprising herbicide tolerance genes and a part of the soybean genome (either the 5' or 3' flanking region) contiguous therewith, allowing specific identification of the elite event. The invention also relates to plants comprising the event EE-GM3 as identified herein.

The present invention further relates to methods for identifying elite event EE-GM3 in biological samples, which methods are based on primers or probes which specifically recognize the 5' and/or 3' flanking sequence of the foreign DNA comprising the herbicide tolerance genes in EE-GM3.

More specifically, the invention relates to a method comprising of amplifying a sequence of a nucleic acid present in biological samples, using a polymerase chain reaction with at least two primers, one of which recognizes the 5' or 3' flanking region of foreign DNA comprising the herbicide tolerance genes in EE-GM3, the other which recognizes a sequence within the foreign DNA comprising the herbicide tolerance genes, preferably to obtain a DNA fragment of between 100 and 800 bp. The primers may recognize a sequence within the 5' flanking region of EE-GM3 (SEQ ID No. 2, from position 1 to position 1451) or within the 3' flanking region of EE-GM3 (complement of SEQ ID No 3 from position 241 to position 1408) and a sequence within the foreign DNA comprising herbicide tolerance genes (complement of SEQ ID No 2 from position 1452 to 1843 or SEQ ID No 3 from position 1 to position 240), respectively. The primer recognizing the 3' flanking region may comprise the nucleotide sequence of SEQ ID No. 5 and the primer recognizing a sequence within the foreign DNA comprising herbicide tolerance genes may comprise the nucleotide sequence of SEQ ID No. 4 or SEQ ID No. 7 described herein. This invention also relates to the specific primers and the specific DNA amplified using such primers, as described herein.

The present invention more specifically relates to a method for identifying elite event EE-GM3 in biological samples, which method comprises amplifying a sequence of a nucleic acid present in a biological sample, using a polymerase chain reaction with two primers comprising or consisting (essentially) of the nucleotide sequence of SEQ ID No. 4 and SEQ ID No. 5 respectively, to obtain a DNA fragment of about 263 bp or with two primers comprising or consisting (essentially) of the nucleotide sequence of SEQ ID No. 5 and SEQ ID No. 7 respectively, to obtain a DNA fragment of about 706 bp. Also plants comprising the thus-identified elite event EE-GM3 are included in this invention.

The present invention further relates to the specific flanking sequences of EE-GM3 described herein, which can be used to develop specific identification methods for EE-GM3 in biological samples. Such specific flanking sequences may also be used as reference control material in identification assays. More particularly, the invention relates to the 5' and/or 3' flanking regions of EE-GM3 which can be used for the development of specific primers and probes as further described herein. Also suitable as reference material are nucleic acid molecules, preferably of about 150-850 bp, comprising the sequence which can be amplified by primers comprising or consisting (essentially) of the nucleotide sequence of SEQ ID No. 7 and SEQ ID No. 5 or of SEQ ID No. 4 and SEQ ID No. 5.

The invention further relates to identification methods for the presence of EE-GM3 in biological samples based on the use of such specific primers or probes. Primers may comprise, consist or consist essentially of a nucleotide sequence of 17 to about 200 consecutive nucleotides selected from the nucleotide sequence of SEQ ID No 2 from nucleotide 1 to nucleotide 1451 or the complement of the nucleotide sequence of SEQ ID 3 from nucleotide 241 to nucleotide 1408, combined with primers comprising, consisting, or consisting essentially of a nucleotide sequence of 17 to about 200 consecutive nucleotides selected from the nucleotide sequence of SEQ ID No 2, such as a nucleotide sequence of 17 to about 200 consecutive nucleotides selected from the complement of the nucleotide sequence of SEQ ID No 2 from nucleotide 1452 to nucleotide 1843 or the nucleotide sequence of SEQ ID No 3 from nucleotide 1 to nucleotide 240. Primers may also comprise these nucleotide sequences located at their extreme 3' end, and further comprise unrelated sequences or sequences derived from the mentioned nucleotide sequences, but comprising mismatches.

The invention further relates to kits for identifying elite event EE-GM3 in biological samples, said kits comprising at least one primer or probe which specifically recognizes the 5' or 3' flanking region of the foreign DNA comprising herbicide tolerance genes in EE-GM3.

The kit of the invention may comprise, in addition to a primer which specifically recognizes the 5' or 3' flanking region of EE-GM3, a second primer which specifically recognizes a sequence within the foreign DNA comprising herbicide tolerance genes of EE-GM3, for use in a PCR Identification Protocol. The kits of the invention may comprise at least two specific primers, one of which recognizes a sequence within the 5' flanking region of EE-GM3, and the other which recognizes a sequence within the foreign DNA comprising herbicide tolerance genes. The primer recognizing the 3' flanking region may comprise the nucleotide sequence of SEQ ID No. 5 and the primer recognizing the transgenes or foreign DNA comprising herbicide tolerance genes may comprise the nucleotide sequence of SEQ ID Nos. 4 or 7, or any other primer or primer combination as described herein.

The invention further relates to a kit for identifying elite event EE-GM3 in biological samples, said kit comprising the PCR primers comprising or consisting (essentially) of the nucleotide sequence of SEQ ID No. 5 and SEQ ID No. 4 for use in the EE-GM3 PCR Identification Protocol described herein.

The invention also relates to a kit for identifying elite event EE-GM3 in biological samples, which kit comprises a specific probe comprising or consisting (essentially) of a sequence which corresponds (or is complementary to) a sequence having between 80% and 100% sequence identity with a specific region of EE-GM3. Preferably, the sequence of the probe corresponds to a specific region comprising part of the 5' or 3' flanking region of EE-GM3. Most preferably the specific probe comprises or consists (essentially) of (or is complementary to) a sequence having between 80% and 100% sequence identity to the sequence between nucleotide 1431 to 1472 of SEQ ID No 2 or a sequence having between 80% and 100% sequence identity to the sequence between nucleotide 220 to 260 of ID No. 3.

According to another aspect of the invention, DNA sequences are disclosed comprising the insertion site of the event and sufficient length of polynucleotides of both the soybean genomic DNA and the foreign DNA comprising herbicide tolerance genes (transgene), so as to be useful as primer or probe for the detection of EE-GM3, and to characterize plants comprising event EE-GM3. Such sequences may comprise at least 9 nucleotides of the soybean genomic DNA and a similar number of nucleotides of the foreign DNA comprising the herbicide tolerance genes of EE-GM3, at each side of the junction site respectively. Most preferably, such DNA sequences comprise at least 9 nucleotides of the soybean genomic DNA and a similar number of nucleotides of the foreign DNA comprising herbicide tolerance genes contiguous with the insertion site in SEQ ID NO: 2 or SEQ ID NO: 3. In one aspect of the invention, soybean plants are provided comprising such specific DNA sequences.

The methods and kits encompassed by the present invention can be used for different purposes such as, but not limited to the following: to identify the presence or determine the (lower) threshold of EE-GM3 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e. percentage pure material) of plant material comprising EE-GM3.

The invention further relates to the 5' and/or 3' flanking regions of EE-GM3 as well as to the specific primers and probes developed from the 5' and/or 3' flanking sequences of EE-GM3.

The invention also relates to genomic DNA obtained from plants comprising elite event EE-GM3. Such genomic DNA may be used as reference control material in the identification assays herein described.

Also provided herein is a transgenic herbicide tolerant soybean plant, or cells, parts, seeds or progeny thereof, each comprising at least one elite event, said elite event comprises a foreign DNA comprising:
  i) a first chimeric gene which comprises a modified epsps gene from *Zea mays* encoding a glyphosate tolerant EPSPS enzyme under the control of a plant-expressible promoter, and
  ii) a second chimeric gene which comprises a modified hppd gene from *Pseudomonas fluorescens* encoding an HPPD inhibitor herbicide tolerant enzyme under the control of a plant-expressible promoter.

In one embodiment, said elite event comprises nucleotides 1 to 1451 of SEQ ID No 2 immediately upstream of and contiguous with said foreign DNA and nucleotides 241 to 1408 of SEQ ID No 3 immediately downstream of and contiguous with said foreign DNA.

In a further embodiment, said elite event is obtainable by breeding with a soybean plant grown from reference seed comprising said event having been deposited at the NCIMB under deposit number NCIMB 41659.

In another embodiment, the genomic DNA of said soybean plant, or cells, parts, seeds or progeny thereof when analyzed using the elite event identification protocol for said elite event with two primers comprising the nucleotide sequence of SEQ ID No 4 and SEQ ID No 5 respectively, yields a DNA fragment of (about) 263 bp.

Also provided herein is a method for identifying a transgenic soybean plant, or cells, parts, seed or progeny thereof tolerant to glyphosate and/or an HPPD inhibitor herbicide, such as isoxaflutole, in biological samples, said method comprising amplifying a DNA fragment of between 100 and 500 bp from a nucleic acid present in biological samples using a polymerase chain reaction with at least two primers, one of said primers recognizing the 5' flanking region of the elite event specified above, said 5' flanking region comprising the nucleotide sequence of SEQ ID No 2 from nucleotide 1 to nucleotide 1451, or the 3' flanking region of said elite event, said 3' flanking region comprising or the nucleotide sequence of the complement of SEQ ID No 3 from nucleotide 241 to nucleotide 1408, the other primer of said primers recognizing a sequence within the foreign DNA comprising the nucleotide sequence of the complement of SEQ ID No 2 from nucleotide 1452 to nucleotide 1843 or the nucleotide sequence of SEQ ID No 3 from nucleotide 1 to nucleotide 240.

Also provided herein is a kit for identifying a transgenic soybean plant, or cells, parts, seed or progeny thereof tolerant to glyphosate and/or an HPPD inhibitor herbicide, such as isoxaflutole, in biological samples, said kit comprising one primer recognizing the 5' flanking region of the elite event specified above, said 5' flanking region comprising the nucleotide sequence of SEQ ID No 2 from nucleotide 1 to nucleotide 1451, or one primer recognizing the 3' flanking region of said elite event, said 3' flanking region comprising the nucleotide sequence of the complement of SEQ ID No 3 from nucleotide 241 to nucleotide 1408, and one primer recognizing a sequence within the foreign DNA, said foreign DNA comprising the nucleotide sequence of the complement of SEQ ID No. 2 from nucleotide 1452 to nucleotide 1843 or the nucleotide sequence of SEQ ID No 3 from nucleotide 1 to nucleotide 240.

In one embodiment of the invention, the foreign DNA of elite event EE-0M3, as used herein, comprises the nucleotide sequence of SEQ ID No 11 from nucleotide position 1452 to nucleotide position 16638 or its complement, or comprises a sequence with at least 95, 98, 99, or 99.5% sequence identity to the nucleotide sequence of SEQ ID No 11 from nucleotide position 1452 to nucleotide position 16638 or its complement.

Also provided herein is a soybean plant, plant cell, tissue, or seed, comprising in their genome a nucleic acid molecule comprising a nucleotide sequence with at least 97, 98, or at least 99% sequence identity to the nucleotide sequence of SEQ ID No. 11 from nucleotide position 1452 to nucleotide position 16638 or the complement thereof, or a nucleotide sequence with at least 97, 98, or at least 99% sequence identity to SEQ ID No. 11 or the complement thereof.

One embodiment of this invention provides a soybean plant, plant cell, tissue, or seed, comprising in their genome a nucleic acid molecule hybridizing to the nucleotide sequence of SEQ ID No 1 or the complement thereof, or hybridizing to the nucleotide sequence of SEQ ID No. 11 from nucleotide position 1452 to nucleotide position 16638 or the complement thereof, or hybridizing to the nucleotide sequence of SEQ ID No. 11 or the complement thereof.

Also provided herein is an isolated nucleic acid molecule comprising a nucleotide sequence with at least 99% sequence identity to the nucleotide sequence of SEQ ID No. 11 from nucleotide position 1452 to nucleotide position 16638 or the complement thereof, or a nucleotide sequence with at least 99% sequence identity to SEQ ID No. 11 or the complement thereof, or an isolated nucleic acid molecule comprising a nucleotide sequence hybridizing to the nucleotide sequence of SEQ ID No. 11 from nucleotide position 1452 to nucleotide position 16638 or the complement thereof, or hybridizing to the nucleotide sequence of SEQ ID No. 11 or the complement thereof.

BRIEF DESCRIPTION OF THE DRAWINGS

The following Examples, not intended to limit the invention to specific embodiments described, may be understood in conjunction with the accompanying Figures, incorporated herein by reference, in which.

DETAILED DESCRIPTION OF THE PREFERRED EMBODIMENTS OF THE INVENTION

Figure 1:
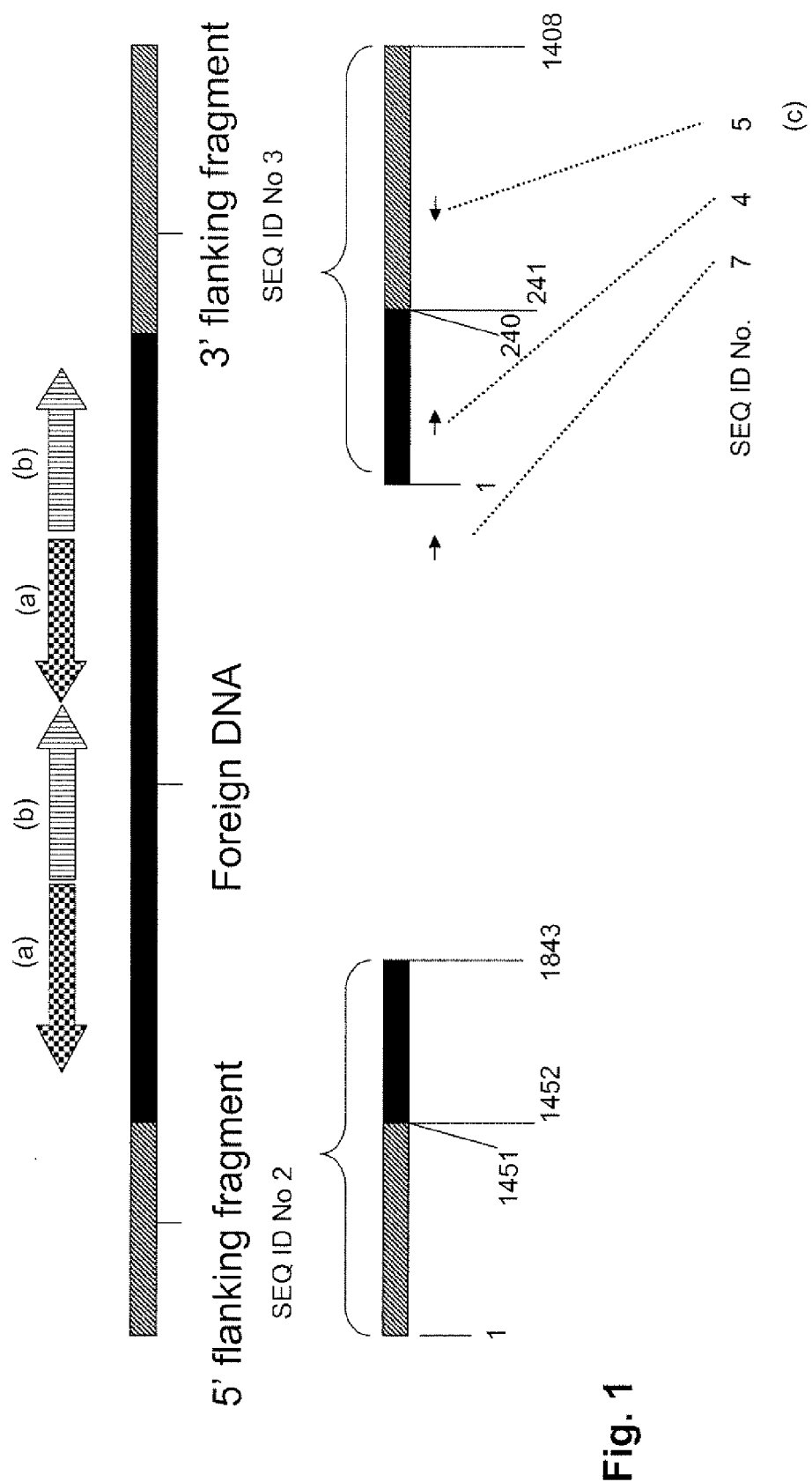
FIG. 1: Schematic representation of the relationship between the cited nucleotide sequences and primers. black bar: foreign DNA; hatched bar: DNA of plant origin; checkered arrow (a): chimeric HPPD PfW366-encoding gene (see Table 1 for composition of the chimeric gene); hatched arrow (b): chimeric 2mEPSPS-encoding gene (see Table 1 for composition of the chimeric gene); black arrows: oligonucleotide primers, the figures under the bars represent nucleotide positions; (c) refers to complement of the indicated nucleotide sequence; Note: the scheme is not drawn to scale.

The incorporation of a recombinant DNA molecule in the plant genome typically results from transformation of a cell or tissue. The particular site of incorporation is usually due to random integration.

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". The transgenes of EE-GM3 are the glyphosate and HPPD inhibitor herbicide tolerance genes. "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the region of the plant genome referred to as "pre-insertion plant DNA" can be associated with a deletion of plant DNA, referred to as "target site deletion". A "flanking region" or "flanking sequence" as used herein refers to a sequence of at least 20 bp, preferably at least 50 bp, and up to 5000 bp of DNA different from the introduced DNA, preferably DNA from the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed.

An "isolated nucleic acid (sequence)" or "isolated DNA (sequence)", as used herein, refers to a nucleic acid or DNA (sequence) which is no longer in the natural environment it was isolated from, e.g., the nucleic acid sequence in another bacterial host or in a plant genome, or a nucleic acid or DNA fused to DNA or nucleic acid from another origin, such as when contained in a chimeric gene under the control of a plant-expressible promoter.

An event is defined as a (artificial) genetic locus that, as a result of genetic engineering, carries a foreign DNA or transgene comprising at least one copy of a gene of interest or of the genes of interest. The typical allelic states of an event are the presence or absence of the foreign DNA. An event is characterized phenotypically by the expression of the transgene. At the genetic level, an event is part of the genetic make-up of a plant. At the molecular level, an event can be characterized by the restriction map (e.g., as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique. An event is characterized by the foreign DNA and at least one of the flanking sequences.

An elite event, as used herein, is an event which is selected from a group of events, obtained by transformation with the same transforming DNA, based on the expression and stability of the transgene(s) and its compatibility with optimal agronomic characteristics of the plant comprising it. Thus the criteria for elite event selection are one or more, preferably two or more, advantageously all of the following:

a) that the presence of the foreign DNA does not compromise other desired characteristics of the plant, such as those relating to agronomic performance or commercial value;
b) that the event is characterized by a well defined molecular configuration which is stably inherited and for which appropriate tools for identity control can be developed;
c) that the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which meets the above-described criteria. A plant, plant material or progeny such as seeds can comprise one or more elite events in its genome.

The tools developed to identify an elite event or the plant or plant material comprising an elite event, or products which comprise plant material comprising the elite event, are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers", one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for the invention may be the following:
oligonucleotides ranging in length from 17 nt to about 200 nt, comprising a nucleotide sequence of at least 17 consecutive nucleotides, preferably 20 consecutive nucleotides, selected from the plant DNA in the 5' flanking sequence (SEQ ID No 2 from nucleotide 1 to nucleotide 1451) at their 3' end (primers recognizing 5' flanking sequences); or oligonucleotides ranging in length from 17 nt to about 200 nt, comprising a nucleotide sequence of at least 17 consecutive nucleotides, preferably 20 consecutive nucleotides, selected from the plant DNA in the 3' flanking sequence (complement of SEQ ID No 3 from nucleotide 241 to nucleotide 1408) at their 3' end (primers recognizing 3' flanking sequences); or
oligonucleotides ranging in length from 17 nt to about 200 nt, comprising a nucleotide sequence of at least 17 consecutive nucleotides, preferably 20 consecutive nucleotides, selected from the inserted DNA sequences (complement of SEQ ID No 2 from nucleotide 1452 to nucleotide 1843) at their 3' end (primers recognizing foreign DNA); or
oligonucleotides ranging in length from 17 nt to about 200 nt, comprising a nucleotide sequence of at least 17 consecutive nucleotides, preferably 20 consecutive nucleotides, selected from the inserted DNA sequences (SEQ ID No 3 from nucleotide 1 to nucleotide 240); or
suitable oligonucleotides ranging in length from 17 nt to about 200 nt, comprising a nucleotide sequence of at least 17 consecutive nucleotides, preferably 20 consecutive nucleotides, selected from the nucleotide sequence of the inserted DNA fragment or its complement (SEQ ID No 1 or SEQ ID No 11 from nucleotide position 1452 to 16638).

The primers may of course be longer than the mentioned 17 consecutive nucleotides, and may, e.g., be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may comprise or consist of a nucleotide sequence selected from the flanking sequences or foreign DNA, as appropriate, but may contain several (e.g., 1, 2, 5, or 10) mismatches. The 5' sequence of the primers may even entirely be a nucleotide sequence unrelated to the flanking sequences or foreign DNA, such as, e.g., a nucleotide sequence representing one or more restriction enzyme recognition sites. Such unrelated sequences or flanking DNA sequences with mismatches should preferably be not longer than 100, more preferably not longer than 50 or even 25 nucleotides.

Moreover, suitable primers may comprise or consist (essentially) of a nucleotide sequence at their 3' end spanning the joining region between the plant DNA derived sequences and the foreign DNA sequences (located at nucleotides 1451-1452 in SEQ ID No 2 and nucleotides 240-241 in SEQ ID No 3) provided the mentioned 3'-located 17 consecutive nucleotides are not derived exclusively from either the foreign DNA or plant-derived sequences in SEQ ID Nos 2 or 3.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides with their complementary nucleotide according to Chargaff's rules (A⇔T; G⇔C) and reading the sequence in the 5' to 3' direction, i.e., in opposite direction of the represented nucleotide sequence.

Examples of suitable primers are the oligonucleotide sequences of SEQ ID No 5 (3' flanking sequence recognizing primer), SEQ ID No 4 (foreign DNA recognizing primer for use with the 3' flanking sequence recognizing primers), or SEQ ID No 7 (foreign DNA recognizing primer for use with the 3' flanking sequence recognizing primers).

Other examples of suitable oligonucleotide primers comprise at their 3' end the following sequences or consist (essentially) of such sequences:

a. 5' flanking sequence recognizing primers:
   the nucleotide sequence of SEQ ID No 2 from nucleotide 264 to nucleotide 283
   the nucleotide sequence of SEQ ID No 2 from nucleotide 266 to nucleotide 285
   the nucleotide sequence of SEQ ID No 2 from nucleotide 1240 to nucleotide 1259
   the nucleotide sequence of SEQ ID No 2 from nucleotide 265 to nucleotide 285
   the nucleotide sequence of SEQ ID No 2 from nucleotide 265 to nucleotide 283
   the nucleotide sequence of SEQ ID No 2 from nucleotide 1239 to nucleotide 1259
   the nucleotide sequence of SEQ ID No 2 from nucleotide 1241 to nucleotide 1259
   the nucleotide sequence of SEQ ID No 2 from nucleotide 1244 to nucleotide 1263
   the nucleotide sequence of SEQ ID No 2 from nucleotide 1248 to nucleotide 1267
   the nucleotide sequence of SEQ ID No 2 from nucleotide 1250 to nucleotide 1269
   the nucleotide sequence of SEQ ID No 2 from nucleotide 262 to nucleotide 279
   the nucleotide sequence of SEQ ID No 2 from nucleotide 263 to nucleotide 279
   the nucleotide sequence of SEQ ID No 2 from nucleotide 264 to nucleotide 285
   the nucleotide sequence of SEQ ID No 2 from nucleotide 266 to nucleotide 283
   the nucleotide sequence of SEQ ID No 2 from nucleotide 1238 to nucleotide 1259
   the nucleotide sequence of SEQ ID No 2 from nucleotide 1242 to nucleotide 1259
   the nucleotide sequence of SEQ ID No 2 from nucleotide 1243 to nucleotide 1263
   the nucleotide sequence of SEQ ID No 2 from nucleotide 1245 to nucleotide 1263
   the nucleotide sequence of SEQ ID No 2 from nucleotide 1247 to nucleotide 1267
   the nucleotide sequence of SEQ ID No 2 from nucleotide 1249 to nucleotide 1269
   the nucleotide sequence of SEQ ID No 2 from nucleotide 1249 to nucleotide 1267
   the nucleotide sequence of SEQ ID No 2 from nucleotide 263 to nucleotide 285
   the nucleotide sequence of SEQ ID No 2 from nucleotide 267 to nucleotide 283
   the nucleotide sequence of SEQ ID No 2 from nucleotide 1242 to nucleotide 1263
   the nucleotide sequence of SEQ ID No 2 from nucleotide 1243 to nucleotide 1259
   the nucleotide sequence of SEQ ID No 2 from nucleotide 1246 to nucleotide 1267
   the nucleotide sequence of SEQ ID No 2 from nucleotide 1246 to nucleotide 1263
   the nucleotide sequence of SEQ ID No 2 from nucleotide 1248 to nucleotide 1269
   the nucleotide sequence of SEQ ID No 2 from nucleotide 1250 to nucleotide 1271
   the nucleotide sequence of SEQ ID No 2 from nucleotide 1250 to nucleotide 1267
   the nucleotide sequence of SEQ ID No 2 from nucleotide 1241 to nucleotide 1263
   the nucleotide sequence of SEQ ID No 2 from nucleotide 1245 to nucleotide 1267
   the nucleotide sequence of SEQ ID No 2 from nucleotide 1247 to nucleotide 1269
   the nucleotide sequence of SEQ ID No 2 from nucleotide 1247 to nucleotide 1263
   the nucleotide sequence of SEQ ID No 2 from nucleotide 1249 to nucleotide 1271
   the nucleotide sequence of SEQ ID No 2 from nucleotide 1242 to nucleotide 1261
   the nucleotide sequence of SEQ ID No 2 from nucleotide 1241 to nucleotide 1261
   the nucleotide sequence of SEQ ID No 2 from nucleotide 1243 to nucleotide 1261
   the nucleotide sequence of SEQ ID No 2 from nucleotide 1240 to nucleotide 1261
   the nucleotide sequence of SEQ ID No 2 from nucleotide 1244 to nucleotide 1261
   the nucleotide sequence of SEQ ID No 2 from nucleotide 1239 to nucleotide 1261
   the nucleotide sequence of SEQ ID No 2 from nucleotide 1245 to nucleotide 1261 b. foreign DNA sequence recognizing primers for use with 5' flanking sequence recognizing primers:
   the complement of the nucleotide sequence of SEQ ID No 2 from nucleotide 1732 to nucleotide 1751
   the complement of the nucleotide sequence of SEQ ID No 2 from nucleotide 1735 to nucleotide 1754
   the complement of the nucleotide sequence of SEQ ID No 2 from nucleotide 1731 to nucleotide 1750
   the complement of the nucleotide sequence of SEQ ID No 2 from nucleotide 1732 to nucleotide 1750
   the complement of the nucleotide sequence of SEQ ID No 2 from nucleotide 1732 to nucleotide 1752
   the complement of the nucleotide sequence of SEQ ID No 2 from nucleotide 1731 to nucleotide 1749
   the complement of the nucleotide sequence of SEQ ID No 2 from nucleotide 1732 to nucleotide 1749
   the complement of the nucleotide sequence of SEQ ID No 2 from nucleotide 1731 to nucleotide 1751
   the complement of the nucleotide sequence of SEQ ID No 2 from nucleotide 1732 to nucleotide 1753
   the complement of the nucleotide sequence of SEQ ID No 2 from nucleotide 1731 to nucleotide 1748
   the complement of the nucleotide sequence of SEQ ID No 2 from nucleotide 1732 to nucleotide 1748
   the complement of the nucleotide sequence of SEQ ID No 2 from nucleotide 1735 to nucleotide 1751
   the complement of the nucleotide sequence of SEQ ID No 2 from nucleotide 1731 to nucleotide 1752
   the complement of the nucleotide sequence of SEQ ID No 2 from nucleotide 1732 to nucleotide 1754
   the complement of the nucleotide sequence of SEQ ID No 2 from nucleotide 1731 to nucleotide 1747
   the complement of the nucleotide sequence of SEQ ID No 2 from nucleotide 1731 to nucleotide 1753
   the complement of the nucleotide sequence of SEQ ID No 2 from nucleotide 1727 to nucleotide 1746
   the complement of the nucleotide sequence of SEQ ID No 2 from nucleotide 1727 to nucleotide 1745
   the complement of the nucleotide sequence of SEQ ID No 2 from nucleotide 1727 to nucleotide 1747
   the complement of the nucleotide sequence of SEQ ID No 2 from nucleotide 1727 to nucleotide 1744
   the complement of the nucleotide sequence of SEQ ID No 2 from nucleotide 1727 to nucleotide 1748 the complement of the nucleotide sequence of SEQ ID No 2 from nucleotide 1727 to nucleotide 1749
the complement of the nucleotide sequence of SEQ ID No 2 from nucleotide 1726 to nucleotide 1745
the complement of the nucleotide sequence of SEQ ID No 2 from nucleotide 1726 to nucleotide 1744
the complement of the nucleotide sequence of SEQ ID No 2 from nucleotide 1726 to nucleotide 1746
the complement of the nucleotide sequence of SEQ ID No 2 from nucleotide 1726 to nucleotide 1747
the complement of the nucleotide sequence of SEQ ID No 2 from nucleotide 1726 to nucleotide 1748
the complement of the nucleotide sequence of SEQ ID No 2 from nucleotide 1724 to nucleotide 1744
the complement of the nucleotide sequence of SEQ ID No 2 from nucleotide 1724 to nucleotide 1745
the complement of the nucleotide sequence of SEQ ID No 2 from nucleotide 1724 to nucleotide 1746
the complement of the nucleotide sequence of SEQ ID No 2 from nucleotide 1461 to nucleotide 1478
the complement of the nucleotide sequence of SEQ ID No 2 from nucleotide 1670 to nucleotide 1686
the complement of the nucleotide sequence of SEQ ID No 2 from nucleotide 1469 to nucleotide 1486
the complement of the nucleotide sequence of SEQ ID No 2 from nucleotide 1508 to nucleotide 1527
the complement of the nucleotide sequence of SEQ ID No 2 from nucleotide 1667 to nucleotide 1686
the complement of the nucleotide sequence of SEQ ID No 2 from nucleotide 1670 to nucleotide 1687
the complement of the nucleotide sequence of SEQ ID No 2 from nucleotide 1673 to nucleotide 1689
the complement of the nucleotide sequence of SEQ ID No 2 from nucleotide 1688 to nucleotide 1704
the complement of the nucleotide sequence of SEQ ID No 2 from nucleotide 1688 to nucleotide 1705
the complement of the nucleotide sequence of SEQ ID No 2 from nucleotide 1692 to nucleotide 1709
the complement of the nucleotide sequence of SEQ ID No 2 from nucleotide 1467 to nucleotide 1486
the complement of the nucleotide sequence of SEQ ID No 2 from nucleotide 1481 to nucleotide 1497
the complement of the nucleotide sequence of SEQ ID No 2 from nucleotide 1481 to nucleotide 1498
the complement of the nucleotide sequence of SEQ ID No 2 from nucleotide 1491 to nucleotide 1507
the complement of the nucleotide sequence of SEQ ID No 2 from nucleotide 1491 to nucleotide 1508
the complement of the nucleotide sequence of SEQ ID No 2 from nucleotide 1672 to nucleotide 1688
the complement of the nucleotide sequence of SEQ ID No 2 from nucleotide 1673 to nucleotide 1690
the complement of the nucleotide sequence of SEQ ID No 2 from nucleotide 1673 to nucleotide 1691
the complement of the nucleotide sequence of SEQ ID No 2 from nucleotide 1688 to nucleotide 1706
the complement of the nucleotide sequence of SEQ ID No 2 from nucleotide 1691 to nucleotide 1707
the complement of the nucleotide sequence of SEQ ID No 2 from nucleotide 1691 to nucleotide 1708
the complement of the nucleotide sequence of SEQ ID No 2 from nucleotide 1469 to nucleotide 1487
the complement of the nucleotide sequence of SEQ ID No 2 from nucleotide 1481 to nucleotide 1499
the complement of the nucleotide sequence of SEQ ID No 2 from nucleotide 1489 to nucleotide 1505
the complement of the nucleotide sequence of SEQ ID No 2 from nucleotide 1489 to nucleotide 1506
the complement of the nucleotide sequence of SEQ ID No 2 from nucleotide 1489 to nucleotide 1507
the complement of the nucleotide sequence of SEQ ID No 2 from nucleotide 1489 to nucleotide 1508
the complement of the nucleotide sequence of SEQ ID No 2 from nucleotide 1666 to nucleotide 1686
the complement of the nucleotide sequence of SEQ ID No 2 from nucleotide 1667 to nucleotide 1687
the complement of the nucleotide sequence of SEQ ID No 2 from nucleotide 1670 to nucleotide 1688
the complement of the nucleotide sequence of SEQ ID No 2 from nucleotide 1672 to nucleotide 1689
the complement of the nucleotide sequence of SEQ ID No 2 from nucleotide 1688 to nucleotide 1707
the complement of the nucleotide sequence of SEQ ID No 2 from nucleotide 1691 to nucleotide 1709
the complement of the nucleotide sequence of SEQ ID No 2 from nucleotide 1692 to nucleotide 1710
the complement of the nucleotide sequence of SEQ ID No 2 from nucleotide 1481 to nucleotide 1500
the complement of the nucleotide sequence of SEQ ID No 2 from nucleotide 1491 to nucleotide 1509
the complement of the nucleotide sequence of SEQ ID No 2 from nucleotide 1670 to nucleotide 1689
the complement of the nucleotide sequence of SEQ ID No 2 from nucleotide 1672 to nucleotide 1690
the complement of the nucleotide sequence of SEQ ID No 2 from nucleotide 1672 to nucleotide 1691
the complement of the nucleotide sequence of SEQ ID No 2 from nucleotide 1687 to nucleotide 1705
the complement of the nucleotide sequence of SEQ ID No 2 from nucleotide 1687 to nucleotide 1706
the complement of the nucleotide sequence of SEQ ID No 2 from nucleotide 1691 to nucleotide 1710
the complement of the nucleotide sequence of SEQ ID No 2 from nucleotide 1472 to nucleotide 1488
the complement of the nucleotide sequence of SEQ ID No 2 from nucleotide 1488 to nucleotide 1507
the complement of the nucleotide sequence of SEQ ID No 2 from nucleotide 1491 to nucleotide 1510
the complement of the nucleotide sequence of SEQ ID No 2 from nucleotide 1495 to nucleotide 1512
the complement of the nucleotide sequence of SEQ ID No 2 from nucleotide 1495 to nucleotide 1513
the complement of the nucleotide sequence of SEQ ID No 2 from nucleotide 1495 to nucleotide 1514
the complement of the nucleotide sequence of SEQ ID No 2 from nucleotide 1673 to nucleotide 1692
the complement of the nucleotide sequence of SEQ ID No 2 from nucleotide 1678 to nucleotide 1694
the complement of the nucleotide sequence of SEQ ID No 2 from nucleotide 1678 to nucleotide 1695
the complement of the nucleotide sequence of SEQ ID No 2 from nucleotide 1678 to nucleotide 1696
the complement of the nucleotide sequence of SEQ ID No 2 from nucleotide 1687 to nucleotide 1703
the complement of the nucleotide sequence of SEQ ID No 2 from nucleotide 1687 to nucleotide 1704
the complement of the nucleotide sequence of SEQ ID No 2 from nucleotide 1692 to nucleotide 1711
the complement of the nucleotide sequence of SEQ ID No 2 from nucleotide 1469 to nucleotide 1488
the complement of the nucleotide sequence of SEQ ID No 2 from nucleotide 1488 to nucleotide 1506 the complement of the nucleotide sequence of SEQ ID No 2 from nucleotide 1491 to nucleotide 1511
the complement of the nucleotide sequence of SEQ ID No 2 from nucleotide 1670 to nucleotide 1690
the complement of the nucleotide sequence of SEQ ID No 2 from nucleotide 1678 to nucleotide 1697
the complement of the nucleotide sequence of SEQ ID No 2 from nucleotide 1688 to nucleotide 1709
the complement of the nucleotide sequence of SEQ ID No 2 from nucleotide 1467 to nucleotide 1487
the complement of the nucleotide sequence of SEQ ID No 2 from nucleotide 1488 to nucleotide 1508
the complement of the nucleotide sequence of SEQ ID No 2 from nucleotide 1495 to nucleotide 1511
the complement of the nucleotide sequence of SEQ ID No 2 from nucleotide 1491 to nucleotide 1512
the complement of the nucleotide sequence of SEQ ID No 2 from nucleotide 1666 to nucleotide 1687
the complement of the nucleotide sequence of SEQ ID No 2 from nucleotide 1667 to nucleotide 1688
the complement of the nucleotide sequence of SEQ ID No 2 from nucleotide 1672 to nucleotide 1692
the complement of the nucleotide sequence of SEQ ID No 2 from nucleotide 1673 to nucleotide 1693
the complement of the nucleotide sequence of SEQ ID No 2 from nucleotide 1687 to nucleotide 1707
the complement of the nucleotide sequence of SEQ ID No 2 from nucleotide 1472 to nucleotide 1490
the complement of the nucleotide sequence of SEQ ID No 2 from nucleotide 1472 to nucleotide 1491
the complement of the nucleotide sequence of SEQ ID No 2 from nucleotide 1481 to nucleotide 1501
the complement of the nucleotide sequence of SEQ ID No 2 from nucleotide 1489 to nucleotide 1509
the complement of the nucleotide sequence of SEQ ID No 2 from nucleotide 1495 to nucleotide 1515
the complement of the nucleotide sequence of SEQ ID No 2 from nucleotide 1670 to nucleotide 1691
the complement of the nucleotide sequence of SEQ ID No 2 from nucleotide 1673 to nucleotide 1694
the complement of the nucleotide sequence of SEQ ID No 2 from nucleotide 1678 to nucleotide 1698
the complement of the nucleotide sequence of SEQ ID No 2 from nucleotide 1469 to nucleotide 1489
the complement of the nucleotide sequence of SEQ ID No 2 from nucleotide 1667 to nucleotide 1689
the complement of the nucleotide sequence of SEQ ID No 2 from nucleotide 1687 to nucleotide 1708
the complement of the nucleotide sequence of SEQ ID No 2 from nucleotide 1688 to nucleotide 1710
the complement of the nucleotide sequence of SEQ ID No 2 from nucleotide 1691 to nucleotide 1711
the complement of the nucleotide sequence of SEQ ID No 2 from nucleotide 1472 to nucleotide 1492
the complement of the nucleotide sequence of SEQ ID No 2 from nucleotide 1489 to nucleotide 1510
the complement of the nucleotide sequence of SEQ ID No 2 from nucleotide 1666 to nucleotide 1688
the complement of the nucleotide sequence of SEQ ID No 2 from nucleotide 1687 to nucleotide 1709
the complement of the nucleotide sequence of SEQ ID No 2 from nucleotide 1692 to nucleotide 1712
the complement of the nucleotide sequence of SEQ ID No 2 from nucleotide 1467 to nucleotide 1488
the complement of the nucleotide sequence of SEQ ID No 2 from nucleotide 1469 to nucleotide 1490
the complement of the nucleotide sequence of SEQ ID No 2 from nucleotide 1488 to nucleotide 1509
the complement of the nucleotide sequence of SEQ ID No 2 from nucleotide 1489 to nucleotide 1511
the complement of the nucleotide sequence of SEQ ID No 2 from nucleotide 1678 to nucleotide 1699
the complement of the nucleotide sequence of SEQ ID No 2 from nucleotide 1472 to nucleotide 1493
the complement of the nucleotide sequence of SEQ ID No 2 from nucleotide 1472 to nucleotide 1494
the complement of the nucleotide sequence of SEQ ID No 2 from nucleotide 1481 to nucleotide 1502
the complement of the nucleotide sequence of SEQ ID No 2 from nucleotide 1670 to nucleotide 1692
the complement of the nucleotide sequence of SEQ ID No 2 from nucleotide 1469 to nucleotide 1491
the complement of the nucleotide sequence of SEQ ID No 2 from nucleotide 1488 to nucleotide 1510
the complement of the nucleotide sequence of SEQ ID No 2 from nucleotide 1691 to nucleotide 1712
the complement of the nucleotide sequence of SEQ ID No 2 from nucleotide 1692 to nucleotide 1713
the complement of the nucleotide sequence of SEQ ID No 2 from nucleotide 1692 to nucleotide 1714
the complement of the nucleotide sequence of SEQ ID No 2 from nucleotide 1467 to nucleotide 1489
the complement of the nucleotide sequence of SEQ ID No 2 from nucleotide 1678 to nucleotide 1700
the complement of the nucleotide sequence of SEQ ID No 2 from nucleotide 1481 to nucleotide 1503
the complement of the nucleotide sequence of SEQ ID No 2 from nucleotide 1691 to nucleotide 1713 c. 3' flanking sequence recognizing primers:
the complement of the nucleotide sequence of SEQ ID No 3 from nucleotide 828 to nucleotide 847
the complement of the nucleotide sequence of SEQ ID No 3 from nucleotide 830 to nucleotide 849
the complement of the nucleotide sequence of SEQ ID No 3 from nucleotide 828 to nucleotide 846
the complement of the nucleotide sequence of SEQ ID No 3 from nucleotide 828 to nucleotide 848
the complement of the nucleotide sequence of SEQ ID No 3 from nucleotide 830 to nucleotide 848
the complement of the nucleotide sequence of SEQ ID No 3 from nucleotide 830 to nucleotide 850
the complement of the nucleotide sequence of SEQ ID No 3 from nucleotide 828 to nucleotide 845
the complement of the nucleotide sequence of SEQ ID No 3 from nucleotide 830 to nucleotide 847
the complement of the nucleotide sequence of SEQ ID No 3 from nucleotide 828 to nucleotide 849
the complement of the nucleotide sequence of SEQ ID No 3 from nucleotide 830 to nucleotide 851
the complement of the nucleotide sequence of SEQ ID No 3 from nucleotide 828 to nucleotide 844
the complement of the nucleotide sequence of SEQ ID No 3 from nucleotide 830 to nucleotide 846
the complement of the nucleotide sequence of SEQ ID No 3 from nucleotide 828 to nucleotide 850
the complement of the nucleotide sequence of SEQ ID No 3 from nucleotide 830 to nucleotide 852
the complement of the nucleotide sequence of SEQ ID No 3 from nucleotide 992 to nucleotide 1009
the complement of the nucleotide sequence of SEQ ID No 3 from nucleotide 731 to nucleotide 752
the complement of the nucleotide sequence of SEQ ID No 3 from nucleotide 776 to nucleotide 795 the complement of the nucleotide sequence of SEQ ID No 3 from nucleotide 731 to nucleotide 753
the complement of the nucleotide sequence of SEQ ID No 3 from nucleotide 776 to nucleotide 794
the complement of the nucleotide sequence of SEQ ID No 3 from nucleotide 776 to nucleotide 796
the complement of the nucleotide sequence of SEQ ID No 3 from nucleotide 776 to nucleotide 793
the complement of the nucleotide sequence of SEQ ID No 3 from nucleotide 776 to nucleotide 797
the complement of the nucleotide sequence of SEQ ID No 3 from nucleotide 776 to nucleotide 792
the complement of the nucleotide sequence of SEQ ID No 3 from nucleotide 776 to nucleotide 798
the complement of the nucleotide sequence of SEQ ID No 3 from nucleotide 733 to nucleotide 752
the complement of the nucleotide sequence of SEQ ID No 3 from nucleotide 733 to nucleotide 753
the complement of the nucleotide sequence of SEQ ID No 3 from nucleotide 733 to nucleotide 754
the complement of the nucleotide sequence of SEQ ID No 3 from nucleotide 733 to nucleotide 755
the complement of the nucleotide sequence of SEQ ID No 3 from nucleotide 838 to nucleotide 854
the complement of the nucleotide sequence of SEQ ID No 3 from nucleotide 246 to nucleotide 263
the complement of the nucleotide sequence of SEQ ID No 3 from nucleotide 838 to nucleotide 855
the complement of the nucleotide sequence of SEQ ID No 3 from nucleotide 245 to nucleotide 264 d. foreign DNA sequence recognizing primers for use with 3' flanking sequence recognizing primers:
the nucleotide sequence of SEQ ID No 3 from nucleotide 173 to nucleotide 192
the nucleotide sequence of SEQ ID No 3 from nucleotide 22 to nucleotide 41
the nucleotide sequence of SEQ ID No 3 from nucleotide 172 to nucleotide 192
the nucleotide sequence of SEQ ID No 3 from nucleotide 174 to nucleotide 192
the nucleotide sequence of SEQ ID No 3 from nucleotide 191 to nucleotide 210
the nucleotide sequence of SEQ ID No 3 from nucleotide 171 to nucleotide 192
the nucleotide sequence of SEQ ID No 3 from nucleotide 175 to nucleotide 192
the nucleotide sequence of SEQ ID No 3 from nucleotide 190 to nucleotide 210
the nucleotide sequence of SEQ ID No 3 from nucleotide 192 to nucleotide 210
the nucleotide sequence of SEQ ID No 3 from nucleotide 176 to nucleotide 192
the nucleotide sequence of SEQ ID No 3 from nucleotide 189 to nucleotide 210
the nucleotide sequence of SEQ ID No 3 from nucleotide 193 to nucleotide 210
the nucleotide sequence of SEQ ID No 3 from nucleotide 188 to nucleotide 210
the nucleotide sequence of SEQ ID No 3 from nucleotide 194 to nucleotide 210
the nucleotide sequence of SEQ ID No 3 from nucleotide 199 to nucleotide 218
the nucleotide sequence of SEQ ID No 3 from nucleotide 200 to nucleotide 218
the nucleotide sequence of SEQ ID No 3 from nucleotide 197 to nucleotide 218
the nucleotide sequence of SEQ ID No 3 from nucleotide 201 to nucleotide 218
the nucleotide sequence of SEQ ID No 3 from nucleotide 201 to nucleotide 220
the nucleotide sequence of SEQ ID No 3 from nucleotide 200 to nucleotide 220
the nucleotide sequence of SEQ ID No 3 from nucleotide 199 to nucleotide 220
the nucleotide sequence of SEQ ID No 3 from nucleotide 200 to nucleotide 221
the nucleotide sequence of SEQ ID No 3 from nucleotide 199 to nucleotide 221
the nucleotide sequence of SEQ ID No 3 from nucleotide 150 to nucleotide 172

As used herein, "the nucleotide sequence of SEQ ID No. Z from position X to position Y" indicates the nucleotide sequence including both nucleotide endpoints.

Preferably, the amplified fragment has a length of between 50 and 500 nucleotides, such as a length between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

Detection of integration fragments can occur in various ways, e.g., via size estimation after gel analysis. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of EE-GM3 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in "PCR Applications Manual" (Roche Molecular Biochemicals, 2nd Edition, 1999) and other references. The optimal conditions for the PCR, including the sequence of the specific primers, are specified in a "PCR (or Polymerase Chain Reaction) Identification Protocol" for each elite event. It is however understood that a number of parameters in the PCR Identification Protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR Identification Protocol. These adjustments will however be apparent to a person skilled in the art, and are further more detailed in current PCR application manuals such as the one cited above.

Alternatively, specific primers can be used to amplify an integration fragment that can be used as a "specific probe" for identifying EE-GM3 in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g., via labeling of the nucleic acid or probe), whereby the formation of this hybrid indicates the presence of EE-GM3. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

Oligonucleotides suitable as PCR primers for detection of the elite event EE-GM3 can also be used to develop a PCR-based protocol to determine the zygosity status of plants containing the elite event. To this end, two primers recognizing the wild-type locus before integration are designed in such a way that they are directed towards each other and have the insertion site located in between the primers. These primers may be primers specifically recognizing the 5' and 3' flanking sequences contained within SEQ ID NO 2 or 3, respectively. These primers may also be primers specifically recognizing the 5' or 3' flanking sequence. For the current invention, particularly suitable primers recognizing the wild type locus before integration are primers comprising or consisting (essentially) of the nucleotide sequence of SEQ ID No 4 and SEQ ID 6. This set of primers, together with a third primer complementary to transforming DNA sequences (such as a primer comprising or consisting (essentially) of the nucleotide sequence of SEQ ID No 7) allow simultaneous diagnostic PCR amplification of the EE-GM3 specific locus, as well as of the wild type locus. If the plant is homozygous for the transgenic locus or the corresponding wild type locus, the diagnostic PCR will give rise to a single PCR product typical, preferably typical in length, for either the transgenic or wild type locus. If the plant is hemizygous for the transgenic locus, two locus-specific PCR products will appear, reflecting both the amplification of the transgenic and wild type locus.

Furthermore, detection methods specific for elite event EE-GM3 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage", incorporated herein by reference). To this end, the target sequence is hybridized with a labeled first nucleic acid oligonucleotide comprising the nucleotide sequence of SEQ ID No 2 from nucleotide 1452 to nucleotide 1469 or its complement or said labeled nucleic acid probe comprising the nucleotide sequence of SEQ ID No 3 from nucleotide 223 to nucleotide 240 or its complement and is further hybridized with a second nucleic acid oligonucleotide comprising the nucleotide sequence of SEQ ID No 2 from nucleotide 1434 to nucleotide 1451 or its complement or said labeled nucleic acid probe comprising the nucleotide sequence of SEQ ID No 3 from nucleotide 241 to nucleotide 258 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

A "kit" as used herein refers to a set of reagents for the purpose of performing the method of the invention, more particularly, the identification of the elite event EE-GM3 in biological samples or the determination of the zygosity status of EE-GM3 containing plant material. More particularly, a preferred embodiment of the kit of the invention comprises at least one or two specific primers, as described above for identification of the elite event, or three specific primers for the determination of the zygosity status. Optionally, the kit can further comprise any other reagent described herein in the PCR Identification Protocol. Alternatively, according to another embodiment of this invention, the kit can comprise a specific probe, as described above, which specifically hybridizes with nucleic acid of biological samples to identify the presence of EE-GM3 therein. Optionally, the kit can further comprise any other reagent (such as but not limited to hybridizing buffer, label) for identification of EE-GM3 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology Center). Sequences are indicated as "essentially similar" when such sequences have a sequence identity of at least about 75%, particularly at least about 80%, more particularly at least about 85%, quite particularly at least about 90%, especially at least about 95%, more especially at least about 98%, or at least about 99%. It is clear that when RNA sequences are said to be essentially similar or have a certain degree of sequence identity with DNA sequences, thymidine (T) in the DNA sequence is considered equal to uracil (U) in the RNA sequence. Also, it is clear that small differences or mutations may appear in DNA sequences over time and that some mismatches can be allowed for the event-specific primers or probes of the invention, so any DNA sequence indicated herein in any embodiment of this invention for any 3' or 5' flanking DNA or for any insert or foreign DNA or any primer or probe of this invention, also includes sequences essentially similar to the sequences provided herein, such as sequences hybridizing to or with at least 90%, 95%, 96%, 97%, 98%, or at least 99% sequence identity to the sequence given for any 3' or 5' flanking DNA, for any primer or probe or for any insert or foreign DNA of this invention.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR Identification Protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological sample is a sample of a plant, plant material or products comprising plant material. The term "plant" is intended to encompass soybean (*Glycine max*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for EE-GM3, implying the presence of nucleic acids in the samples. Thus the methods referred to herein for identifying elite event EE-GM3 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, such as promoter and transcript termination sequences.

The present invention also relates to the development of an elite event EE-GM3 in soybean plants comprising this event, the progeny plants and seeds comprising elite event EE-GM3 obtained from these plants and to the plant cells, or plant material derived from plants comprising this event. Plants comprising elite event EE-GM3 can be obtained as described in Example 1. This invention also relates to seed comprising elite event EE-GM3 deposited at the NUMB under deposit number NCIMB 41659 or derivatives therefrom comprising elite event EE-GM3. "Derivatives (of seed)" as used herein, refers to plants which can be grown from such seed, progeny resulting from crossing or backcrossing, as well as plant cells, organs, parts, tissue, cell cultures, protoplasts, and plant material of same.

Soybean plants or plant material comprising EE-GM3 can be identified according to the PCR Identification Protocol described for EE-GM3 in Example 2. Briefly, soybean genomic DNA present in the biological sample is amplified by PCR using a primer which specifically recognizes a sequence within the 5' or 3' flanking sequence of EE-GM3 such as the primer with the sequence of SEQ ID NO: 5, and a primer which recognizes a sequence in the foreign DNA, such as the primer with the sequence of SEQ ID NO: 4. DNA primers which amplify part of an endogenous soybean sequence are used as positive control for the PCR amplification. If upon PCR amplification, the material yields a fragment of the expected size, the material contains plant material from a soybean plant harboring elite event EE-GM3.

Plants harboring EE-GM3 are characterized by their glyphosate tolerance, as well as by their tolerance to HPPD inhibitors such as isoxaflutole. Plants harboring EE-GM3 are also characterized by having agronomical characteristics that are comparable to commercially available varieties of soybean, in the absence of herbicide application. It has been observed that the presence of a foreign DNA in the insertion region of the soybean plant genome described herein, confers particularly interesting phenotypic and molecular characteristics to the plants comprising this event.

One embodiment of this invention provides an elite event in soybean plants, obtainable by insertion of 2 transgenes at a specific location in the soybean genome, which elite event confers tolerance to glyphosate and an HPPD inhibitor herbicide such as isoxaflutole on such soybean plants, and wherein such elite event does not cause any effect on the agronomic performance of such soybeans negatively affecting the yield of such soybean plants, compared to isogenic lines (as used herein, "isogenic lines" or "near-isogenic lines" are soybean lines of the same genetic background but lacking the transgenes, such as plants of the same genetic background as the plant used for transformation, or segregating sister lines having lost the transgenes). Particularly, the current invention provides an elite event in soybean plants, wherein the insertion or presence of said elite event in the genome of such soybean plants does not cause an increased susceptibility to disease, does not cause a yield drag, or does not cause increased lodging, in such soybean plants, as compared to isogenic lines. Hence, the current invention provides an elite event in soybean plants, designated as EE-GM3, which results in soybean plants that can tolerate the application of glyphosate and an HPPD inhibitor herbicide (either simultaneously or separately) without negatively affecting the yield of said soybean plants compared to isogenic lines, which soybean plants have no statistically significant difference in their disease susceptibility, or lodging, as isogenic soybean plants. These characteristics make the current elite event very interesting to control glyphosate-resistant weeds in soybean fields, and can also be used in approaches to prevent or delay further glyphosate resistance development in soybean fields (e.g., by application of glyphosate and isoxaflutole, securing 2 modes of actions applied on a soybean field).

Provided herein is also a soybean plant or part thereof comprising event EE-GM3, wherein representative soybean seed comprising event EE-GM3 has been deposited under NCIMB accession number 41659. Further provided herein are seeds of such plants, comprising such event, as well as a soybean product produced from such seeds, wherein said soybean product comprises event EE-GM3. Such soybean product can be or can comprise meal, ground seeds, flour, flakes, etc. Particularly, such soybean product comprises a nucleic acid that produces an amplicon diagnostic or specific for event EE-GM3, such amplicon comprising SEQ ID No. 2 or 3. Also provided herein is a method for producing a soybean product, comprising obtaining soybean seed comprising event EE-GM3, and producing such soybean product therefrom.

Also provided herein is a soybean plant, which is progeny of any of the above soybean plants, and which comprises event EE-GM3.

Further provided herein is a method for producing a soybean plant tolerant to glyphosate and/or isoxaflutole herbicides, comprising introducing into the genome of such plant event EE-GM3, particularly by crossing a first soybean plant lacking event EE-GM3 with a soybean plant comprising EE-GM3, and selecting a progeny plant tolerant to glyphosate and/or isoxaflutole.

Also provided herein is a glyphosate and/or isoxaflutole tolerant plant, particularly without yield drag, and with acceptable agronomical characteristics, comprising a 2mEPSPS and HPPD protein, and capable of producing an amplicon diagnostic for event EE-GM3. Also provided herein are the specific isolated amplicons (DNA sequence fragments) as such, that can be obtained using the specific detection tools described herein, particularly amplicons including in their sequence a DNA fragment originating from plant DNA and a DNA fragment foreign or heterologous to such plant, such as the DNA inserted in the plant genome by transformation, as defined herein.

Further provided herein is a method for controlling weeds in a field of soybean plants comprising event EE-GM3, or a field to be planted with such soybean plants, comprising treating the field with an effective amount of an isoxaflutole-based herbicide, wherein such plants are tolerant to such herbicide.

Further provided herein is a DNA comprising the sequence of SEQ ID No 1 or a sequence essentially similar thereto, and any plant, cell, tissue or seed, particularly of soybean, comprising such DNA sequence, such as a plant, cell, tissue, or seed comprising EE-GM3, particularly a DNA comprising 2 adjacent regions comprising or consisting (essentially) of SEQ ID No 1, or a DNA comprising 2 adjacent regions comprising or consisting of SEQ ID No 1 with some nucleotides changed, deleted or added, such as a DNA comprising a duplication of SEQ ID No 1 with 4, 6, 8, or 10 nucleotides deleted or replaced, located close (such as 200-500 nt, or less than 2000 or 10.000 nt, separated) to one another. In one embodiment, this includes the DNA of SEQ ID No. 11 from nucleotide position 2257 to nucleotide position 16601 wherein 2, 4, 6, 8 or 10 nucleotides have been replaced by other nucleotides, or wherein 2, 4, 6, 8 or 10 nucleotides have been deleted or added, or the DNA of SEQ ID No. 11 from nucleotide position 2257 to nucleotide position 16601 of SEQ ID No 11, as well as the DNA of SEQ ID No. 11, and any plant, cell, tissue or seed, particularly of soybean, comprising any of such DNA sequences. Also included herein is any soybean plant, cell, tissue or seed, comprising the DNA sequence (heterologous or foreign to a conventional soybean plant, seed, tissue or cell) of SEQ ID No. 11, or comprising the DNA sequence of SEQ ID No. 11 from nucleotide position 2257 to nucleotide position 16601, or comprising a DNA sequence with at least 99% or 99.5% sequence identity to the sequence of SEQ ID No. 11, or comprising a DNA sequence with at least 99% or 99.5% sequence identity to the sequence of SEQ ID No. 11 from nucleotide position 2257 to nucleotide position 16601.

Also provided herein is a transgenic soybean plant, plant cell, tissue, or seed, comprising in their genome event EE-GM3 characterized by a nucleic acid molecule comprising a nucleotide sequence essentially similar to SEQ ID No. 2 from nucleotide 1441 to nucleotide 1462 and a nucleic acid molecule comprising a nucleotide sequence essentially similar to SEQ ID No. 3 from nucleotide 230 to 251, or the complement of said sequences, as well as a soybean plant, plant cell, tissue, or seed, comprising in their genome event EE-GM3 characterized by a nucleic acid molecule comprising a nucleotide sequence essentially similar to SEQ ID No. 2 and a nucleic acid molecule comprising a nucleotide sequence essentially similar to SEQ ID No. 3, or the complement of said sequences.

Even further provided herein is a soybean plant, cell, tissue or seed, comprising EE-GM3, characterized by comprising in the genome of its cells a nucleic acid sequence with at least 80%, 90%, 95% or 100% sequence identity to SEQ ID No. 2 from nucleotide 1431 to 1472 and a nucleic acid sequence with at least 80%, 90%, 95% or 100% sequence identity to SEQ ID No. 3 from nucleotide 220 to 261, or the complement of said sequences.

The term "isoxaflutole", as used herein, refers to the herbicide isoxaflutole [i.e. (5-cyclopropyl-4-isoxazolyl)[2-(methylsulfonyl)-4-(trifluoromethyl)phenyl]methanone], the active metabolite thereof, diketonitrile, and any mixtures or solutions comprising said compounds. HPPD inhibiting herbicides useful for application on the event of this invention are the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1, 3-fione; other isoxazoles; and the pyrazolinates, e.g. topramezone [i.e. [3-(4,5-dihydro-3-isoxazolyl)-2-methyl-4-(methylsulfonyl)phenyl](5-hydroxy-1-methyl-1H-pyrazol-4-yl)methanone], and pyrasulfotole [(5-hydroxy-1,3-dimethylpyrazol-4-yl(2-mesyl-4-trifluoromethylphenyl) methanone]; or pyrazofen [2-[4-(2,4-dichlorobenzoyl)-1,3-dimethylpyrazol-5-yloxy]acetophenone].

In one embodiment of this invention, a field to be planted with soybean plants containing the EE-GM3 event, can be treated with an HPPD inhibitor herbicide, such as isoxaflutole ('IFT'), before the soybean plants are planted or the seeds are sown, which cleans the field of weeds that are killed by the HPPD inhibitor, allowing for no-till practices, followed by planting or sowing of the soybeans in that same pre-treated field later on (burndown application using an HPPD inhibitor herbicide). The residual activity of IFT will also protect the emerging and growing soybean plants from competition by weeds in the early growth stages. Once the soybean plants have a certain size, and weeds tend to re-appear, glyphosate, or an HPPD inhibitor-glyphosate mixture, can be applied as post-emergent herbicide over the top of the plants.

In another embodiment of this invention, a field in which seeds containing the EE-GM3 event were sown, can be treated with an HPPD inhibitor herbicide, such as IFT, before the soybean plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing soybean plants have no competition by weeds (pre-emergence application of an HPPD inhibitor herbicide). Once the soybean plants have a certain size, and weeds tend to re-appear, glyphosate—or an HPPD inhibitor-glyphosate mixture—can be applied as post-emergent herbicide over the top of the plants.

In another embodiment of this invention, plants containing the EE-GM3 event, can be treated with an HPPD inhibitor herbicide, such as IFT, over the top of the soybean plants that have emerged from the seeds that were sown, which cleans the field of weeds killed by the HPPD inhibitor, which application can be together with (e.g., in a spray tank mix), followed by or is preceded by a treatment with glyphosate as post-emergent herbicide over the top of the plants (post-emergence application of an HPPD inhibitor herbicide (with or without glyphosate)).

Also, in accordance with the current invention, soybean plants harboring EE-GM3 may be treated with the following insecticides, herbicides or fungicides or soybean seeds harboring EE-GM3 may be coated with a coat comprising the following insecticides, herbicides or fungicides:

Soybean Herbicides:
Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole.

Soybean Insecticides:
Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, spirodiclofen, Triflumuron, Flonicamid, Thiodicarb, beta-Cyfluthrin.

Soybean Fungicides:
Azoxystrobin, Cyproconazole, Epoxiconazole, Flutriafol, Pyraclostrobin, Tebuconazole, Trifloxystrobin, Prothioconazole, Tetraconazole.

The following examples describe the development and identification of elite event EE-GM3, the development of different soybean lines comprising this event, and the development of tools for the specific identification of elite event EE-GM3 in biological samples.

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy R D D (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com"

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

In the description and examples, reference is made to the following sequences:

SEQ ID No. 1: SaiI fragment nucleotide sequence of vector pSF10.

SEQ ID No. 2: nucleotide sequence comprising the 5' region flanking the foreign DNA comprising the herbicide tolerance genes in EE-GM3.

SEQ ID No. 3: nucleotide sequence comprising the 3' region flanking the foreign DNA comprising the herbicide tolerance genes in EE-GM3.

SEQ ID No. 4: primer SOY028

SEQ ID No. 5: primer SOY029

SEQ ID No. 6: primer SMP187

SEQ ID No. 7: primer STV019

SEQ ID No. 8: nucleotide sequence of the amplicon

SEQ ID No. 9: primer 1 for amplification of control fragment (SOY01)

SEQ ID No. 10: primer 2 for amplification of control fragment (SOY02)

SEQ ID No. 11: nucleotide sequence of foreign DNA and plant flanking sequences in EE-GM3

SEQ ID No. 12: primer SHA130

SEQ ID No. 13: primer SHA178

EXAMPLES

1. Transformation of *Glycine max* with Herbicide Tolerance Genes 1.1. Description of the Foreign DNA Comprising the 2mEPSPS and HPPD-Pf-W336 Chimeric Genes Plasmid pSF10 is a pUC19 derived cloning vector which contains a chimeric 2mepsps gene and a chimeric hppd-Pf-W336 gene located on a SalI fragment of about 7.3 kb. A full description of the DNA comprised between the two SalI restriction sites is given in Table 1 below. The nucleotide sequence is represented in SEQ ID No. 1.

TABLE 1

Nucleotide positions of the DNA comprised between the
SalI restriction sites of pSF10 (SEQ ID No 1)

| Nucleotide positions | Orientation | Description and references |
| --- | --- | --- |
| 188-479 | complement | 3'nos: sequence including the 3' untranslated region of the nopaline synthase gene from the T-DNA of pTiT37 of *Agrobacterium tumefaciens* (Depicker et al., 1982, Journal of Molecular and Applied Genetics, 1, 561-573) |
| 480-1556 | complement | hppdPf W336: the coding sequence of the 4-hydroxyphenylpyruvate dioxygenase of *Pseudomonas fluorescens* strain A32 modified by the replacement of the amino acid Glycine 336 with a Tryptophane, as described by Boudec et al. (2001) US Patent US6245968B1 |
| 1557-1928 | complement | TPotp Y: coding sequence of an optimized transit peptide derivative (position 55 changed into Tyrosine), containing sequence of the RuBisCO small subunit genes of *Zea mays* (corn) and *Helianthus annuus* (sunflower), as described by Lebrun et al. (1996) U.S. Pat. No. 5,510,471 |
| 1929-2069 | complement | 5'tev: sequence including the leader sequence of the tobacco etch virus as described by Carrington and Freed (1990) Journal of Virology, 64, 1590-1597 |
| 2070-3359 | complement | Ph4a748 ABBC: sequence including the promoter region of the histone H4 gene of *Arabidopsis thaliana*, containing an internal duplication (Chabouté et al., 1987) Plant Molecular Biology, 8, 179-191. |
| 3360-4374 | | Ph4a748: sequence including the promoter region of the histone H4 gene of *Arabidopsis thaliana* (Chabouté et al., 1987) Plant Molecular Biology, 8, 179-191. |
| 4375-4855 | | intron1 h3At: first intron of gene II of the histone H3.III variant of *Arabidopsis thaliana* (Chaubet et al., 1992) Journal of Molecular Biology, 225, 569-574. |
| 4856-5227 | | TPotp C: coding sequence of the optimized transit peptide, containing sequence of the RuBisCO small subunit genes of *Zea mays* (corn) and *Helianthus annuus* (sunflower), as described by Lebrun et al. (1996) U.S. Pat. No. 5,510,471 |
| 5228-6565 | | 2mepsps: the coding sequence of the double-mutant 5-enol-pyruvylshikimate-3-phosphate synthase gene of *Zea mays* (corn) (Lebrun et al., 1997) WO9704103-A1 |
| 6566-7252 | | 3'histonAt: sequence including the 3' untranslated region of the histone H4 gene of *Arabidopsis thaliana* (Chabouté et al., 1987) Plant Molecular Biology, 8, 179-191. |

1.2. Event EE-GM3

The HPLC purified SalI-linearized pSF10 fragment of about 7.3 kb (containing the 2mEPSPS glyphosate-tolerance gene and the HPPD inhibitor tolerance gene HPPD-Pf-W336) was used to obtain transformed soybean plants by means of direct gene transfer into cells of soybean type Jack (Nickell, C. D., G. R. Noel, D. J. Thomas, and R. Waller. Registration of 'Jack' soybean. *Crop Sci* 1365. 30. 1990), followed by regeneration of transformed plant cells into transgenic fertile soybean plants.

1.2.1 Identification of elite event EE-GM3

Elite event EE-GM3 was selected based on an extensive selection procedure based on good expression and stability of the herbicide tolerance genes, and its compatibility with optimal agronomic characteristics such as plant height, height to node, stand, vigor, seed yield, were evaluated. Soybean plants containing this event were selected from a wide range of different transformation events obtained using the same chimeric genes. Parameters used in the selection of this event were: a) acceptable tolerance to isoxaflutole herbicide application in field trials, b) acceptable tolerance to glyphosate herbicide application in field trials, c) acceptable tolerance to combined application of isoxaflutole and glyphosate herbicides in field trials, d) an insertion of the herbicide tolerance transgenes at a single locus in the soybean plant genome, with absence of vector backbone, e) overall agronomy similar to the parent plants used for transformation (maturity, lodging, disease susceptibility, etc.), and f) no significant yield drag caused by the insertion of the transforming DNA (as compared to an isogenic line without the event, such as the plant line used for transformation, grown under the same conditions).

At the T3 generation, a homozygous line of the soybean transformation event EE-GM3 was selected for seed production. Multi-location replicated agronomic field studies were conducted in the regions of adaptation of the parent variety, Jack. Field evaluations included herbicide tolerance and agronomic performance. The agronomic performance of plants containing EE-GM3 was found comparable to Jack (when no herbicides were applied).

The field evaluations also showed that plants carrying the EE-GM3 event have:

similar plant morphology and seed characteristics compared to Jack, no change in response to soybean diseases compared to Jack, and no changes in seed germination or dormancy compared to Jack.

Seed (T1 or S1 generation) harvested from the initial transformant (T0) plant (the plant transformed with the construct so as to produce event EE-GM3) in the greenhouse were planted in the field. Three blocks were planted and sprayed with 0, 2, or 4 kg/ha glyphosate. Seed was harvested from plants demonstrating the desired level of tolerance to the herbicide, glyphosate.

Seeds (T2 generation) harvested from self-pollinated T1 plants grown in the field were sown "plant to row". Chi square analysis of segregation data for rows (fully or partially tolerant) and of individual plants within rows (tolerant or sensitive) demonstrates the expected Mendelian inheritance of a single insertion for EE-GM3.

Selection and seed increase continued until a line was determined to be homozygous for transformation event EE-GM3 and selected for core seed production in the fourth generation. Then, T5 generation seed served as a candidate for the development of different varieties. Plants in the sixth generation (T6 generation) were crossed with conventional soybean breeding lines in an introgression program designed to move the event into a broader base of commercial soybean germplasm. F1 hybrid plants (EE-GM3 lines× conventional lines) were grown to maturity and the F2 seed was planted. Leaf samples of 901 F2 plants were analyzed by PCR primers designed to identify the zygosity of the EE-GM3 insert. The expected ratio of 1:2:1 for a single-insertion segregation by the rules of Mendel was observed.

The selected event EE-GM3 was introduced in different commercial genetic backgrounds, and results of field trials on different locations were compared. Plants were challenged with glyphosate herbicide and/or isoxaflutole herbicide using different treatments. The plants exhibited good herbicide tolerance. Hundreds of different soybean cultivars containing event EE-GM3 were used in an inheritance study, and herbicides were applied. Selected lines from this trial were later increased in the field and also treated with herbicide. From that trial, 50 selected lines were increased, and these were also herbicide treated. The phytotoxicity scores for the latter lines sprayed with isoxaflutole and glyphosate showed some variability in response, but the range of responses among the lines reflected similar variability as was observed across 4 replications of the EE-GM3 event in the original Jack background, grown under the same treatment and environmental conditions. Hence, tolerance to the relevant herbicides across a broad range of germplasm was observed for plants comprising EE-GM3.

Furthermore, plants containing the event EE-GM3 had normal leaf, flower and pod morphology, excellent fertility, and showed no disease or abnormal insect susceptibility in multiple genetic backgrounds. During introgression into multiple genetic backgrounds no aberrant problems or abnormalities were observed.

In one season, a 10-location study was designed to compare the agronomic performance of double herbicide tolerant soybean comprising transformation event EE-GM3 to the transformation parent variety, Jack and some non-transgenic soybean varieties. Using a randomized complete block design, EE-GM3 plants were grown in replicated plots with either conventional weed control or with the intended herbicides, glyphosate and isoxaflutole. Plots with soybean plants containing transformation event EE-GM3 were sprayed with isoxaflutole herbicide at a target rate of 70 grams ai/Ha and with glyphosate herbicide at a target rate of 1060 grams ai/Ha. Herbicide application was made to these plants as a foliar spray at about the V4-V5 plant growth stage. Agronomic observations were made in the early, mid and late season. The plant density (parameter; stand count) was higher for the Jack and the non-transgenic variety plots than in the event EE-GM3 plots by one standard deviation. The early stand count difference may have been the result of seed lot quality, as the EE-GM3 planting seed was produced in counter season nursery, while the seed of the non-transgenic varieties was produced in the contiguous US, normal production season. However, the number of days to achieve 50% emergence and the plant vigor ratings were the same, indicating that the seed lots were comparable for these performance parameters. In the late season stand counts, Jack and the non-transgenic varieties remained different by one standard deviation from EE-GM3 plants. Plot yields of EE-GM3 event plants were also lower than those of Jack by one standard deviation, perhaps a result of the lower plant density of the EE-GM3 event plots. The yield of the non-transgenic varieties was more than Jack as could be expected because of the advancement in yield potential found in more recent varieties.

In one trial, plant health ratings were made at three growth stages: V4-5, R1 and full maturity. The first evaluation was shortly after the intended herbicide application. At the time of the final plant health evaluation, the EE-GM3-containing plants sprayed with both herbicides had the same score as the unsprayed Jack plants, or the unsprayed plants comprising EE-GM3. In ratings by the agronomic staff, the herbicide-sprayed plants received a health rating of 3-4 (moderate injury) at the V4-5 and R1 plant growth stages. The unsprayed plants (untransformed Jack or soybean plants containing EE-GM3) were rated as 4.6-4.8 (rating of 5 indicates no injury). At the final plant health rating, all the plots received the same rating of 5 (no injury).

One trial season was one of exceptional rainfall, and crop injury in the EE-GM3 plants following the intended herbicide application was more obvious than observed in other seasons.

The field evaluations also included monitoring of the fitness characters (reproduction, disease resistance, fecundity, seed dispersal, dormancy, persistence). For the reproductive characteristics; days to emergence, days to 50% flowering and days to 90% pods maturing, the EE-GM3 and Jack plants were not different. No difference was noted in the reaction to natural infestations of plant diseases and insect pests. Although EE-GM3 produced less ultimate yield than Jack, no difference in fecundity (100-seed weight) was found. The assessment of seed dispersal parameters (pod shattering and plant lodging) found EE-GM3 and Jack to have the same pod shattering score, but found EE-GM3 plants to be less prone to lodging. Evaluation of seed harvested from the 10 locations found no concerns raised by germination or dormancy testing.

In these trials during the season with exceptional rainfall, the final yield of EE-GM3 plants, regardless of the weed control treatment, was less than the yield of Jack by one standard deviation (perhaps a result of the lower plant density of the EE-GM3 event plots). In the exceptionally wet season, crop injury (bleaching in 10-30% of the crop area) was reported for EE-GM3 plots up to six weeks following foliar application of the glyphosate and isoxaflutole herbicides. However, by maturity, "no injury" plant health ratings were assigned to all the plots. Replicated multi-location field trials with EE-GM3 introgressed in elite soybean cultivar background, when compared to near-isogenic sister lines not containing the transgene, are expected to show no yield difference between plants containing event EE-GM3 and the near-isogenic lines (in the absence of herbicide treatment).

Further, in a replicated field trial significant crop tolerance (bleaching of less than 10%) was found in soybean plants comprising EE-GM3 when treated either pre- or post-emergence with IFT (70 gr ai/ha with 0.5% NIS, Agridex), but also significant crop tolerance (bleaching of less than 10%) was found in soybean plants comprising EE-GM3 when treated with a post-emergence application of pyrasulfotole (35 gr ai/ha with 0.5% NIS, Agridex), another HPPD inhibitor herbicide.

1.2.2. Identification of the Flanking Regions and Foreign DNA of Elite Event EE-GM3

The sequence of the regions flanking the foreign DNA comprising the herbicide tolerance genes in the EE-GM3 elite event was determined to be as follows:

1.2.2.1. Right (5') Flanking Region

The fragment identified as comprising the 5' flanking region was sequenced and its nucleotide sequence is represented in SEQ ID No. 2. The sequence between nucleotide 1 and 1451 corresponds to plant DNA, while the sequence between nucleotide 1452 and 1843 corresponds to foreign DNA.

1.2.2.2. Left (3') Flanking Region

The fragment identified as comprising the 3' flanking region was sequenced and its nucleotide sequence is represented in SEQ ID No. 3. The sequence between nucleotide 1 and 240 corresponds to foreign DNA, while the sequence between nucleotide 241 and 1408 corresponds to plant DNA.

1.2.2.3. Foreign DNA Comprising the Herbicide Tolerance Genes of EE-GM3

Using different molecular techniques, it has been determined that the foreign DNA of elite event EE-GM3 comprising the herbicide tolerance genes contains two partial 3' histonAt sequences in a head-to-head orientation, followed by 2 almost complete copies of the SalI fragment of pSF10 arranged in head-to-tail orientation (see FIG. 1).

The foreign DNA comprising the herbicide tolerance genes of EE-GM3 thus contains in order the following sequences:

from nucleotide 1 to nucleotide 199: the nucleotide sequence corresponding to complement of the nucleotide sequence of SEQ ID 1 from nt 6760 to nt 6958;
from nucleotide 200 to nucleotide 624: the nucleotide sequence corresponding to the nucleotide sequence of SEQ ID 1 from nt 6874 to nt 7298;
from nucleotide 625 to nucleotide 7909: the nucleotide sequence corresponding to the nucleotide sequence of SEQ ID 1 from nt 7 to nt 7291;
from nucleotide 7910 to nucleotide 15163: the nucleotide sequence corresponding to the nucleotide sequence of SEQ ID 1 from nt 12 to nt 7265; and
from nucleotide 15164 to nucleotide 15187: the nucleotide sequence corresponding to the nucleotide sequence of SEQ ID 3 from nt 217 to nt 240 (this sequence does not correspond to either pSF10 plasmid DNA or wt plant DNA and therefore is designated filler DNA).

This foreign DNA is preceded immediately upstream and contiguous with the foreign DNA by the 5' flanking sequence of SEQ ID No 2 from nucleotide 1 to 1451 and is followed immediately downstream and contiguous with the foreign DNA by the 3' flanking sequence of SEQ ID No 3 from nucleotide 241 to nucleotide 1408.

Confirmed full DNA sequencing of the foreign DNA and flanking DNA sequences in EE-GM3 resulted in the sequence reported in SEQ ID No. 11. In this sequence, the inserted DNA is from nucleotide position 1452 to nucleotide position 16638, and the 2 almost complete copies from pSF10 arranged in head-to-tail orientation are from nucleotide position 2257 to nucleotide position 16601. The 5' flanking DNA sequence in SEQ ID No. 11 is the sequence from nucleotide position 1 to nucleotide position 1451 in SEQ ID No. 11, and the 3' flanking DNA sequence in SEQ ID No. 11 is the sequence from nucleotide position 16639 to nucleotide position 17806 in SEQ ID No. 11.

2. Development of Polymerase Chain Reaction Identification Protocols for EE-GM3

2.1. Primers

Specific primers were developed which recognize sequences within the elite event.

A primer was developed which recognizes a sequence within the 3' flanking region of EE-GM3. A second primer was then selected within the sequence of the foreign DNA so that the primers span a sequence of about 263 nucleotides. The following primers were found to give particularly clear and reproducible results in a PCR reaction on EE-GM3 DNA:

```
                                        (SEQ ID No.: 4)
SOY28:   5'-ATC.gCT.TTA.ACg.TCC.CTC.Ag-3
         (target: insert DNA)

(SEQ ID No.: 5)
SOY29:   5'-CAA.ggC.CTC.gA.ATT.ATC-3'
         (target: plant DNA)
```

Primers targeting an endogenous sequence are preferably included in the PCR cocktail. These primers serve as an internal control in unknown samples and in the DNA positive control. A positive result with the endogenous primer-pair (presence of an PCR amplified fragment of 413 bp) demonstrates that there is ample DNA of adequate quality in the genomic DNA preparation for a PCR product to be generated. The endogenous primers were selected to recognize the endogenous actin soybean gene:

```
                                        (SEQ ID No.: 9)
SOY01    5'-gTC.AgC.CAC.ACA.gTg.CCT.AT-3'

(SEQ ID No.: 10)
SOY02    5'-gTT.ACC.gTA.CAg.gTC.TTT.CC-3'
```

2.2. Amplified Fragments

The expected amplified fragments in the PCR reaction are:

For primer pair SOY01-SOY02: 413 bp (endogenous control)

For primer pair SOY028-SOY029: 263 bp (EE-GM3 elite event)

2.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

2.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

2.5. PCR Conditions

Optimal results were obtained under the following conditions (In describing the various conditions for optimal results is meant to provide examples of such conditions. Clearly one skilled in the art could vary conditions, reagents and parameters such as using other Taq polymerases, and achieve desirable results):

the PCR mix for 25 µl reactions contains:
20 ng template DNA
2.5 µl 10× Amplification Buffer (supplied by the manufacturer with the Taq polymerase)
0.5 µl 10 mM dNTP's
0.4 µl SOY01 (10 pmoles/µl)
0.4 µl SOY02 (10 pmoles/µl)
0.7 µl SOY028 (10 pmoles/µl)
0.7 µl SOY029 (10 pmoles/µl)
0.1 µl Taq DNA polymerase (5 units/µl) water up to 25 µl the thermocycling profile to be followed for optimal results is the following:
4 min. at 95° C.
Followed by: 1 min. at 95° C.
1 min. at 57° C.
2 min. at 72° C.
For 5 cycles
Followed by: 30 sec. at 92° C.
30 sec. at 57° C.
1 min. at 72° C.
For 25 cycles
Followed by: 10 minutes at 72° C.

2.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder Pharmacia).

2.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for EE-GM3 as described above, lanes showing visible amounts of the transgenic and endogenous PCR products of the expected sizes, indicate that the corresponding plant from which the genomic template DNA was prepared, has inherited the EE-GM3 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

2.8. Use of Discriminating PCR Protocol to Identify EE-GM3

Before attempting to screen unknowns, a test run, with all appropriate controls, is performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and the transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Leaf material from a number of soybean plants, some of which comprising EE-GM3 were tested according to the above-described protocol. Samples from elite event EE-GM3 and from soybean wild-type were taken as positive and negative controls, respectively.

Figure 2:
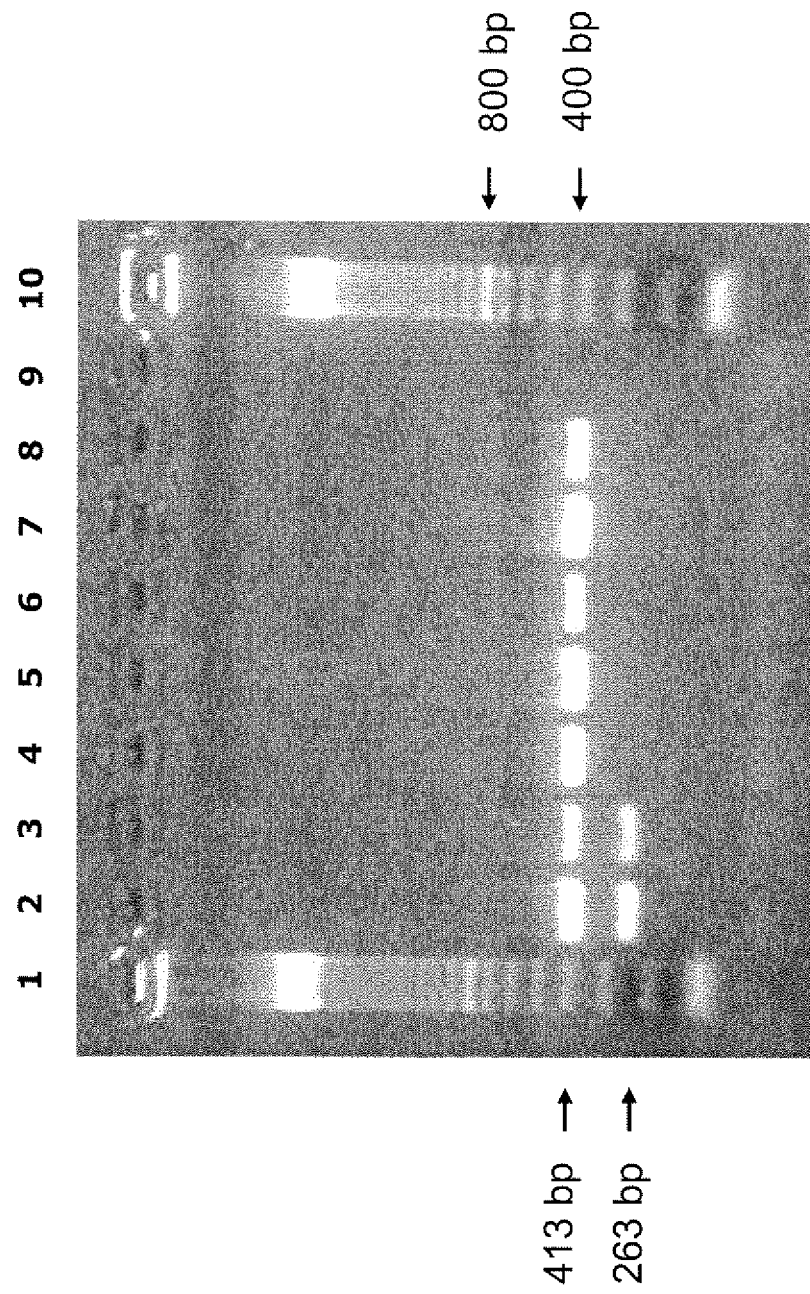
FIG. 2: Results obtained by the PCR Identification Protocol developed for EE-GM3. Loading sequence of the gel: Lane 1: Molecular weight marker (100 bp ladder); lanes 2 and 3: DNA samples from soybean plants comprising the transgenic event EE-GM3; lanes 4-7: DNA samples from transgenic soybean plants not comprising elite event EE-GM3, but comprising the same herbicide tolerance genes (other transformation events); lane 8: DNA sample from wild type soybean; lane 9: no-template DNA control; lane 10: molecular weight marker.

FIG. 2 illustrates the result obtained with the elite event PCR Identification Protocol for EE-GM3 on a number of soybean plant samples. The samples in lanes 2 and 3 were found to contain elite event EE-GM3 as the 263 bp band is detected, while the samples in lanes 4 to 8 do not comprise EE-GM3. Lanes 6 and 7 comprise samples from other soybean transformation events obtained using the same herbicide tolerance chimeric genes; lane 8 contains DNA from wild type soybean plants and lane 9 represents the negative control (water) sample, lanes 1 and 10 represent the Molecular Weight Marker (100 bp ladder).

2.9. dPCR Assay for EE-GM3 Detection in Bulked Seed

A discriminating PCR (dPCR) assay is set up to detect low level presence of EE-GM3 in bulked seeds. A minimum level of 0.4% (w/w) of transgenic seeds in a bulk of non transgenic seeds was successfully detected under repeatable conditions. Therefore the Limit of Detection is determined to be 0.4% (w/w).

The following primers are applied in this target PCR reaction:

```
Forward primer targeted to the T-DNA sequence:
                                  (SEQ ID No. 12)
SHA130   5'-CTA.TAT.TCT.ggT.TCC.AAT.TTA.TC-3'

Reverse primer targeted to the 3' flanking
sequence:
                                  (SEQ ID No. 13)
SMP178   5'-TgA.ggC.ACg.TAT.TgA.TgA.CC-3'
```

The expected amplified fragment in the PCR reaction from these primers is 115 bp.

The target PCR reaction is performed on approximately 200 ng of template DNA prepared from ground bulked seed according to a modified Gentra Puregene DNA purification extraction kit (Qiagen). When using DNA prepared with other methods, a test run using samples with known relative levels of EE-GM3 should be performed.

A validated reference system PCR reaction, targeting an endogenous sequence, should ideally be performed in a separate PCR run to verify the suitability of the DNA sample for PCR analysis to avoid false negative results.

For unknown test samples the PCR experiment should ideally include the appropriate positive and negative control samples, i.e.:

Master Mix control (DNA negative control). This is a PCR in which no DNA is added to the reaction. When the expected result (no PCR product) is observed for both the target and the reference system reaction this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

Also a wild-type DNA control can be added in this PCR. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

Optimal results are obtained under the following conditions:

Obviously, other Taq polymerases can be used, and then the conditions can differ to follow supplier recommendations.

the PCR mix for 250 reactions contains:
200 ng template DNA
5 µl 5× Reaction Buffer
0.25 µl 20 mM dNTP's
0.7 µl SHA130 (10 pmoles/l)
0.4 µl SMP178 (10 pmoles/l)
0.1 µl GO-Taq DNA polymerase (5 units/l)
Add water up to 25 µl the thermocycling profile to be followed for optimal results is the following:
4 min. at 95° C.
Followed by: 1 min. at 95° C.
1 min. at 57° C.
2 min. at 72° C.
For 5 cycles
Followed by: 30 sec. at 92° C.
30 sec. at 57° C.
1 min. at 72° C.
For 30 cycles
Followed by: 10 minutes at 72° C.

To optimally visualize the results of the PCR it was determined that 25 µl of the PCR product should be applied on a 1.5% agarose gel (Tris-borate buffer) with an appropriate molecular weight marker (e.g. 50 bp ladder).

When following the PCR method as described above, lanes showing visible amounts of the target and reference system PCR products of the expected sizes, indicate that the test sample from which the genomic template DNA was prepared, contained levels of EE-GM3 elite event above the detection limit of the target reaction.

Lanes not showing visible amounts of the target PCR products but showing visible amounts of the reference system PCR product, indicate that the test sample from which the genomic template DNA was prepared, contained levels of EE-GM3 elite event below the detection limit of the target reaction Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

3. Use of a Specific Integration Fragment as a Probe for Detection of Material Comprising EE-GM3

A specific integration fragment of EE-GM3 is obtained by PCR amplification using specific primers SOY028 (SEQ ID No. 4) and SOY029 (SEQ ID No. 5) yielding an amplicon with the nucleotide sequence of SEQ ID No 8 or by chemical synthesis and is labeled. This integration fragment is used as a specific probe for the detection of EE-GM3 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of EE-GM3 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

4. Protocol for the PCR-Based Determination of the Zygosity Status of EE-GM3 Soybean Plant Material 4.1. Primers Two primers recognizing the nucleotide sequences of the wild-type locus prior to insertion of the elite event, were designed in such a way that they are directed towards each other and have the insertion site of the foreign DNA comprising the herbicide tolerance genes in-between. This set of primers, together with a third primer complementary to foreign DNA sequences and directed towards the flanking DNA, allow simultaneous PCR amplification of the EE-GM3 specific sequence as well as of the wild type sequence.

The following primers were found to give particularly clear and reproducible results in a zygosity scoring PCR reaction on EE-GM3 DNA:

```
                                          (SEQ ID NO.: 6)
SMP187:   5'- ATA.TCA.ACC.CgT.AgC.TCg.AC-3'
          (target: wild type plant DNA upstream of
          3' flanking sequence)

(SEQ ID No.: 5)
SOY029    5'-CAA.ggC.CTC.gAg.ATT.ATC-3'
          (target: plant DNA of the 3' flanking
          sequence)
```

-continued

STV019 5'-ggC.ATT.AAA.TTg.gTg.AAA.ATT.gC-3' (SEQ ID No.: 7)
(target: insert DNA)

4.2. Amplified Fragments

The expected amplified fragments in the PCR reaction are:

For primer pair SMP187-SOY029: 319 bp (wild-type locus)

For primer pair STV019-SOY029: 706 bp (EE-GM3 locus)

4.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 25 or 50 ng of genomic template DNA yields the best results.

4.4. Assigned Positive and Negative Controls

To avoid false positives or negatives, it is advisable that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

4.5. PCR Conditions

Optimal results were obtained under the following conditions. Obviously, other Taq polymerases, such as GO-Taq, can be used, and then the conditions can differ to follow supplier recommendations.

the PCR mix for 25 µl reactions contains:
 x µl template DNA (25 ng)
 2.5 µl 10× Amplification Buffer (supplied by the manufacturer with the Taq polymerase)
 0.5 µl 10 mM dNTP's
 0.5 µl SMP187 (10 pmoles/µl)
 0.5 µl STV019 (10 pmoles/µl)
 1 µl SOY029 (10 pmoles/µl)
 0.1 µl Taq DNA polymerase (5 units/µl) water up to 25 µl the thermocycling profile to be followed for optimal results is the following:
 4 min. at 95° C.
 Followed by: 1 min. at 95° C.
 1 min. at 57° C.
 2 min. at 72° C.
 For 5 cycles
 Followed by: 30 sec. at 92° C.
 30 sec. at 57° C.
 1 min. at 72
 For 25 cycles
 Followed by: 10 minutes at 72° C.

4.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder Pharmacia).

4.7. Validation of the Results

Data from transgenic plant DNA samples within a single PCR run and a single PCR Master Mix will not be acceptable unless:

the positive control shows the expected PCR products (transgenic target amplification)

the wild-type-positive DNA control shows the expected result (wild-type target amplification).

the negative control is negative for PCR amplification (no fragments).

Lanes showing visible amounts of the transgenic PCR product of the expected size and not showing visible amounts of the wild type PCR product, indicate that the corresponding plant from which the genomic DNA template was prepared, is homozygous for the transgenic gene cassette.

Lanes showing visible amounts of the transgenic and wild type PCR products of the expected sizes, indicate that the corresponding plant from which the genomic template DNA was prepared, is hemizygous for the transgenic gene cassette. Lanes not showing visible amounts of the transgenic PCR product and showing visible amounts of the wild type PCR product, indicate that the corresponding plant from which the genomic template DNA was prepared, has not inherited the transgenic sequence assayed for and is thus homozygous for the wild type locus.

Lanes not showing visible amounts of transgenic and wild type PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

Figure 3:
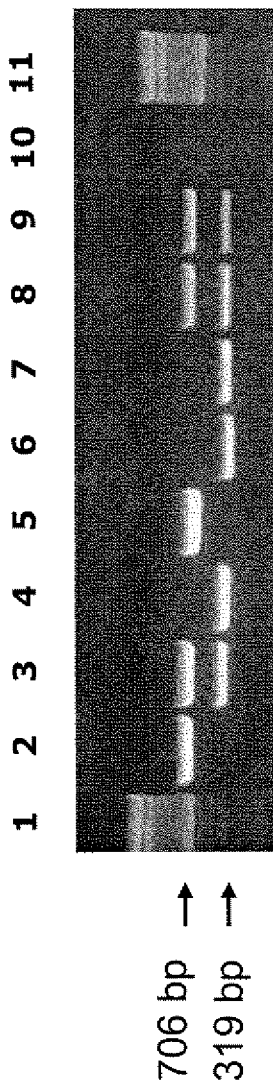
FIG. 3: Results obtained by the zygosity scoring PCR protocol developed for EE-GM3. Loading sequence of the gel: Lane 1: Molecular weight marker (100 bp ladder); lanes 2 and 5: DNA samples from soybean plants comprising the transgenic event EE-GM3 in homozygous form; lanes 3, 8 and 9: DNA samples from soybean plants comprising the transgenic event EE-GM3 in heterozygous form; lanes 4, 6 and 7: control DNA sample from azygous soybean plant; lane 10: no-template DNA control; lane 11: molecular weight marker.

4.8. Use of the Zygosity Scoring Protocol for Identification of Zygosity Status in EE-GM3 Containing Plants FIG. 3 illustrates the result obtained with the zygosity scoring PCR for EE-GM3 on a number of soybean plant samples. The samples in lanes 2 and 5 were found to contain only the PCR fragment (706 bp) characteristic for elite event EE-GM3, while the samples in lanes 4, 6 and 7 contained only the fragment characteristic for the presence of the wt locus. Lanes 3, 8 and 9 contained both fragments. Lanes 2 and 5 therefore contain EE-GM3 in homozygous form, lanes 3, 8 and 9 contain EE-GM3 in hemizygous form and lanes 4, 6 and 7 contain the wt locus in homozygous form (azygous for EE-GM3). Lane 10 represents the negative control (water) sample, and lanes 1 and 11 represent the Molecular Weight Marker (100 bp ladder).

5. Introgression of EE-GM3 into Preferred Cultivars

Elite event EE-GM3 is introduced by repeated back-crossing into commercial soybean cultivars such as but not limited to Soybean Cultivar 7631014 (US2009252860); Soybean Cultivar 7431014 (US2009252859); Soybean Cultivar 7925084 (US2009252858); Soybean Cultivar 7311153 (US2009252857); Soybean Cultivar 5070159 (US2009252856); Soybean Cultivar 7535357 (US2009246353); Soybean Cultivar 5070160 (US2009246352); Soybean Cultivar 26074414 (US2009249508); Soybean Cultivar 7509171

(US2009249507); Soybean Cultivar S070158 (US2009246351); Soybean Cultivar 7511119 (US2009249506); Soybean Cultivar 7113111 (US2009238945); Soybean cultivar S06-02RM018047 (U.S. Pat. No. 7,592,518); Soybean Cultivar 7013345 (US2009232957); Soybean Cultivar 7041461 (US2009235376); Soybean Cultivar 7549450 (US2009232956); Soybean Cultivar 7317090 (US2009232955); Soybean Cultivar 2N2V58015 (US2009226597); Soybean Cultivar 7243182 (US2009226596); Soybean Cultivar 7143182 (US2009226595); Soybean Cultivar 7043182 (US2009220673); Soybean Cultivar S070157 (US2009222950); Soybean Cultivar 306924721 (US2009220672); Soybean Cultivar 7614385 (US2009220671); Soybean Cultivar 7925118 (US2009214750); Soybean Cultivar 7821295 (US2009214749); Soybean Cultivar 7811336 (US2009214748); Soybean Cultivar S070150 (US2009214747); Soybean Cultivar 6214260 (US2009214746); Soybean Cultivar S070152 (US2009214745); Soybean Cultivar 7429331 (US2009214751); Soybean Cultivar 26034631 (US2009208634); Soybean cultivar S07-03JR108674 (U.S. Pat. No. 7,560,621); Soybean cultivar S07-03KL016279 (U.S. Pat. No. 7,560,620); Soybean cultivar S06-CL959411 (U.S. Pat. No. 7,554,017); SOYBEAN CULTIVAR SG3870NRR (US2009158453); SOYBEAN CULTIVAR HFPR-G (CA2645702); Soybean cultivar S06-02JR423016 (U.S. Pat. No. 7,521,606); Soybean cultivar S06-01JR119814 (U.S. Pat. No. 7,518,039); Soybean cultivar S06-01JR119448 (U.S. Pat. No. 7,518,038); Soybean Cultivar 6540220 (US2009055960); Soybean Cultivar 5060292 (US2009055959); Soybean. Cultivar 5050228 (US2009055958); Soybean cultivar S06-02JR423003 (U.S. Pat. No. 7,491,873); Soybean cultivar S06-02JR423005 (U.S. Pat. No. 7,491,872); Soybean cultivar S06-02JR409114 (U.S. Pat. No. 7,485,782); Soybean cultivar S06-SJ144056 (U.S. Pat. No. 7,473,823); Soybean cultivar (U.S. Pat. No. 7,470,835); Soybean cultivar 6910450 (US2008282369); SOYBEAN CULTIVAR 6223012 (U.S. Pat. No. 7,446,246); SOYBEAN CULTIVAR 6549250 (U.S. Pat. No. 7,446,245); Soybean Cultivar 17731225 (US2008271204); Soybean Cultivar 6928285 (US2008271203); Soybean Cultivar 6736054 (US2008271169); Soybean Cultivar S060299 (US2008271199); Soybean Cultivar S060294 (US2008271202); Soybean Cultivar 6943322 (US2008271201); Soybean cultivar 5343260 (US2008263719); Soybean cultivar 6439359 (US2008263704); Soybean cultivar 6238359 (US2008263703); Soybean cultivar 6547272 (US2008263702); Soybean cultivar 6929431 (US2008263701); Soybean cultivar 6703392 (US2008263700); Soybean cultivar 6044483 (US2008263699); Soybean cultivar 5050224 (US2008263698); Soybean cultivar 6719022 (US2008263697); Soybean cultivar 5826056 (US2008263696); Soybean cultivar 6265047 (US2008263724); Soybean cultivar 6928331 (US2008263695); Soybean cultivar 6719331 (US2008263694); Soybean cultivar 6636454 (US2008263693); Soybean cultivar 6226454 (US2008263718); Soybean cultivar Q0073801 (US2008256657); SOYBEAN CULTIVAR 6326393 (US2008256652); SOYBEAN CULTIVAR 6408448 (US2008256651); Soybean cultivar 6449315 (US2008250524); Soybean cultivar S060296 (US2008250523); Soybean cultivar 6012078 (US2008250522); Soybean cultivar 6342078 (US2008250521); Soybean cultivar 6419156 (US2008250520); Soybean cultivar 5723264 (US2008250519); Soybean cultivar S050229 (US2008250518); Soybean cultivar 5060298 (US2008244783); Soybean cultivar 6935331 (US2008244782); Soybean cultivar 6819456 (US2008244787); Soybean cultivar S050229 (US2008244781); Soybean cultivar 6135319 (US2008244786); Soybean cultivar 6819331 (US2008244780); Soybean cultivar 6137445 (US2008244779); Soybean cultivar 6917445 (US2008244778); Soybean cultivar 6111333 (US2008244777); Soybean Cultivar S050229 (US2008244776); Soybean Cultivar 6114011 (US2008244775); Soybean Cultivar 6900358 (US2008244784); Soybean Cultivar 6345184 (US2008244774); Soybean Cultivar 6836085 (US2008244773); Soybean Cultivar 6635047 (US2008244772); Soybean Cultivar 6139105 (US2008244771); SOYBEAN CULTIVAR 6434385 (US2008244770); SOYBEAN CULTIVAR S060295 (US2008244769); Soybean Cultivar 6035184 (US2008244768); Soybean Cultivar S060293 (US2008209590); Soybean Cultivar 6733322 (US2008209594); SOYBEAN CULTIVAR 6421326 (US2008209593); Soybean Cultivar 5060077 (US2008209589); SOYBEAN CULTIVAR 6600375 (US2008209592); Soybean cultivar S06-CL821457 (U.S. Pat. No. 7,420,104); Soybean cultivar S07-02KG294306 (U.S. Pat. No. 7,414,178); Soybean cultivar S06-BA046119 (U.S. Pat. No. 7,414,175); Soybean cultivar S07-02KG294307 (U.S. Pat. No. 7,411,114); Soybean Cultivar SG3865N (US2008189802); Soybean cultivar 6701475 (U.S. Pat. No. 7,408,097); Soybean Cultivar 1335025 (US2008178316); Soybean Cultivar 1686017 (US2008178315); Soybean Cultivar 2388028 (US2008178314); Soybean Cultivar 2387029 (US2008178313); Soybean cultivar S06-WW152330 (U.S. Pat. No. 7,388,129); Soybean cultivar 6424090 (U.S. Pat. No. 7,385,118); Soybean cultivar 6723322 (U.S. Pat. No. 7,385,115); Soybean cultivar SG4377NRR (U.S. Pat. No. 7,385,114); Soybean cultivar S06-02JR111334 (U.S. Pat. No. 7,381,864); Soybean cultivar 6141287 (U.S. Pat. No. 7,378,577); Soybean cultivar MT110501 (U.S. Pat. No. 7,378,576); Soybean cultivar (U.S. Pat. No. 7,378,575); Soybean cultivar S06-WW169267 (U.S. Pat. No. 7,375,261); Soybean cultivar 6223392 (U.S. Pat. No. 7,371,939); Soybean cultivar S06-CL968413 (U.S. Pat. No. 7,371,937); Soybean cultivar S06-CL951107 (U.S. Pat. No. 7,368,636); Soybean cultivar S06-MT9152077 (U.S. Pat. No. 7,361,810); Soybean Cultivar 4211676 (US2008092253); Soybean cultivar S06-M059029 (U.S. Pat. No. 7,355,101); Soybean Cultivar 6548193 (U.S. Pat. No. 7,345,228); Soybean cultivar 6440261 (U.S. Pat. No. 7,345,227); Soybean cultivar S060291 (U.S. Pat. No. 7,342,151); Soybean cultivar S06-MT9206166 (U.S. Pat. No. 7,339,094); Soybean cultivar S06-WW013107 (U.S. Pat. No. 7,339,093); Soybean cultivar S06-M03256 (U.S. Pat. No. 7,335,820); Soybean cultivar 6134466 (U.S. Pat. No. 7,332,656); Soybean cultivar S06-01JR123373 (U.S. Pat. No. 7,329,800); Soybean cultivar S06-MT9211059 (U.S. Pat. No. 7,326,831); Soybean cultivar 26170838 (US2008016590); Soybean cultivar 306612412 (US2008016588); Soybean cultivar 26660135 (US2008016587); Soybean cultivar 306734323

(US2008016586); Soybean cultivar S06-01M122235 (U.S. Pat. No. 7,317,144); SOYBEAN CULTIVAR 5900450 (U.S. Pat. No. 7,314,986); Soybean cultivar S06-MT116260 (U.S. Pat. No. 7,314,984); Soybean cultivar S06-SJ143606 (U.S. Pat. No. 7,312,381); Soybean cultivar S06-98181-G01-35167 (U.S. Pat. No. 7,309,819); SOYBEAN CULTIVAR 26082635 (U.S. Pat. No. 7,304,219); Soybean cultivar BA922834 (U.S. Pat. No. 7,304,217); Soybean cultivar 01JR123480 (U.S. Pat. No. 7,304,216); Soybean cultivar M061422 (U.S. Pat. No. 7,304,215); Soybean cultivar 17082821 (US2007277262); Soybean cultivar 17621620 (US2007277261); Soybean cultivar 00977706 (US2007277260); Soybean cultivar 5060182 (US2007277259); Soybean cultivar 26312034 (U.S. Pat. No. 7,301,078); Soybean cultivar 26143837 (U.S. Pat. No. 7,301,077); Soybean cultivar 435.TCS (US2007271626); Soybean cultivar 495.RC (US2007271625); Soybean cultivar 5306230 (U.S. Pat. No. 7,297,845); Soybean cultivar S06-WW167686 (U.S. Pat. No. 7,291,772); Soybean cultivar 6141145 (US2007245426); Soybean cultivar 5050232 (US2007226829); Soybean cultivar 5333301 (US2007226828); SOYBEAN CULTIVAR 5050215 (US2007226827); SOYBEAN CULTIVAR 3235020 (US2007226826); Soybean cultivar 5720482 (US2007226825); Soybean cultivar 5050216 (US2007226824); Soybean Cultivar 5512112 (US2007226823); Soybean cultivar 3233021 (US2007226822); SOYBEAN CULTIVAR 1336024 (US2007226821); Soybean cultivar 5348287 (US2007226820); Soybean cultivar 5204220 (US2007226819); Soybean cultivar 6188027 (US2007226818); Soybean cultivar 4183026 (US2007226817); Soybean cultivar S06-WW157958 (U.S. Pat. No. 7,271,325); Soybean cultivar 5733056 (US2007209091); Soybean cultivar 90501911 (US2007209090); Soybean cultivar 5050221 (US2007204361); SOYBEAN CULTIVAR 5802205 (US2007204360); Soybean cultivar 1000642 (US2007204359); Soybean cultivar 5420128 (US2007204358); Soybean cultivar 5050222 (US2007199094); Soybean cultivar 5050217 (US2007199093); SOYBEAN CULTIVAR 5050223 (US2007199092); Soybean cultivar 5050218 (US2007199091); Soybean cultivar 5419227 (US2007199089); Soybean cultivar 5319227 (US2007199088); Soybean cultivar 5723045 (US2007199087); SOYBEAN CULTIVAR 5051007 (US2007199086); Soybean cultivar 5826175 (US2007192893); Soybean cultivar S050231 (US2007192892); SOYBEAN CULTIVAR 5826376 (US2007192891); SOYBEAN CULTIVAR 5628386 (US2007192890); Soybean cultivar 5138236 (US2007186307); Soybean cultivar 5608398 (US2007186306); SOYBEAN CULTIVAR S050230 (US2007186305); SOYBEAN CULTIVAR 5624126 (US2007180561); SOYBEAN CULTIVAR 5019225 (US2007180560); SOYBEAN CULTIVAR 5549483 (US2007180559); SOYBEAN CULTIVAR 4189010 (US2007180551); SOYBEAN CULTIVAR 1486018 (US2007180550); SOYBEAN CULTIVAR S050235 (US2007180549); SOYBEAN CULTIVAR 5023230 (US2007180548); SOYBEAN CULTIVAR 5050238 (US2007174930); SOYBEAN CULTIVAR 5830261 (US2007174928); SOYBEAN CULTIVAR S050226 (U.S. Pat. No. 7,247,772); SOYBEAN CULTIVAR 5806063 (U.S. Pat. No. 7,247,771); SOYBEAN CULTIVAR S050233 (U.S. Pat. No. 7,244,881); SOYBEAN CULTIVAR 5726085 (U.S. Pat. No. 7,241,939); Soybean cultivar MT000792 (U.S. Pat. No. 7,238,867); Soybean cultivar 5521161 (U.S. Pat. No. 7,235,718); Soybean cultivar WW109447 (U.S. Pat. No. 7,235,717); Soybean cultivar BA947474 (U.S. Pat. No. 7,220,898); Soybean cultivar 5939002 (U.S. Pat. No. 7,217,870); Soybean cultivar 5726175 (U.S. Pat. No. 7,217,869); Soybean cultivar 5432082 (U.S. Pat. No. 7,217,868); Soybean cultivar SG0850RR (U.S. Pat. No. 7,211,715); Soybean cultivar SG1750NRR (U.S. Pat. No. 7,208,658); Soybean cultivar MT017827 (U.S. Pat. No. 7,208,657); Soybean cultivar 4N2V74028 (U.S. Pat. No. 7,205,458); Soybean cultivar CL431203 (U.S. Pat. No. 7,202,400); Soybean cultivar 4N0S63222 (U.S. Pat. No. 7,199,288); Soybean cultivar 5520279 (U.S. Pat. No. 7,196,253); Soybean cultivar 5834401 (U.S. Pat. No. 7,196,252); Soybean cultivar 5621161 (U.S. Pat. No. 7,196,251); Soybean cultivar CL722114 (U.S. Pat. No. 7,196,250); Soybean cultivar 5741081 (U.S. Pat. No. 7,193,140); Soybean cultivar CL727422 (U.S. Pat. No. 7,186,895); Soybean cultivar 4N2V55022 (U.S. Pat. No. 7,183,468); Soybean cultivar 5083011 (U.S. Pat. No. 7,173,169); Soybean cultivar 5626085 (U.S. Pat. No. 7,169,976); SOYBEAN CULTIVAR S050051 (U.S. Pat. No. 7,169,974); SOYBEAN CULTIVAR 4506816 (US2006294626); Soybean cultivar WW152201 (U.S. Pat. No. 7,132,594); Soybean cultivar CL727636 (U.S. Pat. No. 7,132,593); Soybean cultivar M08851 (U.S. Pat. No. 7,126,047); Soybean cultivar 4324401 (U.S. Pat. No. 7,105,728); Soybean cultivar 5050164 (U.S. Pat. No. 7,105,727); Soybean cultivar 4136015 (US2006195931); Soybean cultivar 3133014 (US2006195930); Soybean cultivar 5040132 (US2006195929); Soybean Cultivar 4328386 (US2006195928); Soybean cultivar 1339013 (US2006195927); SOYBEAN CULTIVAR 4423183 (US2006195925); Soybean cultivar 5040131 (US2006195924); Soybean cultivar 4929388 (US2006195923); Soybean cultivar 4817034 (US2006195922); Soybean cultivar 4916816 (U.S. Pat. No. 7,098,385); Soybean cultivar 4713487 (US2006191032); Soybean cultivar 4348019 (US2006191031); Soybean cultivar S040122 (US2006191030); Soybean cultivar S040133 (US2006185031); Soybean cultivar CL821418 (U.S. Pat. No. 7,091,404); SOYBEAN CULTIVAR 4441080 (U.S. Pat. No. 7,091,403); Soybean cultivar 4805442 (US2006179509); Soybean cultivar 4921237 (US2006179508); Soybean cultivar 4117380 (US2006174369); Soybean cultivar 4405070 (US2006174368); Soybean cultivar 4417779 (U.S. Pat. No. 7,084,328); Soybean cultivar 5040125 (US2006168678); Soybean cultivar 4909380 (U.S. Pat. No. 7,081,572); Soybean cultivar 5050162 (U.S. Pat. No. 7,081,571); Soybean cultivar 6084016 (U.S. Pat. No. 7,081,570); Soybean cultivar 5050163 (U.S. Pat. No. 7,078,600); Soybean cultivar 5040135 (U.S. Pat. No. 7,078,598); Soybean cultivar 5040117 (U.S. Pat. No. 7,078,597); Soybean cultivar M03393 (U.S. Pat. No. 7,071,391); Soybean cultivar 4145306 (U.S. Pat. No. 7,064,253); Soybean cultivar 900213 (US2006117405); Soybean cultivar 1000126 (US2006117404); Soybean cultivar 901023 (US2006117403); Soybean cultivar 5040130 (U.S. Pat. No. 7,053,280); Soybean cultivar 4706198 (U.S. Pat. No. 7,053,279); Soybean cultivar 5040118 (U.S. Pat. No. 7,053,278); Soybean cultivar S040119 (U.S. Pat. No. 7,053,277); Soybean cultivar 5040123 (U.S. Pat. No. 7,053,276); Soybean cultivar S040124 (U.S. Pat. No. 7,049,497); SOYBEAN CULTIVAR 917013 (U.S. Pat. No. 7,045,689); Soybean cultivar S04124 (U.S. Pat. No. 7,045,691); Soybean cultivar 4238491 (U.S. Pat. No. 7,045,690); Soybean cultivar 5010136 (U.S. Pat. No. 7,041,882); Soybean cultivar 900613 (U.S. Pat. No. 7,030,297); Soybean cultivar 4337175 (U.S. Pat. No. 7,030,301); Soybean cultivar 5040121 (U.S. Pat. No. 7,030,300); Soybean cultivar 4216033 (U.S. Pat. No. 7,030,299); Soybean cultivar 5040128 (U.S. Pat. No. 7,022,901); Soybean cultivar 5040120 (U.S. Pat. No. 7,022,900); Soybean cultivar S040127 (U.S. Pat. No. 7,019,199); Soybean cultivar 5040134 (U.S. Pat. No. 7,015,378); Soybean cultivar 5040129 (U.S. Pat. No. 7,015,377); Soybean cultivar 4513420 (U.S. Pat. No. 7,005,564); Soybean cultivar 943013 (US2006031958); Soybean cultivar 5030136 (US2006021081); Soybean cultivar 927013 (US2006021080); Soybean cultivar 1000109 (US2006015962); Soybean cultivar 90046112 (US2006010530); Soybean cultivar 90897327 (US2006010529); Soybean cultivar 90362421 (US2006010528); Soybean cultivar 03022253 (US2006010527); Soybean cultivar 02022433 (US2006010526); Soybean cultivar 02022323 (US2006010525); Soybean cultivar 02912951 (US2006010524); Soybean cultivar 0102115 (US2006010523); Soybean cultivar 915034 (US2006010522); Soybean cultivar 0509255 (US2006010521); Soybean cultivar 4803070 (U.S. Pat. No. 6,982,368); Soybean cultivar 4704310 (U.S. Pat. No. 6,979,762); Soybean cultivar 53919784 (US2005268362); Soybean cultivar CL615261 (US2005268361); Novel soybean (US2004199964); Soybean cultivar 0509214 (US2005210542); Soybean cultivar 70826751 (US2005193442); Soybean cultivar 0509243 (US2005193441); Soybean cultivar 0509246 (US2005193440); Soybean cultivar 0509253 (US2005193439); Soybean cultivar 0509247 (US2005193438); Soybean cultivar 0509252 (US2005193437); Soybean cultivar 0509241 (US2005193436); Soybean cultivar 0509249 (U.S. Pat. No. 6,884,927); Soybean cultivar 0509244 (US2005183158); Soybean cultivar 0509240 (US2005183157); Soybean cultivar 0509239 (US2005183156); Soybean cultivar 0509254 (US2005183155); Soybean cultivar 0509245 (US2005183154); Soybean cultivar 0509251 (US2005183153); Soybean cultivar 4283008 (U.S. Pat. No. 6,888,050); Soybean cultivar 2386009 (US2005183152); Soybean cultivar 3282002 (U.S. Pat. No. 6,870,080); Soybean cultivar 0509248 to (US2005183151); Soybean cultivar 5091007 (U.S. Pat. No. 6,906,249); Soybean cultivar 0509236 (US2005166281); Soybean cultivar 0509235 (US2005166280); Soybean cultivar 0509237 (US2005166279); Soybean cultivar SG5322NRR (US2005164390); Soybean cultivar SG5030NRR (US2005166278); Soybean cultivar SG4911NRR (US2005166277); Soybean cultivar S03153 (US2005160504); Soybean cultivar 5030158 (US2005144680); SOYBEAN CULTIVAR 5030160 (US2005144679); Soybean cultivar 5030161 (US2005144678); Soybean cultivar 5030157 (US2005144677); Soybean cultivar 5030155 (US2005144676); Soybean cultivar 5030156 (US2005144675); SOYBEAN CULTIVAR S030159 (US2005144674); Soybean cultivar 5030154 (U.S. Pat. No. 6,900,376); Soybean cultivar 5020030 (US2005114929); Soybean cultivar 5030010 (US2005114928); Soybean cultivar SG1431RR (US2005097629); SOYBEAN CULTIVAR SG1330NRR (US2005097642); Soybean cultivar 5030150 (US2005071900); SOYBEAN CULTIVAR 5022209 (US2005050601); Soybean cultivar 5022217 (US2005050600); Soybean cultivar 5022219 (US2005050599); Soybean cultivar 5030151 (US2005050598); Soybean cultivar 0491735 (US2005022272); Soybean cultivar 5022218 (US2005022271); Soybean cultivar 6190006 (US2004268447); Soybean cultivar SG1120RR (US2004250316); Soybean cultivar 0487681 (US2004237153); Soybean cultivar 0491717 (US2004237152); Soybean cultivar 5022220 (US2004237151); Soybean cultivar 0491715 (US2004237150); Soybean cultivar 0491712 (US2004237149); Soybean cultivar 0491718 (US2004237148); Soybean cultivar 99271316 (US2004221344); Soybean cultivar 5022212 (US2004221343); Soybean cultivar 0491737 (US2004221342); Soybean cultivar S022211 (US2004221341); Soybean cultivar S022210 (US2004221340); Soybean cultivar 5022213 (US2004221339); Soybean cultivar 0491725 (US2004221346); Soybean cultivar 03129016 (US2004221329); Soybean cultivar 5022208 (US2004221328); Soybean cultivar 5022207 (US2004221345); Soybean cultivar 02932 (US2004210968); Soybean cultivar 94137321 (US2004205862); Soybean cultivar 94106224 (US2004205861); Soybean cultivar 94143901 (US2004205859); SOYBEAN CULTIVAR 0487685 (US2004205858); SOYBEAN CULTIVAR 92440927 (US2004205857); Soybean cultivar 0487686 (US2004205856); Soybean cultivar 5022215 (US2004205855); Soybean cultivar 5022214 (US2004205854); SOYBEAN CULTIVAR 0491726 (US2004205849); SOYBEAN CULTIVAR 92478609 (US2004205853); Soybean cultivar 922013 (U.S. Pat. No. 6,781,040); SOYBEAN CULTIVAR 0491727 (US2004205852); SOYBEAN CULTIVAR 0491728 (US2004205851); Soybean cultivar 1465003 in (US2004098766); Soybean cultivar 3186004 (US2004019936); Soybean cultivar 7085005 (US2004205850); Soybean cultivar 5022204 (US2004199958); Soybean cultivar 5022206 (US2004199957); Soybean cultivar 0491731 (US2004199956); Soybean cultivar 0491733 (US2004199955); Soybean cultivar 0491738 (US2004199954); Soybean cultivar 0491732 (US2004199953); Soybean cultivar 0491729 (US2004199952); Soybean cultivar 5020011 (US2004199951); Soybean cultivar 0491739 (US2004199950); Soybean cultivar 0491730 (US2004199949); Soybean cultivar 13873 (US2004199948); Soybean cultivar 954011 (US2004181822); Soybean cultivar 010022 (US2004181831); Soybean cultivar 4181001 (US2003229926); Soybean cultivar 0491721 (US2004168228); Soybean cultivar 0491723 (U.S. Pat. No. 6,911,581); Soybean cultivar 0491716 (US2004168226); Soybean cultivar 0491713 (US2004168225); Soybean cultivar 0491711 (US2004168224); Soybean cultivar 0491722 (US2004168223); Soybean cultivar 0491724 (US2004168222); Soybean cultivar 0491720 (US2004168221); Soybean cultivar 0487682 (US2004168220); Soybean cultivar 0491714 (US2004168219); Soybean cultivar 0491719 (US2004168218); Soybean cultivar DP 5634 RR (US2003177540); Soybean Cultivar S56-D7 (US2004098765); Soybean cultivar 926877

| | | | |
|---|---|---|---|
| (US2004064859); | Soybean | cultivar | SE73753 |
| (US2004055059); | Soybean | cultivar | SN83594 |
| (US2004055058); | Soybean | cultivar | SE71112 |
| (US2004055056); | Soybean | cultivar | SE73090 |
| (US2004055054); | Soybean | cultivar | SN79526 |
| (US2004055053); | Soybean | cultivar | SW90702 |
| (US2004055052); | Soybean | cultivar | SN79525 |
| (US2004055051); | Soybean | cultivar | SE90345 |
| (US2004055050); | Soybean | cultivar | 0149928 |
| (US2004055049); | Soybean | cultivar | SN83780 |
| (US2004055048); | Soybean | cultivar | 0053840 |
| (US2004055047); | Soybean | cultivar | 924001 |
| (US2004055046); | Soybean | cultivar | 0004747 |
| (US2004055057); | Soybean | cultivar | 0037357 |
| (US2004055045); | Soybean | cultivar | SN83366 |
| (US2004055044); | Soybean | cultivar | SN76208 |
| (US2004055043); | Soybean | cultivar | 0037370 |
| (US2004055042); | Soybean | cultivar | SX95512 |
| (US2004049821); | Soybean | cultivar | 0096008 |
| (US2004049820); | Soybean | cultivar | SN83544 |
| (US2004049819); | Soybean | cultivar | 0088401 |
| (US2004049818); | Soybean | cultivar | SN64195 |
| (US2004049817); | Soybean | cultivar | 0034754 |
| (US2004049816); | Soybean | cultivar | SN71173 |
| (US2004049815); | Soybean | cultivar | SN83211 |
| (US2004049814); | Soybean | cultivar | 92422749 |
| (US2004045058); | Soybean | cultivar | 0120311 |
| (US2004045057); | Soybean | cultivar | S010344 |
| (US2004003438); | Soybean | cultivar | 70876922 |
| (US2004003437); | Soybean | cultivar | 924496 |
| (US2004003436); | Soybean | cultivar | 19705120 |
| (US2003237116); | Soybean | cultivar | 19704220 |
| (US2003235914); | Soybean | Cultivar | 19704280 |
| (US2003237115); | Soybean | cultivar | 19704210 |
| (US2003237114); | Soybean | cultivar | S37-N4 |
| (US2003237113); | Soybean | cultivar | 19602310 |
| (US2003233685); | Soybean | cultivar | 19704120 |
| (US2003233684); | Soybean | cultivar | 19704230 |
| (US2003233683); | Soybean | cultivar | 1000126 |
| (US2003233682); | Soybean | cultivar | 93831526 |
| (US2003221226); | Soybean | cultivar | 0322581 |
| (US2003221225); | Soybean | cultivar | 0332149 |
| (US2003213028); | Soybean | cultivar | 0332144 |
| (US2003213027); | Soybean | cultivar | 924788 |
| (US2003213026); | Soybean | cultivar | 924861 |
| (US2003213025); | Soybean | cultivar | 928070 |
| (US2003213024); | Soybean | cultivar | 5010354 |
| (US2003213023); | Soybean | cultivar | 5010360 |
| (US2003213022); | Soybean | cultivar | S010361 |
| (US2003213021); | Soybean | cultivar | S010363 |
| (US2003213020); | Soybean | cultivar | 5010364 |
| (US2003213019); | Soybean | cultivar | 0332148 |
| (US2003208805); | Soybean | cultivar | 0332147 |
| (US2003208804); | Soybean | cultivar | 0332146 |
| (US2003208803); | Soybean | cultivar | 0332135 |
| (US2003208802); | Soybean | cultivar | 1000144 |
| (US2003208801); | Soybean | cultivar | 0332143 |
| (US2003208800); | Soybean | cultivar | 0332145 |
| (US2003208799); | Soybean | cultivar | 5010345 |
| (US2003204884); | Soybean | cultivar | 0332131 |
| (US2003204883); | Soybean | cultivar | 0332130 |
| (US2003204882); | Soybean | cultivar | 0332129 |
| (US2003204881); | Soybean | cultivar | 0332122 |
| (US2003204880); | Soybean | cultivar | 5010350 |
| (US2003204879); | Soybean | cultivar | 5010355 |
| (US2003204878); | Soybean | cultivar | 031766 |
| (US2003204877); | Soybean | cultivar | 5010353 |
| (US2003204876); | Soybean | cultivar | 0322580 |
| (US2003200579); | Soybean | cultivar | 0322579 |
| (US2003200578); | Soybean | cultivar | 5010347 |
| (US2003200577); | Soybean | cultivar | 5010349 |
| (US2003200576); | Soybean | cultivar | 0332141 |
| (US2003200575); | Soybean | cultivar | 0332142 |
| (US2003200574); | Soybean | Cultivar | 0332133 |
| (US2003200573); | Soybean | cultivar | 0332134 |
| (US2003200572); | Soybean | cultivar | 0332139 |
| (US2003200571); | Soybean | cultivar | 0332137 |

(US2003200570); Soybean variety XB33U08 (U.S. Pat. No. 7,598,435); Soybean variety XB27D08 (U.S. Pat. No. 7,592,519); Soybean variety XB41M08 (U.S. Pat. No. 7,589,261); Soybean variety XB05308 (U.S. Pat. No. 7,589,260); Soybean variety XB33T08 (U.S. Pat. No. 7,589,259); Soybean variety XB30Y08 (U.S. Pat. No. 7,586,025); Soybean variety XB40U08 (U.S. Pat. No. 7,582,813); Soybean variety XB29M08 (U.S. Pat. No. 7,582,811); SOYBEAN VARIETY 93Y10 (US2009144843); SOYBEAN VARIETY D4325666 (US2009055957); SOYBEAN VARIETY D4125897 (US2009055956); SOYBEAN VARIETY D4698573 (US2009055955); SOYBEAN VARIETY D4356652 (US2009019592); SOYBEAN VARIETY D4456885 (US2009019591); SOYBEAN VARIETY D4698013 (US2009019590); SOYBEAN VARIETY D4637114 (US2009019589); SOYBEAN VARIETY D4102367 (US2009019595); SOYBEAN VARIETY D4266582 (US2009019594); SOYBEAN VARIETY D4422801 (US2009019593); SOYBEAN VARIETY D4520980 (US2009019588); SOYBEAN VARIETY D4521369 (US2009019587); SOYBEAN VARIETY D4223057 (U52009019586); SOYBEAN VARIETY D4682156 (US2009019585); SOYBEAN VARIETY D4233569 (US2009019584); SOYBEAN VARIETY D4925614 (US2009019583); SOYBEAN VARIETY D4203144 (US2009019604); SOYBEAN VARIETY D4102536 (US2009019582); SOYBEAN VARIETY D4865324 (US2009019581); SOYBEAN VARIETY D4825495 (US2009019580); SOYBEAN VARIETY D4659251 (US2009019579); SOYBEAN VARIETY D4258962 (US2009019578); SOYBEAN VARIETY D4253969 (US2009019577); SOYBEAN VARIETY D4696658 (US2009019603); SOYBEAN VARIETY D4256925 (US2009019576); SOYBEAN VARIETY D4253681 (US2009019575); SOYBEAN VARIETY D4789254 (US2009019574); SOYBEAN VARIETY D4713125 (US2009019573); SOYBEAN VARIETY D4526223 (US2009019572); SOYBEAN VARIETY D4556201 (US2009019571); SOYBEAN VARIETY D4012368 (US2009019570); SOYBEAN VARIETY D4452019 (US2009019569); SOYBEAN VARIETY D4201483 (US2009019568); SOYBEAN VARIETY D4463892 (US2009019567); SOYBEAN VARIETY D4159630 (US2009019566); SOYBEAN VARIETY D4470236 (US2009019565); SOYBEAN VARIETY D4063284 (US2009019564); SOYBEAN VARIETY D4021792 (US2009013429); SOYBEAN VARIETY D4902530 (US2009013428); SOYBEAN VARIETY D4367012 (US2009013427); SOYBEAN VARIETY D4923560 (US2009013426); SOYBEAN VARIETY D4253854 (US2009013425); SOYBEAN VARIETY D4210110 (US2009007290); SOYBEAN VARIETY D4523081 (US2009007289); SOYBEAN VARIETY D4328762 (US2009007288); SOYBEAN VARIETY D4483789 (US2009007287); SOYBEAN VARIETY D4311702 (US2009007286); SOYBEAN VARIETY D4127789 (US2008313765); SOYBEAN VARIETY D4361423 (US2008313764); SOYBEAN VARIETY D4208814 (US2008313763); SOYBEAN VARIETY D4201139 (US2008313762); SOYBEAN VARIETY D4120384 (US2008313761); SOYBEAN VARIETY D4572906 (US2008313760); SOYBEAN VARIETY D4301279 (US2008313759); SOYBEAN VARIETY D4422957 (US2008313758); SOYBEAN VARIETY D4256958 (US2008313757); SOYBEAN VARIETY 4074328 (US2008282366); SOYBEAN VARIETY XB47Q06 (US2008244767); SOYBEAN VARIETY XB26R06 (US2008244766); SOYBEAN VARIETY 4991629 (US2008216190); SOYBEAN VARIETY 4158090 (US2008216189); Soybean Variety XB40K07 (US2008209582); SOYBEAN VARIETY D0069201 (US2008178345); SOYBEAN VARIETY D0064801 (US2008178320); SOYBEAN VARIETY D0063801 (US2008178344); SOYBEAN VARIETY D0061501 (US2008178343); SOYBEAN VARIETY 4938051 (US2008178319); SOYBEAN VARIETY 4880500 (US2008178318); SOYBEAN VARIETY 4835953 (US2008178317); SOYBEAN VARIETY 4684181 (US2008178342); SOYBEAN VARIETY 4427363 (US2008178340); SOYBEAN VARIETY 4676311 (US2008178339); SOYBEAN VARIETY 4953710 (US2008178337); SOYBEAN VARIETY 4857548 (US2008178336); SOYBEAN VARIETY 4551757 (US2008178335); SOYBEAN VARIETY 4027271 (US2008178334); SOYBEAN VARIETY 4274171 (US2008178333); SOYBEAN VARIETY 0341931 (US2008178332); SOYBEAN VARIETY 4282159 (US2008178331); SOYBEAN VARIETY 4852004 (US2008178330); SOYBEAN VARIETY 4688589 (US2008178329); SOYBEAN VARIETY 4614131 (US2008178327); SOYBEAN VARIETY 4201823 (US2008178326); SOYBEAN VARIETY 92M22 (US2008178350); SOYBEAN VARIETY 4174206 (US2008178322); SOYBEAN VARIETY 4305498 (US2008178321); SOYBEAN VARIETY 4423586 (US2008172761); SOYBEAN VARIETY 4568207 (US2008172756); SOYBEAN VARIETY 4840308 (US2008172755); SOYBEAN VARIETY 4256323 (US2008172754); SOYBEAN VARIETY 4789516 (U.S. Pat. No. 7,399,907); SOYBEAN VARIETY 90Y40 (US2008168581); SOYBEAN VARIETY 4959932 (U.S. Pat. No. 7,396,983); SOYBEAN VARIETY 4062885 (U.S. Pat. No. 7,394,000); Soybean variety 4858197 (U.S. Pat. No. 7,390,940); Soybean variety 4092390 (U.S. Pat. No. 7,390,939); Soybean variety 4735486 (U.S. Pat. No. 7,390,938); Soybean variety 4219527 (U.S. Pat. No. 7,388,132); Soybean variety 4599695 (U.S. Pat. No. 7,388,131); Soybean variety 4554257 (U.S. Pat. No. 7,388,130); Soybean variety 4896902 (U.S. Pat. No. 7,385,113); Soybean variety 4367308 (U.S. Pat. No. 7,385,112); Soybean variety 4589609 (U.S. Pat. No. 7,385,111); Soybean variety 4640250 (U.S. Pat. No. 7,385,110); Soybean variety 4540394 (U.S. Pat. No. 7,385,109); Soybean variety 4297661 (U.S. Pat. No. 7,385,108); Soybean variety 4958786 (U.S. Pat. No. 7,381,866); Soybean variety 4440685 (U.S. Pat. No. 7,375,262); Soybean variety 4008211 (U.S. Pat. No. 7,371,938); Soybean variety 4778469 (U.S. Pat. No. 7,368,637); Soybean variety 4766295 (US7355103); Soybean variety 4436909 (U.S. Pat. No. 7,355,102); Soybean variety 4812469 (U.S. Pat. No. 7,351,886); Soybean variety 4761767 (U.S. Pat. No. 7,351,885); Soybean variety 4142393 (U.S. Pat. No. 7,329,801); Soybean variety 4502135 (U.S. Pat. No. 7,326,832); Soybean variety 4353363 (U.S. Pat. No. 7,321,082); Soybean variety 91B42 (U.S. Pat. No. 7,317,143); SOYBEAN VARIETY 0330739 (US2007271622); Soybean variety 0384279 (U.S. Pat. No. 7,294,768); SOYBEAN VARIETY 4175567 (US2007256187); SOYBEAN VARIETY 4336643 (US2007256186); SOYBEAN VARIETY 4671685 (US2007256185); SOYBEAN VARIETY 4309194 (US2007256190); SOYBEAN VARIETY 0330738 (US2007256184); SOYBEAN VARIETY 0045477 (US2007256183); SOYBEAN VARIETY 0437973 (US2007256182); SOYBEAN VARIETY 0457028 (US2007256181); SOYBEAN VARIETY 0367478 (US2007256180); SOYBEAN VARIETY 0358232 (US2007256179); SOYBEAN VARIETY 0417158 (US2007256178); SOYBEAN VARIETY 4559809 (US2007256177); SOYBEAN VARIETY 0196172 (US2007256176); SOYBEAN VARIETY 4785923 (US2007256175); SOYBEAN VARIETY 4587513 (US2007256174); SOYBEAN VARIETY 0409670 (US2007256173); SOYBEAN VARIETY 4010165 (US2007256172); SOYBEAN VARIETY 0421133 (US2007256171); SOYBEAN VARIETY 0240187 (US2007256170); SOYBEAN VARIETY 0387907 (US2007256169); SOYBEAN VARIETY 0232405 (US2007256168); SOYBEAN VARIETY 0146529 (US2007256167); SOYBEAN VARIETY 4788561 (US2007256166); SOYBEAN VARIETY 457114 (US2007256165); SOYBEAN VARIETY 0149217 (US2007256164); SOYBEAN VARIETY 4247825 (US2007254366); SOYBEAN VARIETY 0212938 (US2007256163); SOYBEAN VARIETY 0146565 (US2007256162); SOYBEAN VARIETY 4647672 (US2007256161); SOYBEAN VARIETY 0215818 (US2007256160); SOYBEAN VARIETY 0384531 (US2007256159); SOYBEAN VARIETY 4878185 (US2007254365); SOYBEAN VARIETY 4498438 (US2007256158); SOYBEAN VARIETY 0436052 (US2007256157); SOYBEAN VARIETY 4782157 (US2007256156); SOYBEAN VARIETY 0385457 (US2007256155); SOYBEAN VARIETY 0385240 (US2007256154); SOYBEAN VARIETY 4735316 (US2007256153); SOYBEAN VARIETY 0277524 (US2007256152); SOYBEAN VARIETY 0276951 (US2007256151); Soybean Variety XB37L07 (US2007245429); Soybean Variety XB35X07 (US2007226837); Soybean Variety XB35S07 (US2007226836); Soybean Variety XB35F07 (US2007226835); Soybean Variety XB34R07 (US2007226834); Soybean Variety XB34L07 (US2007226833); Soybean Variety XB34D07 (US2007226832); Soybean Variety XB33G07 (US2007226831); Soybean Variety 98Y11 (US2007169220); Soybean variety 0137335 (U.S. Pat. No. 7,241,941); Soybean Variety XB15E07 (US2007150980); Soybean Variety 92M52 (US2007150979); Soybean Variety XB47R07 (US2007136888); Soybean Variety XB46V07 (US2007136887); Soybean Variety XB57E07 (US2007136886); Soybean Variety XB54X07 (US2007136885); Soybean Variety XB54V07 (US2007136884); Soybean Variety XB52Q07 (US2007136883); Soybean Variety XB37M07 (US2007136882); Soybean Variety XB37J07 (US2007136881); Soybean Variety XB34Q07 (US2007136880); Soybean Variety XB32S07 (US2007136879); Soybean Variety XB32J07 (US2007136878); Soybean Variety XB31R07 (US2007136877); Soybean Variety XB31J07 (US2007136876); Soybean Variety XB29K07

(US2007136875); Soybean Variety XB31H07 (US2006107383); Soybean variety XB29R06
(US2007136874); Soybean Variety XB30G07 (US2006107382); Soybean variety XB16S06
(US2007136873); Soybean Variety XB30E07 (US2006107381); Soybean variety XB36V06
(US2007136872); Soybean Variety XB25E07 (US2006107380); Soybean variety XB07N06
(US2007136871); Soybean Variety XB26X07 (US2006107379); Soybean variety XB23H06
(US2007136870); Soybean Variety XB23L07 (US2006107378); Soybean variety XB35C06
(US2007136869); Soybean Variety XB19Z07 (US2006107377); Soybean variety XB32L06
(US2007136868); Soybean Variety X819E07 (US2006107376); Soybean variety XB58P06
(US2007136867); Soybean Variety XB18M07 (US2006107375); Soybean variety XB36M06
(US2007136866); Soybean Variety XB18K07 (US2006107374); Soybean variety XB22G06
(US2007136865); Soybean Variety XB18J07 (US2006107373); Soybean variety XB36Q06
(US2007136864); Soybean Variety XB17W07 (US2006107372); Soybean variety 91M61
(US2007136863); Soybean Variety XB17U07 (US2006107371); Soybean variety XB32A06
(US2007136862); Soybean Variety XB15807 (US2006107370); Soybean variety XB19V06
(US2007136861); Soybean Variety XB12R07 (US2006107369); Soybean variety XB43C06
(US2007136860); Soybean Variety XB11J07 (US2006107368); Soybean variety XB22N06
(US2007136859); Soybean Variety XB04E07 (US2006107367); Soybean variety XB38E06
(US2007136858); Soybean Variety XB02K07 (US2006107366); Soybean variety XB37U06
(US2007136857); Soybean Variety XB49V07 (US2006107365); Soybean variety XB37Q06
(US2007136856); Soybean Variety XB48X07 (US2006107364); Soybean variety XB00D06
(US2007136855); Soybean Variety 92M75 (US2006107363); Soybean variety XB14N06
(US2007136854); Soybean Variety XB48W07 (US2006107362); Soybean variety XB31H06
(US2007136853); Soybean Variety XB44G07 (US2006107361); Soybean variety XB21Z06
(US2007136852); Soybean Variety XB42K07 (US2006107360); Soybean variety XB005B06
(US2007136851); Soybean Variety XB42H07 (US2006107359); Soybean variety XB15W06
(US2007136850); Soybean Variety X1341.107 (US2006107358); Soybean variety XB33N06
(US2007136849); Soybean Variety XB40Y07 (US2006107357); Soybean variety XB18W06
(US2007136848); Soybean Variety XB40X07 (US2006107356); Soybean variety XB32M06
(US2007136847); Soybean Variety XB39E07 (US2006107355); Soybean variety XB19F06
(US2007136846); Soybean Variety XB38W07 (US2006107354); Soybean variety S03-95021-55-138-AB
(US2007136845); Soybean Variety XB38S07 (U.S. Pat. No. 7,026,531); Soybean variety 94M41 (U.S.
(US2007136844); Soybean Variety XB23V07 Pat. No. 7,002,061); Soybean variety 91M50 (U.S. Pat. No.
(US2007136843); Soybean Variety XB31M07 6,998,518); Soybean variety 92B13 (U.S. Pat. No. 6,989,
(US2007130652); Soybean Variety XB28E07 475); Soybean variety 93B68 (U.S. Pat. No. 6,989,474);
(US2007130651); Soybean Variety XB25S07 Soybean variety 93B09 (U.S. Pat. No. 6,979,759); Soybean
(US2007130650); Soybean Variety XB21N07 variety 92M00 (U.S. Pat. No. 6,972,352); Soybean variety
(US2007130649); Soybean Variety XB03Q07 XB08P05 (US2005120433); Soybean variety XB26V05
(US2007130648); Soybean Variety XB49Q07 (US2005150023); Soybean variety XB21R05
(US2007130647); Soybean Variety XB06M07 (US2005108795); Soybean variety XB28E05
(US2007130646); Soybean variety S04-97130-15-02 (U.S. (US2005114942); Soybean variety XB58K05
Pat. No. 7,196,249); Soybean variety S04-97026-N99- (US2005114941); Soybean variety XB27B05
42648-01 (U.S. Pat. No. 7,189,896); Soybean variety S05- (US2005114940); Soybean variety XB21S05
97016-G99-21212 (U.S. Pat. No. 7,186,894); Soybean variety S05-99048-19 (U.S. Pat. No. 7,164,064); Soybean (US2005150022); Soybean variety XB26U05
(US2005138695); Soybean variety XB35K05
variety 92814 (U.S. Pat. No. 7,161,065); Soybean Variety (US2005150021); Soybean variety XB18S05
98R31 (US2007006350); Soybean variety S05-97177-N00- (US2005120436); Soybean variety XB25C05
22972 (U.S. Pat. No. 7,132,592); Soybean variety XB25G06 (US2005120435); Soybean variety 90M01
(US2006225160); Soybean variety 91M70 (US2005120434); Soybean variety XB22H05
(US2006174381); Soybean variety XB24R06 (US2005150020); Soybean variety XB22K05
(US2006162029); Soybean variety S03-95368-N98-52902 (US2005114939); Soybean variety XB58G05
(U.S. Pat. No. 7,078,594); Soybean variety S05-97130-51 (US2005114938); Soybean variety XB57U05
(U.S. Pat. No. 7,078,599); Soybean variety XB11L06 (US2005120432); Soybean variety XB49M05
(US2006130187); Soybean variety 94B13 (U.S. Pat. No. (US2005120431); Soybean variety XB20D05
7,064,251); Soybean variety 94B74 (U.S. Pat. No. 7,064, (US2005144683); Soybean variety XB41B05
250); Soybean variety XB27J06 (US2006112462); Soybean (US2005150019); Soybean variety XB38T05
variety XB29N06 (US2006112460); Soybean variety (US2005120430); Soybean variety XB13T05
XB28T06 (US2006112459); Soybean variety XB16W06 (US2005120429); Soybean variety XB19Y05
(US2006112458); Soybean variety XB18C06 (US2005120428); Soybean variety XB43D05
(US2006112456); Soybean variety XB 10M06 (US2005120427); Soybean variety XB40E05
(US2006107391); Soybean variety XB06K06 (US2005120426); Soybean variety XB39N05
(US2006107390); Soybean variety XB28V06 (US2005120425); Soybean variety 93M01
(US2006107389); Soybean variety XB004A06 (US2005120424); SOYBEAN VARIETY XB31W05
(US2006107388); Soybean variety XB12L06 (US2005223439); Soybean variety XB32C05
(US2006107387); Soybean variety XB005A06 (US2005114937); Soybean variety XB40D05
(US2006107386); Soybean variety XB25H06 (US2005120423); Soybean variety 92M61
(US2006107385); Soybean variety XB39W06 (US2005120422); Soybean variety 91M91
(US2006107384); Soybean variety XB27K06 (US2005114936); Soybean variety XB33Y05

(US2005120421); Soybean variety XB34A05 (US2005120420); Soybean variety XB13U05 (US2005114935); Soybean variety XB12K05 (US2005114934); Soybean variety XB30P05 (US2005120419); Soybean variety XB57T05 (US2005114933); Soybean variety XB17S05 (US2005114932); Soybean variety XB25Y05 (US2005114930); Soybean variety XB25S05 (US2005150017); Soybean variety XB43W04 (US2004177420); Soybean variety XB44W04 (US2004177419); Soybean variety XB53J04 (US2004199960); Soybean variety XB43V04 (US2004216192); Soybean variety XB49K04 (US2004172668); Soybean variety XB27P04 (US2004205864); Soybean variety XB29L04 (US2004177418); Soybean variety XB29K04 (US2004177417); Soybean variety XB41U04 (US2004231017); Soybean variety XB34D04 (US2004177416); Soybean variety XB09.104 (US2004172711); Soybean variety XB32Y04 (US2004194169); Soybean variety XB44D04 (US2004172710); Soybean variety XB44C04 (US2004172709); Soybean variety XB10L04 (US2004172708); Soybean variety XB19U04 (US2004172707); Soybean variety XB02F04 (US2004172706); Soybean variety XB25X04 (US2004172705); Soybean variety XB26L04 (US2004172704); Soybean variety XB11F04 (US2004172703); Soybean variety XB40Z04 (US2004177415); Soybean variety XB40Y04 (US2004181833); Soybean variety XB007C04 (US2004181832); Soybean variety 96M20 (US2004172702); Soybean variety XB39J04 (US2004172701); Soybean variety XB29A04 (US2004172700); Soybean variety XB35P04 (US2004172699); Soybean variety XB58Z04 (US2004177414); Soybean variety XB43R04 (US2004172698); Soybean variety XB35L04 (US2004172697); Soybean variety XB06H04 (US2004172696); Soybean variety XB59U04 (US2004172695); Soybean variety XB64C04 (US2004172694); Soybean variety 95M80 (US2004172693); Soybean variety XB35Q04 (US2004177413); Soybean variety XB04D04 (US2004177412); Soybean variety XB08L04 (US2004177411); Soybean variety XB18Q04 (US2004177410); Soybean variety XB16Q04 (US2004177409); Soybean variety XB55K04 (US2004172692); Soybean variety XB57M04 (US2004172691); Soybean variety XB25L04 (US2004205863); Soybean variety XB48T04 (US2004194168); Soybean variety XB42X04 (US2004199959); Soybean variety XB31T04 (US2004177408); Soybean variety XB31U04 (US2004194167); Soybean variety XB30E04 (US2004177407); Soybean variety XB31R04 (US2004177406); Soybean variety S03-95341-A98-60618 (U.S. Pat. No. 6,909,033); Soybean variety SN97-6946 (US2004168227); Soybean variety 94M70 (U.S. Pat. No. 6,864,408); Soybean variety 92M70 (U.S. Pat. No. 6,797,866); Soybean variety 92M71 (U.S. Pat. No. 6,858,782); Soybean variety 91M40 (U.S. Pat. No. 6,828,490); Soybean variety 93M80 (U.S. Pat. No. 6,849,789); Soybean variety X839N03 (U.S. Pat. No. 6,864,407); Soybean variety 93M90 (U.S. Pat. No. 6,846,975); Soybean variety 90M90 (U.S. Pat. No. 6,852,913); Soybean variety 92M72 (U.S. Pat. No. 6,960,708); Soybean variety 91M90 (U.S. Pat. No. 6,849,788); Soybean variety 92M50 (U.S. Pat. No. 6,855,876); Soybean variety 92M30 (U.S. Pat. No. 6,951,974); Soybean variety 93M60 (U.S. Pat. No. 6,797,865); Soybean variety 93M40 (U.S. Pat. No. 6,791,016); Soybean variety 93M41 (U.S. Pat. No. 6,835,875); Soybean variety XB15P03 (U.S. Pat. No. 6,797,864); Soybean variety XB24H03 (U.S. Pat. No. 6,936,752); Soybean variety XB05A03 (U.S. Pat. No. 6,815,585); Soybean variety 92M80 (U.S. Pat. No. 6,849,787); Soybean variety XB33S03 (U.S. Pat. No. 6,855,875); Soybean variety XB48P03 (U.S. Pat. No. 6,797,863); Soybean variety XB29X03 (U.S. Pat. No. 6,806,406); Soybean variety XB02C03 (U.S. Pat. No. 6,800,795); Soybean variety XB29W03 (U.S. Pat. No. 6,858,781); Soybean variety 91M10 (U.S. Pat. No. 6,958,437); Soybean variety 92M10 (U.S. Pat. No. 6,916,975); Soybean variety XB10G03 (U.S. Pat. No. 6,806,405); Soybean variety 92M31 (U.S. Pat. No. 6,846,974); Soybean variety XB38D03 (U.S. Pat. No. 6,806,404); Soybean variety XB34N03 (U.S. Pat. No. 6,803,508); Soybean variety XB30W03 (U.S. Pat. No. 6,809,236); Soybean variety XB37J03 (U.S. Pat. No. 6,844,488); Soybean variety SE72581 (US2004148665); Soybean variety SE90076 (US2004148664); Soybean variety SD82997 (US2004148663); Soybean variety 0037393 (US2004148662); Soybean variety 0088414 (US2004148661); Soybean variety 0149926 (US2004148660); Soybean variety 0037209 (US2004148659); Soybean variety 93B36 (U.S. Pat. No. 6,833,498); Soybean variety 90B74 (U.S. Pat. No. 6,812,384); Soybean variety 90851 (U.S. Pat. No. 6,818,809); Soybean variety 91B03 (U.S. Pat. No. 6,815,584); Soybean variety 95B43 (U.S. Pat. No. 6,818,808); Soybean variety 95B42 (U.S. Pat. No. 6,815,583); Soybean variety 92B47 (U.S. Pat. No. 6,812,383); Soybean variety SE90346 (US2004055055); Soybean variety 0007583 (US2004010824); Soybean variety 0008079 (US2004010823); Soybean variety S02-AP98041-2-333-01 (US2003121076); Soybean variety S02-98041-2-251-01 (US2003182694); Soybean variety S02-AP98041-2-262-02 (US2003196220); Soybean variety S02-95021-55-240-BA (US2003188348); Soybean variety APA94-31572 (US2003061641); Soybean variety AP98041-1-203 (US2003056251); Soybean variety APA95-15294 (US2003061640); Soybean variety AP98041-4-117 (US2003056250); Soybean variety 91B33 (U.S. Pat. No. 6,580,018); Soybean variety 93B85 (U.S. Pat. No. 6,605,762); Soybean variety 92B76 (U.S. Pat. No. 6,610,911); Soybean variety 92B38 (U.S. Pat. No. 6,605,761); Soybean variety 94B24 (U.S. Pat. No. 6,613,967); Soybean variety 94B73 (U.S. Pat. No. 6,605,760); Soybean variety 93B86 (U.S. Pat. No. 6,610,910); Soybean variety 91B12 (U.S. Pat. No. 6,583,343); Soybean variety 95B34 (U.S. Pat. No. 6,605,759); Soybean variety 94B23 (U.S. Pat. No. 6,605,758); Soybean variety 90B11 (U.S. Pat. No. 6,583,342); Soybean variety 91B92 (U.S. Pat. No. 6,586,659); Soybean variety 95B96 (U.S. Pat. No. 6,605,757); Soybean variety 93B72 (U.S. Pat. No. 6,566,589); Soybean variety 95B97 (U.S. Pat. No. 6,613,966); Soybean variety 92B95 (U.S. Pat. No. 6,608,243); Soybean variety 93847 (U.S. Pat. No. 6,583,341); Soybean variety 97B52 (U.S. Pat. No. 6,605,756); Soybean variety 93B15 (U.S. Pat. No. 6,617,499); Soybean variety 94854 (U.S. Pat. No. 6,613,965); Soybean variety 93B67 (U.S. Pat. No. 6,573,433); Soybean variety 93B87 (U.S. Pat. No. 6,727,410); Soybean variety 96B51 (U.S. Pat. No. 6,613,964); Soybean variety 92884 (U.S. Pat. No. 6,730,829); Soybean variety 92B12 (U.S. Pat. No. 6,605,755); Soybean variety 90A07 (U.S. Pat. No. 6,320, 105); Soybean variety 93B26 (U.S. Pat. No. 6,342,659); Soybean variety 96821 (U.S. Pat. No. 6,369,301); Soybean variety 92B63 (U.S. Pat. No. 6,326,529); Soybean variety 93B46 (U.S. Pat. No. 6,323,402); Soybean variety 92B75 (U.S. Pat. No. 6,362,400); Soybean variety 93808 (U.S. Pat. No. 6,323,401); Soybean variety 97B62 (U.S. Pat. No. 6,323,400); Soybean variety 92837 (U.S. Pat. No. 6,323,399); Soybean variety 92B56 (U.S. Pat. No. 6,339,186); Soybean variety 93B66 (U.S. Pat. No. 6,307,131); Soybean variety 92B62 (U.S. Pat. No. 6,346,657); Soybean variety 92B36 (U.S. Pat. No. 6,369,300); Soybean variety 90B73 (U.S. Pat. No. 6,316,700); Soybean variety 95B95 (U.S. Pat. No. 6,323,398); Soybean variety 931365 (U.S. Pat. No. 6,229,074); Soybean variety 92B24 (U.S. Pat. No. 6,284,950); Soybean variety 94B53 (U.S. Pat. No. 6,235,976); Soybean variety 94822 (U.S. Pat. No. 6,140,557); Soybean variety 93B84 (U.S. Pat. No. 6,143,956); Soybean variety 951332 (U.S. Pat. No. 6,229,073); Soybean variety 95B53 (U.S. Pat. No. 6,147,283); Soybean variety 93B35 (U.S. Pat. No. 6,153,816); Soybean variety 93B07 (U.S. Pat. No. 6,143,955); Soybean variety 921374 (U.S. Pat. No. 6,124,526); Soybean variety 92B35 (U.S. Pat. No. 6,166,296); Soybean variety 94B45 (U.S. Pat. No. 6,162,968); Soybean variety 96B01 (US6143954); Soybean variety 93B53 (U.S. Pat. No. 6,335,197).

It is observed that the introgression of the elite event into these cultivars does not significantly influence any of the desirable phenotypic or agronomic characteristics of these cultivars (no yield drag) while expression of the transgene, as determined by glyphosate and/or isoxaflutole tolerance, meets commercially acceptable levels. This confirms the status of event EE-GM3 as an elite event.

Elite event EE-GM3 may be advantageously combined with one or more of other soybean events available in the market, including but not limited to other herbicide tolerance events, such as events described in USDA-APHIS petitions: 09-349-01p, 09-201-01p, 09-183-01p, 09-082-01p, 09-015-01p, 06-354-01p, 06-271-01p, 06-178-01p, 98-238-01p, 98-014-01p, 97-008-01p, 96-068-01p, 95-335-01p, 93-258-01p (see, e.g., www.aphis.usda.gov/brs/not_reg.html), or event MON89788 (Glyphosate tolerance) described in US2006-282915, event DP-305423-1 (High oleic acid ALS inhibitor tolerance) described in WO 2008/054747, events A2704-12 and A5547-127 (Glufosinate tolerance) described respectively in WO 2006/108674 or WO 2006/108675, MON87701 described in US2009130071, event 3560.4.3.5 described in US2009036308, event DP-305423-1 described in US2008312082, or event BPS-CV127-9 (Event 127) of WO 2010/080829.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GM3 was deposited as 32-RRMM-0531 at the NCIMB (Ferguson Building, Craibstone Estate, Bucksbum, Aberdeen AB9YA, Scotland) on Oct. 12, 2009, under NCIMB accession number NCIMB 41659, and the viability thereof was confirmed. Alternative names for EE-GM3 are event FG-072, or event MST-FG72-3.

The above description of the invention is intended to be illustrative and not limiting.

Various changes or modifications in the embodiments described may occur to those skilled in the art. These can be made without departing from the spirit or scope of the invention.

SEQUENCE LISTING

```
<160> NUMBER OF SEQ ID NOS: 13

<210> SEQ ID NO 1
<211> LENGTH: 7296
<212> TYPE: DNA
<213> ORGANISM: Artificial Sequence
<220> FEATURE:
<223> OTHER INFORMATION: SalI fragment of vector pSF10
<220> FEATURE:
<221> NAME/KEY: terminator
<222> LOCATION: (188)..(479)
<223> OTHER INFORMATION: 3 nos- sequence including the 3 untranslated
      region of the nopaline synthase gene from the T-DNA of pTiT37 of
      Agrobacterium tumefaciens -complement
<220> FEATURE:
<221> NAME/KEY: misc_feature
<222> LOCATION: (480)..(1556)
<223> OTHER INFORMATION: hppdPf W336- the coding sequence of the
      4-hydroxyphenylpyruvate dioxygenase of Pseudomonas fluorescens
      strain A32 modified by the replacement of the amino acid Glycine
      336 with a Tryptophane - complement
<220> FEATURE:
<221> NAME/KEY: transit_peptide
<222> LOCATION: (1557)..(1928)
<223> OTHER INFORMATION: TPotp Y- coding sequence of an optimized
      transit peptide derivative (position 55 changed into Tyrosine),
      containing sequence of the RuBisCO small subunit genes of Zea mays
      (corn) and Helianthus annuus (sunflower)-complement
<220> FEATURE:
<221> NAME/KEY: 5 UTR
<222> LOCATION: (1929)..(2069)
<223> OTHER INFORMATION: 5'tev- sequence including the leader sequence
      of the tobacco etch virus-complement
<220> FEATURE:
```

```
<221> NAME/KEY: promoter
<222> LOCATION: (2070)..(3359)
<223> OTHER INFORMATION: Ph4a748 ABBC- sequence including the promoter
      region of the histone H4 gene of Arabidopsis thaliana, containing
      an internal duplication - complement
<220> FEATURE:
<221> NAME/KEY: promoter
<222> LOCATION: (3360)..(4374)
<223> OTHER INFORMATION: Ph4a748- sequence including the promoter region
      of the histone H4 gene of Arabidopsis thaliana
<220> FEATURE:
<221> NAME/KEY: Intron
<222> LOCATION: (4375)..(4855)
<223> OTHER INFORMATION: intron1 h3At- first intron of gene II of the
      histone H3.III variant of Arabidopsis thaliana
<220> FEATURE:
<221> NAME/KEY: transit_peptide
<222> LOCATION: (4856)..(5227)
<223> OTHER INFORMATION: TPotp C- coding sequence of the optimized
      transit peptide, containing sequence of the RuBisCO small subunit
      genes of Zea mays (corn) and Helianthus annuus (sunflower)
<220> FEATURE:
<221> NAME/KEY: misc_feature
<222> LOCATION: (5228)..(6565)
<223> OTHER INFORMATION: 2mepsps- the coding sequence of the
      double-mutant 5-enol-pyruvylshikimate-3-phosphate synthase gene of
      Zea mays (corn) (Lebrun et al., 1997)
<220> FEATURE:
<221> NAME/KEY: terminator
<222> LOCATION: (6566)..(7252)
<223> OTHER INFORMATION: 3 histonAt- sequence including the 3
      untranslated region of the histone H4 gene of Arabidopsis thaliana
      (Chaboute et al., 1987)

<400> SEQUENCE: 1
gtcgactcta gcagatctgg ccggcccacc ggtgggccat atgggcccgc ggccgcgaat      60
tcgagctcgg tacctacctg gcgaaagggg gatgtgctgc aaggcgatta agttgggtaa    120
cgccagggtt ttcccagtca cgacgttgta aaacgacggc cagtgaattg cggccgcaat    180
tcccgatcta gtaacataga tgacaccgcg cgcgataatt tatcctagtt tgcgcgctat    240
attttgtttt ctatcgcgta ttaaatgtat aattgcggga ctctaatcat aaaaacccat    300
ctcataaata acgtcatgca ttacatgtta attattacat gcttaacgta attcaacaga    360
aattatatga taatcatcgc aagaccggca acaggattca atcttaagaa actttattgc    420
caaatgtttg aacgatcggg gaaattcgtc gagtcaccct cggccgggct ttttgacgct    480
taatcggcgg tcaatacacc acgacgcacc tggtcacgtt cgatggactc gaacagcgcc    540
ttgaagttcc actcgccaaa cccatcgtcg cccttgcgct ggatgaattc gaagaacacc    600
gggcccatca gggtttccga gaagatctgc agcagcaggc gtttgtcgcc ttccacggaa    660
gatccgtcca gcaggatacc gcgtgcctgc agttgatcca ccggctcgcc gtggtcaggc    720
aggcggcctt cgagcatttc gtaataagtg tctggcggcg cggtcatgaa gcgcatgccg    780
attttcttca acgcgtccca ggtcttgacc aggtcgtcgg tgaggaacgc cacgtgctgg    840
atgccttcgc cgttgaactg catcaggaac tcttcgatct gccccgcgcc cttgacgac     900 tcttcgttca gcgggatgcg gatcatgccg tccggcgcac tcatggcctt ggaagtcagg    960
ccggtgtact cgcccttgat atcgaagtaa cgcgcttcac ggaagttgaa caatttctcg   1020
tagaagttgg cccagtagac catgcggccg cgatagacgt tgtgggtcag gtggtcgatg   1080
actttgagac ctgcaccgac cggattgcgc tccacacctt cgaggtacac gaagtcgatg   1140
tcgtagatcg agctgccttc gccgaaacgt cgatcaggt acaacggcgc gccgccgatg    1200
cccttgatcg ccggcaggtt caattccatc ggccggtgt caatatggat cggctgggcg    1260
ccgagttcca gggcgcggtt gtaggccttt tgcgagtcct tcacgcggaa cgccatgccg   1320
```

-continued

```
cacaccgacg ggccgtgttc ggccgcaaag taggaggcga tgctgttggg ctcgttgttg    1380
aggatcaggt tgatctcgcc ctggcggtac aggtgcacgt tcttggaacg gtgggtcgcg    1440
actttggtga agcccatgat ctcgaagatc ggctccaggg tacccggcgt cggcgacgcg    1500
aattcgatga attcaaagcc catcaggccc attgggtttt cgtatagatc tgccatgcac    1560
cggatccttc cgccgttgct gacgttgccg aggcttctgg aggagcggcg ggcgacgggg    1620
aggctggcgt tggacttgag cccctggaac ggagcgacgg cggtggccga cgaggccatc    1680
atcacggtgg gcgccataga cagcggcggc aggtacgaca gcgtctcgaa cttcttgttg    1740
ccgtaggccg gccacacctg catatattga actcttccac cgttgctggg aagggtggag    1800
aagtcgttag ccttcttggt ggtggggaag gcggcgttgg acttaaggcc ggtgaacgga    1860
gccaccatgt tggcctgagc aggggcggtc cggctaacgg tcgcgactga ggaggagatc    1920
gaagccatgg ctatcgttcg taaatggtga aaattttcag aaaattgctt ttgctttaaa    1980
agaaatgatt taaattgctg caatagaagt agaatgcttg attgcttgag attcgtttgt    2040
tttgtatatg ttgtgtttcg aattctagag tcgagagaaa ttgatgtctg tagaagaaga    2100
agaacggtta agagtagatt tgggtgagaa agatgtgaaa ttgttttttat aggcaaagac    2160
ggagagtcta ttttttgagc aatcagatcg catattaaat ctaacggctg agatatcgat    2220
ccgtgtgtac aataaaatga tgtataaacc gtcgatctgt tttaatcgac ggttcatatt    2280
agtgatccgc gtgatggcag tgatagccac taagaatcgt cttttgtttt acatgtggcg    2340
ccacaaatta gggtaatgaa gcggcaatat tttggaactc ggaaaataaa attgcgccat    2400
cacattattt gaaaattttc acatgctttt attttaaaaa cccacgaatt acaagttaca    2460
accgaaaaag atttataata tagtgattta tactaatttt gtagtagctt aatgtatatt    2520
gatactggaa aaacaatgac aatcatacga tccgtgtgta caataaaatg atgtataaac    2580
cgtcgatctg ttttaatcga cggttcatat tagtgatccg cgtgatggca gtgatagcca    2640
ctaagaatcg tcttttgttt tacatgtggc gccacaaatt agggtaatga agcggcaata    2700
ttttggaact cggaaaataa aattgcgcca tcacattatt tgaaaatttt cacatgcttt    2760
tattttaaaa acccacgaat tacaagttac aaccgaaaaa gatttataat atagtgattt    2820
atactaattt tgtagtagct taatgtatat tgatactgga aaaacaatga caatcatatg    2880
ttagtattat caagttatcg tattgatatt gatattggaa catacaatgg gtattgcctt    2940
ctttcgacca taaatatcac caaatttaca aagtttgtgt ataccaagtt atcaattgta    3000
aatgggatgt caacattta atttccctt gagaaactat agaccacaag aacacacttc    3060
aatagataaa gtaactattt acataagagg ttttaaaatc acattaacaa aaataattac    3120
caaccggcac tcacaaatac aaacagagca cacgacatgt caaagccaca agtaaattcg    3180
ttgagtggtg gtttcattac aattgtgtca cttgcagcac aaactatctt gctctgggaa    3240
tcatctcagc atcaaagatc atgctcactt caggggaact tagtgtatcc atgcctcgac    3300
tcatatttct cctcgacctg caggcatgca agctctagag cggccgccac cgcggtggag    3360
gtactcgagt cgcgacgtac gttcgaacaa ttggttttaa aagcttgcat gcctgcaggt    3420
cgaggagaaa tatgagtcga ggcatggata cactaagttc ccctgaagtg agcatgatct    3480
ttgatgctga gatgattccc agagcaagat agtttgtgct gcaagtgaca caattgtaat    3540
gaaaccacca ctcaacgaat ttacttgtgg ctttgacatg tcgtgtgctc tgtttgtatt    3600
tgtgagtgcc ggttggtaat tatttttgtt aatgtgattt taaaacctct tatgtaaata    3660
```

```
gttactttat ctattgaagt gtgttcttgt ggtctatagt ttctcaaagg gaaattaaaa    3720
tgttgacatc ccatttacaa ttgataactt ggtatacaca aactttgtaa atttggtgat    3780
atttatggtc gaaagaaggc aatacccatt gtatgttcca atatcaatat caatacgata    3840
acttgataat actaacatat gattgtcatt gttttttccag tatcaatata cattaagcta    3900
ctacaaaatt agtataaatc actatattat aaatcttttt cggttgtaac ttgtaattcg    3960
tgggttttta aaataaaagc atgtgaaaat tttcaaataa tgtgatggcg caattttatt    4020
ttccgagttc caaaatattg ccgcttcatt accctaattt gtggcgccac atgtaaaaca    4080
aaagacgatt cttagtggct atcactgcca tcacgcggat cactaaatatg aaccgtcgat    4140 taaaacagat cgacggttta tacatcattt tattgtacac acggatcgat atctcagccg    4200
ttagatttaa tatgcgatct gattgctcaa aaaatagact ctccgtcttt gcctataaaa    4260
acaatttcac atctttctca cccaaatcta ctcttaaccg ttcttcttct tctacagaca    4320
tcaatttctc tcgactctag aggatccaag cttatcgatt tcgaacccct caggcgaaga    4380
acaggtatga tttgtttgta attagatcag gggtttaggt cttccatta cttttttaatg    4440 tttttctgt tactgtctcc gcgatctgat tttacgacaa tagagtttcg ggttttgtcc    4500
cattccagtt tgaaaataaa ggtccgtctt ttaagtttgc tggatcgata aacctgtgaa    4560
gattgagtct agtcgattta ttggatgatc cattcttcat cgttttttttc ttgcttcgaa    4620 gttctgtata accagatttg tctgtgtgcg attgtcatta cctagccgtg tatcgagaac    4680
tagggttttc gagtcaattt tgcccctttt ggttatatct ggttcgataa cgattcatct    4740
ggattagggt tttaagtggt gacgtttagt attccaattg cttcaaaatt tagttatgga    4800
taatgaaaat ccccaattga ctgttcaatt tcttgttaaa tgcgcagatc cccatggctt    4860
cgatctcctc ctcagtcgcg accgttagcc ggaccgcccc tgctcaggcc aacatggtgg    4920
ctccgttcac cggccttaag tccaacgccg ccttccccac caccaagaag gctaacgact    4980
tctccaccct tcccagcaac ggtggaagag ttcaatgtat gcaggtgtgg ccggcctacg    5040
gcaacaagaa gttcgagacg ctgtcgtacc tgccgccgct gtctatggcg cccaccgtga    5100
tgatggcctc gtcggccacc gccgtcgctc cgttccaggg gctcaagtcc accgccagcc    5160
tccccgtcgc ccgccgctcc tccagaagcc tcggcaacgt cagcaacggc ggaaggatcc    5220
ggtgcatggc cggcgccgag gagatcgtgc tgcagcccat caaggagatc tccggcaccg    5280
tcaagctgcc ggggtccaag tcgctttcca accggatcct cctactcgcc gccctgtccg    5340
aggggacaac agtggttgat aacctgctga acagtgagga tgtccactac atgctcgggg    5400
ccttgaggac tcttggtctc tctgtcgaag cggacaaagc tgccaaaaga gctgtagttg    5460
ttggctgtgg tggaaagttc ccagttgagg atgctaaaga ggaagtgcag ctcttcttgg    5520
ggaatgctgg aatcgcaatg cggtccttga cagcagctgt tactgctgct ggtggaaatg    5580
caacttacgt gcttgatgga gtaccaagaa tgagggagag acccattggc gacttggttg    5640
tcggattgaa gcagcttggt gcagatgttg attgtttcct tggcactgac tgcccacctg    5700
ttcgtgtcaa tggaatcgga gggctacctg gtggcaaggt caagctgtct ggctccatca    5760
gcagtcagta cttgagtgcc ttgctgatgg ctgctcctt ggctcttggg gatgtggaga    5820
ttgaaatcat tgataaatta atctccattc cgtacgtcga aatgacattg agattgatgg    5880
agcgttttgg tgtgaaagca gagcattctg atagctggga cagattctac attaagggag    5940
gtcaaaaata caagtcccct aaaaatgcct atgttgaagg tgatgcctca agcgcaagct    6000
atttcttggc tggtgctgca attactggag ggactgtgac tgtggaaggt tgtggcacca    6060
```

```
ccagtttgca gggtgatgtg aagtttgctg aggtactgga gatgatggga gcgaaggtta    6120
catggaccga gactagcgta actgttactg gcccaccgcg ggagccattt gggaggaaac    6180
acctcaaggc gattgatgtc aacatgaaca agatgcctga tgtcgccatg actcttgctg    6240
tggttgccct ctttgccgat ggcccgacag ccatcagaga cgtggcttcc tggagagtaa    6300
aggagaccga gaggatggtt gcgatccgga cggagctaac caagctggga gcatctgttg    6360
aggaagggcc ggactactgc atcatcacgc cgccggagaa gctgaacgtg acggcgatcg    6420
acacgtacga cgaccacagg atggcgatgg ctttctccct tgccgcctgt gccgaggtcc    6480
ccgtcaccat ccgggaccct gggtgcaccc ggaagacctt ccccgactac ttcgatgtgc    6540
tgagcacttt cgtcaagaat taagctctag aactagtgga tcccccgatc cgcgtttgtg    6600
ttttctgggt ttctcactta agcgtctgcg ttttacttt gtattgggtt tggcgtttag      6660
tagtttgcgg tagcgttctt gttatgtgta attacgcttt ttcttcttgc ttcagcagtt    6720
tcggttgaaa tataaatcga atcaagtttc actttatcag cgttgtttta aattttggca    6780
ttaaattggt gaaaattgct tcaattttgt atctaaatag aagagacaac atgaaattcg    6840
acttttgacc tcaaatcttc gaacatttat ttcctgattt cacgatggat gaggataacg    6900
aaagggcggt tcctatgtcc gggaaagttc ccgtagaaga caatgagcaa agctactgaa    6960
acgcggacac gacgtcgcat tggtacggat atgagttaaa ccgactcaat tcctttatta    7020
agacataaac cgattttggt taaagtgtaa cagtgagctg atataaaacc gaaacaaacc    7080
ggtacaagtt tgattgagca acttgatgac aaacttcaga attttggtta ttgaatgaaa    7140
atcatagtct aatcgtaaaa aatgtacaga agaaaagcta gagcagaaca aagattctat    7200
attctggttc caatttatca tcgctttaac gtccctcaga tttgatcggg ctgcaggaat    7260
taaacgcccg ggcacgtggg atcctctaga gtcgac                              7296
```

<210> SEQ ID NO 2
<211> LENGTH: 1843
<212> TYPE: DNA
<213> ORGANISM: Artificial Sequence
<220> FEATURE:
<223> OTHER INFORMATION: 5 flanking region of the foreign DNA comprising herbicide tolerance genes in EE-GM3
<220> FEATURE:
<221> NAME/KEY: misc_feature
<222> LOCATION: (1)..(1451)
<223> OTHER INFORMATION: plant DNA
<220> FEATURE:
<221> NAME/KEY: misc_feature
<222> LOCATION: (1452)..(1843)
<223> OTHER INFORMATION: insert or foreign DNA

<400> SEQUENCE: 2

```
gacttccatg tctagattca ttgtactaag atttcaaacg atatatatat atatatatat      60
atatatattc aattacatct ttttcaaaaa acatatatgc atcgtatttt ctaatacatt     120
tttttatata tgttattagt taaaatttat taaaaatcat aaaattaagt aagtttcaca     180
taacatccaa tgatttttctc gtaatttttaa gactggacta agaatatag tagtaacact    240 tctcttcaaa taatatactt tatttgcccg aggaatagca ttgccatatt gaactattag     300
gaaagctgaa catcaattgg tacacttgga tggttcccac ggtttattat tgtctacatc     360
tggtcatcca agcagaggtt atatcttcta taactcgaca atcttcgtt gtgcctatat      420 agagttgctt gtacgactaa aacgcttata ataatcgtta tacaatctat gattcacagt    480
tatgatacgt gtatgcaata aatgaataga tagataaata tgatacaatt atacaattat    540
```

| tctaaaatat atagaataca atatatgtat gtataaaaaa ttcataaaac accaataagc | 600 |
| ataταattgc aattttgcaa accaaatta agaatataac tcaaatatta ctagaaacaa | 660 |
| aaaaaattat aaatcattgt cttcataaat taattctaag tatctacaaa tagaaataat | 720 |
| atgaattta tataaaaaag taatataaat tttattcctt tcttaaattt atgaaaaata | 780 |
| atacttctat atttctatac atgtttctat acatgcgttt caatgtctga tagtgatagg | 840 |
| aaactctact gtattttcaa aagtttttt ttgttaaat atatttttg tcatgtaatt | 900 |
| gtgtgtgttt tcatttacgt ccatgtaaaa agaaaatatt ttagttctat taaaatattt | 960 |
| tttttattt ttatccttaa aatactttaa ataaatttt ttcctatta aagcatttt | 1020 |
| tataattaa agcgctattt aaaacgttt tagaataaaa acataaaca aacacatttt | 1080 |
| aaaatgattg aaatgaaaaa taaaactaat gaaaacgaaa acaatactaa attacaggaa | 1140 |
| agaaaatat attcaaactt ttatgtttaa aggtttttga atatttctct gattcgtttg | 1200 |
| aaatatgtga agaaaattaa aatatcaagt agtaggttac aacagttcgg gtgcaacagt | 1260 |
| gactatgaca gcaagataat agggccaata tatttggata cctctcttaa gacgtaaaca | 1320 |
| ttttgagcga gaaaataatg gaaaaaaaat aagtcattca aatgataata gatatataaa | 1380 |
| ttatttttta ttttaaatat cttattaata tttttattt tttatcatat tataaattat | 1440 |
| attatattta tgtagctttg ctcattgtct tctacgggaa cttcccgga cataggaacc | 1500 |
| gcccttcgt tatcctcatc catcgtgaaa tcaggaaata aatgttcgaa gatttgaggt | 1560 |
| caaaagtcga atttcatgtt gtctcttcta tttagataca aaattgaagc aatttcacc | 1620 |
| aattaatgc caaatttaa aacaacgctg tcctgatttc acgatggatg aggataacga | 1680 |
| aagggcggtt cctatgtccg ggaaagttcc cgtagaagac aatgagcaaa gctactgaaa | 1740 |
| cgcggacacg acgtcgcatt ggtacggata tgagttaaac cgactcaatt cctttattaa | 1800 |
| gacataaacc gatttggtt aaagtgtaac agtgagctga tat | 1843 |

<210> SEQ ID NO 3
<211> LENGTH: 1408
<212> TYPE: DNA
<213> ORGANISM: Artificial Sequence
<220> FEATURE:
<223> OTHER INFORMATION: 3 flanking sequence of foreign DNA comprising
      herbicide tolerance genes in EE-GM3
<220> FEATURE:
<221> NAME/KEY: misc_feature
<222> LOCATION: (1)..(240)
<223> OTHER INFORMATION: insert or foreign DNA
<220> FEATURE:
<221> NAME/KEY: misc_feature
<222> LOCATION: (241)..(1408)
<223> OTHER INFORMATION: plant DNA

<400> SEQUENCE: 3

| taacagtgag ctgatataaa accgaaacaa accggtacaa gtttgattga gcaacttgat | 60 |
| gacaaacttc agaattttgg ttattgaatg aaaatcatag tctaatcgta aaaaatgtac | 120 |
| agaagaaaag ctagagcaga acaaagattc tatattctgg ttccaattta tcatcgcttt | 180 |
| aacgtccctc agatttgatc gggctgcagg aattaatgtg gttcatccgt ctttttgtta | 240 |
| atgcggtcat caatacgtgc ctcaaagatt gccaaataga ttaatgtggt tcatctccct | 300 |
| atatgttttg cttgttggat tttgctatca catgtttatt gctccaaact aattataata | 360 |
| aaatgacttt caaatgattg gtgttgacat tcttttcaaa ttgttcgctg aagaaaagat | 420 |
| aatctcgagg ccttgattg ttaatgcttt cattaataaa taaataaat aactctttcc | 480 |

```
aaatttcaat tcatgctttt atattgtgtg gttcatcctc atcttatgtc actattatca    540
tttcatgttt gagactttac ttggccatat ttgagaagac cttcttcatt ataggcaatt    600
ttatctccac aataatataa gagaatatct tgaattaata attattgagg atatattata    660
gggttctatg tggaactaaa gacatggtta ccccattaag agagagtata gaggaattac    720
ttttatttgc cacgaggcga cgcgacttgt atttattttg gaattgtact tttgcgtgag    780
cagtgtggct ctatgttggg gcctccactt gttggtgttt tatatatgtg aaaggaggat    840
gagggtgatg gttcatttct ttgcattatt tttgttattc gcgcgaatga tatatgccct    900 gttttttgaag attgataggg aagtccatat ataggaattg aagtgtcaaa agggtgtgag    960
tatgtgctat gataatcacc caattaatgt acatctggtg tggtgtttga atttgtaggt   1020
cattaattaa tattcctctt ggtgaagttt ggagttcttt tgcaattaca attctgttt    1080 gtaagtgatt atgatggact tttagatgtt tctcaaacag taggtgtaaa gaaaaatggg   1140
ccctggtatg aaaatttgtt ttcactcttt ctcattcata tctttaaaaa aagaatgata   1200
attttgtaat aaaaataaaa aaatattaaa tattttctca aatcaaacaa ccttatttt    1260 ttatgccaac aataattttg ttaaagatgg agatttcaat tattatataa gagttcatta   1320
tagttgaaaa ttgaatgaat gtatatgttt acgttttttg tctcaagtga aactaagatc   1380
aaatattcat atctattgag ctggtctt                                     1408
```

```
<210> SEQ ID NO 4
<211> LENGTH: 20
<212> TYPE: DNA
<213> ORGANISM: Artificial Sequence
<220> FEATURE:
<223> OTHER INFORMATION: primer SOY028

<400> SEQUENCE: 4
atcgctttaa cgtccctcag                                                20

<210> SEQ ID NO 5
<211> LENGTH: 18
<212> TYPE: DNA
<213> ORGANISM: Artificial Sequence
<220> FEATURE:
<223> OTHER INFORMATION: primer SOY029

<400> SEQUENCE: 5
caaggcctcg agattatc                                                  18

<210> SEQ ID NO 6
<211> LENGTH: 20
<212> TYPE: DNA
<213> ORGANISM: Artificial Sequence
<220> FEATURE:
<223> OTHER INFORMATION: primer SMP187

<400> SEQUENCE: 6
atatcaaccc gtagctcgac                                                20

<210> SEQ ID NO 7
<211> LENGTH: 23
<212> TYPE: DNA
<213> ORGANISM: Artificial Sequence
<220> FEATURE:
<223> OTHER INFORMATION: primer STV019

<400> SEQUENCE: 7
```

```
<210> SEQ ID NO 8
<211> LENGTH: 263
<212> TYPE: DNA
<213> ORGANISM: Artificial Sequence
<220> FEATURE:
<223> OTHER INFORMATION: nucleotide sequence of PCR amplicon using
      primers SOY028 - SOY029

<400> SEQUENCE: 8
atcgctttaa cgtccctcag atttgatcgg gctgcaggaa ttaatgtggt tcatccgtct      60
ttttgttaat gcggtcatca atacgtgcct caaagattgc caaatagatt aatgtggttc    120
atctccctat atgttttgct tgttggattt tgctatcaca tgtttattgc tccaaactaa    180
ttataataaa atgactttca aatgattggt gttgacattc ttttcaaatt gttcgctgaa    240
gaaaagataa tctcgaggcc ttg                                            263

<210> SEQ ID NO 9
<211> LENGTH: 20
<212> TYPE: DNA
<213> ORGANISM: Artificial Sequence
<220> FEATURE:
<223> OTHER INFORMATION: primer 1 for amplication of control fragment
      (SOY01)

<400> SEQUENCE: 9
gtcagccaca cagtgcctat                                                 20

<210> SEQ ID NO 10
<211> LENGTH: 20
<212> TYPE: DNA
<213> ORGANISM: Artificial Sequence
<220> FEATURE:
<223> OTHER INFORMATION: primer 2 for amplication of control fragment
      (SOY02)

<400> SEQUENCE: 10
gttaccgtac aggtctttcc                                                 20

<210> SEQ ID NO 11
<211> LENGTH: 17806
<212> TYPE: DNA
<213> ORGANISM: Artificial Sequence
<220> FEATURE:
<223> OTHER INFORMATION: nucleotide sequence of a foreign DNA and plant
      flanking sequences in event EE-GM3

<400> SEQUENCE: 11
gacttccatg tctagattca ttgtactaag atttcaaacg atatatatat atatatatat     60
atatatattc aattacatct ttttcaaaaa acatatatgc atcgtatttt ctaatacatt    120
tttttatata tgttattagt taaaatttat taaaaatcat aaaattaagt aagtttcaca    180
taacatccaa tgattttctc gtaattttaa gactggacta agaatatag tagtaacact     240 tctcttcaaa taatatactt tatttgcccg aggaatagca ttgccatatt gaactattag    300
gaaagctgaa catcaattgg tacacttgga tggttcccac ggtttattat tgtctacatc    360
tggtcatcca agcagaggtt atatcttcta aactcgaca aatcttcgtt gtgcctatat     420
agagttgctt gtacgactaa aacgcttata ataatcgtta tacaatctat gattcacagt    480
tatgatacgt gtatgcaata aatgaataga tagataaata tgatacaatt atacaattat    540
tctaaaatat atagaataca atatatgtat gtataaaaaa ttcataaaac accaataagc    600
```

```
atataattgc aattttgcaa aaccaaatta agaatataac tcaaatatta ctagaaacaa      660
aaaaaattat aaatcattgt cttcataaat taattctaag tatctacaaa tagaaataat      720 atgaattta tataaaaaag taatataaat tttattcctt tcttaaattt atgaaaaata       780
atacttctat atttctatac atgtttctat acatgcgttt caatgtctga tagtgatagg      840
aaactctact gtattttcaa aagtttttt ttgtttaaat atattttttg tcatgtaatt       900
gtgtgtgttt tcatttacgt ccatgtaaaa agaaaatatt ttagttctat taaaatattt      960
tttttatttt ttatccttaa aatactttaa ataatatttt ttcctattta aagcattttt     1020
tataatttaa agcgctattt aaaacgtttt tagaataaaa acataaaaca aacacatttt     1080
aaaatgattg aaatgaaaaa taaaactaat gaaaacgaaa acaatactaa attacaggaa     1140
agaaaaatat attcaaactt ttatgtttaa aggttttga atatttctct gattcgtttg      1200
aaatatgtga agaaaattaa aatatcaagt agtaggttac aacagttcgg gtgcaacagt     1260
gactatgaca gcaagataat agggccaata tatttggata cctctcttaa gacgtaaaca     1320
ttttgagcga gaaaataatg gaaaaaaaat aagtcattca aatgataata gatatataaa     1380 ttattttta ttttaaatat cttattaata ttttttatttt tttatcatat tataaaattat     1440 attatattta tgtagctttg ctcattgtct tctacgggaa ctttcccgga cataggaacc     1500
gccctttcgt tatcctcatc catcgtgaaa tcaggaaata aatgttcgaa gatttgaggt     1560
caaaagtcga atttcatgtt gtctcttcta tttagataca aaattgaagc aattttcacc     1620
aatttaatgc caaaatttaa aacaacgctg tcctgatttc acgatggatg aggataacga     1680
aagggcggtt cctatgtccg ggaaagttcc cgtagaagac aatgagcaaa gctactgaaa     1740
cgcggacacg acgtcgcatt ggtacggata tgagttaaac cgactcaatt cctttattaa     1800
gacataaacc gattttggtt aaagtgtaac agtgagctga tataaaaccg aaacaaaccg     1860
gtacaagttt gattgagcaa cttgatgaca aacttcagaa ttttggttat tgaatgaaaa     1920
tcatagtcta atcgtaaaaa atgtacagaa gaaaagctag agcagaacaa agattctata     1980
ttctggttcc aatttatcat cgctttaacg tccctcagat ttgatcgggc tgcaggaatt     2040
aaacgcccgg gcacgtggga tcctctagag tcgactctag cagatctggc cggcccaccg     2100
gtgggccata tgggcccgcg gccgcgaatt cgagctcggt acctacctgg cgaaaggggg     2160
atgtgctgca aggcgattaa gttgggtaac gccagggttt tcccagtcac gacgttgtaa     2220
aacgacggcc agtgaattgc ggccgcaatt cccgatctag taacatagat gacaccgcgc     2280
gcgataattt atcctagttt gcgcgctata ttttgttttc tatcgcgtat taaatgtata     2340
attgcgggac tctaatcata aaaacccatc tcataaataa cgtcatgcat tacatgttaa     2400
ttattacatg cttaacgtaa ttcaacagaa attatatgat aatcatcgca agaccggcaa     2460
caggattcaa tcttaagaaa ctttattgcc aaatgtttga acgatcgggg aaattcgtcg     2520
agtcaccctc ggccgggctt tttgacgctt aatcggcgt caatacacca cgacgcacct      2580
ggtcacgttc gatggactcg aacagcgcct tgaagttcca ctcgccaaac ccatcgtcgc     2640
ccttgcgctg gatgaattcg aagaacaccg ggcccatcag ggtttccgag aagatctgca     2700
gcagcaggcg tttgtcgcct tccacggaag atccgtccag caggataccg cgtgcctgca     2760
gttgatccac cggctcgccg tggtcaggca ggcggccttc gagcatttcg taataagtgt     2820
ctggcggcgc ggtcatgaag cgcatgccga ttttcttcaa cgcgtcccag gtcttgacca     2880
ggtcgtcggt gaggaacgcc acgtgctgga tgccttcgcc gttgaactgc atcaggaact     2940
```

```
cttcgatctg ccccgcgccc ttggacgact cttcgttcag cgggatgcgg atcatgccgt    3000
ccggcgcact catggccttg gaagtcaggc cggtgtactc gcccttgata tcgaagtaac    3060
gcgcttcacg gaagttgaac aatttctcgt agaagttggc ccagtagacc atgcggccgc    3120
gatagacgtt gtgggtcagg tggtcgatga ctttgagacc tgcaccgacc ggattgcgct    3180
ccacaccttc gaggtacacg aagtcgatgt cgtagatcga gctgccttcg ccgaaacggt    3240
cgatcaggta caacgcgcg ccgccgatgc ccttgatcgc cggcaggttc aattccatcg    3300
gcccggtgtc aatatggatc ggctgggcgc cgagttccag ggcgcggttg taggccttt    3360 gcgagtcctt cacgcggaac gccatgccgc acaccgacgg gccgtgttcg gccgcaaagt    3420
aggaggcgat gctgttgggc tcgttgttga ggatcaggtt gatctcgccc tggcggtaca    3480
ggtgcacgtt cttggaacgg tgggtcgcga ctttggtgaa gcccatgatc tcgaagatcg    3540
gctccagggt acccggcgtc ggcgacgcga attcgatgaa ttcaaagccc atcaggccca    3600
ttgggttttc gtatagatct gccatgcacc ggatccttcc gccgttgctg acgttgccga    3660
ggcttctgga ggagcggcgg gcgacgggga ggctggcggt ggacttgagc ccctggaacg    3720
gagcgacggc ggtggccgac gaggccatca tcacggtggg cgccatagac agcggcggca    3780
ggtacgacag cgtctcgaac ttcttgttgc cgtaggccgg ccacacctgc atatattgaa    3840
ctcttccacc gttgctggga agggtggaga agtcgttagc cttcttggtg gtggggaagg    3900
cggcgttgga cttaaggccg gtgaacggag ccaccatgtt ggcctgagca ggggcggtcc    3960
ggctaacggt cgcgactgag gaggagatcg aagccatggc tatcgttcgt aaatggtgaa    4020
aattttcaga aaattgcttt tgcttttaaaa gaaatgattt aaattgctgc aatagaagta    4080
gaatgcttga ttgcttgaga ttcgtttgtt ttgtatatgt tgtgttgaga attctagagt    4140
cgagagaaat tgatgtctgt agaagaagaa gaacggttaa gagtagattt gggtgagaaa    4200
gatgtgaaat tgttttata ggcaaagacg gagagtctat ttttgagca atcagatcgc    4260 atattaaatc taacggctga gatatcgatc cgtgtgtaca ataaaatgat gtataaaccg    4320
tcgatctgtt ttaatcgacg gttcatatta gtgatccgcg tgatggcagt gatagccact    4380
aagaatcgtc ttttgtttta catgtggcgc cacaaattag ggtaatgaag cggcaatatt    4440
ttggaactcg gaaaataaaa ttgcgccatc acattatttg aaaattttca catgctttta    4500
ttttaaaaac ccacgaatta caagttacaa ccgaaaaaga tttataatat agtgatttat    4560
actaattttg tagtagctta atgtatattg atactggaaa aacaatgaca atcataatcg    4620
atccgtgtgt acaataaaat gatgtataaa ccgtcgatct gttttaatcg acggttcata    4680
ttagtgatcc gcgtgatggc agtgatagcc actaagaatc gtcttttgtt ttacatgtgg    4740
cgccacaaat tagggtaatg aagcggcaat attttggaac tcggaaaata aaattgcgcc    4800
atcacattat ttgaaaattt tcacatgctt ttatttttaaa acccacgaa ttacaagtta    4860 caaccgaaaa agatttataa tatagtgatt tatactaatt ttgtagtagc ttaatgtata    4920
ttgatactgg aaaaacaatg acaatcatat gttagtatta tcaagttatc gtattgatat    4980
tgatattgga acatacaatg ggtattgcct tctttcgacc ataaatatca ccaaatttac    5040
aaagtttgtg tataccaagt tatcaattgt aaatgggatg tcaacatttt aatttccctt    5100
tgagaaacta tagaccacaa gaacacactt caatagataa agtaactatt tacataagag    5160
gttttaaaat cacattaaca aaaataatta ccaaccggca ctcacaaata caaacagagc    5220
acacgacatg tcaaagccac aagtaaattc gttgagtggt ggtttcatta caattgtgtc    5280
acttgcagca caaactatct tgctctggga atcatctcag catcaaagat catgctcact    5340
```

```
tcagggggaac ttagtgtatc catgcctcga ctcatatttc tcctcgacct gcaggcatgc      5400
aagctctaga gcggccgcca ccgcggtgga ggtactcgag tcgcgacgta cgttcgaaca      5460
attggtttta aaagcttgca tgcctgcagg tcgaggagaa atatgagtcg aggcatggat      5520
acactaagtt cccctgaagt gagcatgatc tttgatgctg atgattcc cagagcaaga       5580 tagtttgtgc tgcaagtgac acaattgtaa tgaaaccacc actcaacgaa tttacttgtg      5640
gctttgacat gtcgtgtgct ctgtttgtat ttgtgagtgc cggttggtaa ttattttgt       5700 taatgtgatt ttaaaacctc ttatgtaaat agttacttta tctattgaag tgtgttcttg      5760
tggtctatag tttctcaaag ggaaattaaa atgttgacat cccatttaca attgataact      5820
tggtatacac aaactttgta aatttggtga tatttatggt cgaaagaagg caatacccat      5880
tgtatgttcc aatatcaata tcaatacgat aacttgataa tactaacata tgattgtcat      5940 tgttttttcca gtatcaatat acattaagct actacaaaat tagtataaat cactatatta      6000
taaatctttt tcggttgtaa cttgtaattc gtgggttttt aaaataaaag catgtgaaaa      6060
ttttcaaata atgtgatggc gcaatttat tttccgagtt ccaaaatatt gccgcttcat       6120 tacccctaatt tgtggcgcca catgtaaaac aaaagacgat tcttagtggc tatcactgcc     6180
atcacgcgga tcactaatat gaaccgtcga ttaaaacaga tcgacggttt atacatcatt     6240
ttattgtaca cacggatcga tatctcagcc gttagattta atatgcgatc tgattgctca     6300
aaaaatagac tctccgtctt tgcctataaa acaatttca catctttctc acccaaatct      6360
actcttaacc gttcttcttc ttctacagac atcaatttct ctcgactcta gaggatccaa     6420
gcttatcgat ttcgaacccc tcaggcgaag aacaggtatg atttgtttgt aattagatca     6480
ggggtttagg tcttttccatt acttttaat gttttttctg ttactgtctc cgcgatctga     6540
ttttacgaca atagagtttc gggttttgtc ccattccagt ttgaaaataa aggtccgtct     6600
tttaagtttg ctggatcgat aaacctgtga agattgagtc tagtcgattt attggatgat     6660
ccattcttca tcgtttttttt cttgcttcga agttctgtat aaccagattt gtctgtgtgc     6720
gattgtcatt acctagccgt gtatcgagaa ctagggtttt cgagtcaatt ttgcccccttt     6780 tggttatatc tggttcgata acgattcatc tggattaggg ttttaagtgg tgacgtttag    6840
tattccaatt tcttcaaaat ttagttatgg ataatgaaaa tccccaattg actgttcaat     6900
ttcttgttaa atgcgcagat ccccatggct tcgatctcct cctcagtcgc gaccgttagc     6960
cggaccgccc ctgctcaggc caacatggtg gctccgttca ccggccttaa gtccaacgcc     7020
gccttcccca ccaccaagaa ggctaacgac ttctccaccc ttcccagcaa cggtggaaga     7080
gttcaatgta tgcaggtgtg gccggcctac ggcaacaaga agttcgagac gctgtcgtac     7140
ctgccgccgc tgtctatggc gcccaccgtg atgatggcct cgtcggccac cgccgtcgct     7200
ccgttccagg ggctcaagtc caccgccagc ctccccgtcg cccgccgctc ctccagaagc     7260
ctcggcaacg tcagcaacgg cggaaggatc cggtgcatgg ccggcgccga ggagatcgtg     7320
ctgcagccca tcaaggagat ctccggcacc gtcaagctgc cggggtccaa gtcgctttcc     7380
aaccggatcc tcctactcgc cgccctgtcc gagggggacaa cagtggttga taacctgctg     7440
aacagtgagg atgtccacta catgctcggg gccttgagga ctcttggtct ctctgtcgaa     7500
gcggacaaag ctgccaaaag agctgtagtt gttggctgtg gtggaaagtt cccagttgag     7560
gatgctaaag aggaagtgca gctcttcttg gggaatgctg gaatcgcaat gcggtccttg     7620
acagcagctg ttactgctgc tggtggaaat gcaacttacg tgcttgatgg agtaccaaga     7680
```

```
atgagggaga gacccattgg cgacttggtt gtcggattga agcagcttgg tgcagatgtt    7740
gattgtttcc ttggcactga ctgcccacct gttcgtgtca atggaatcgg agggctacct    7800
ggtggcaagg tcaagctgtc tggctccatc agcagtcagt acttgagtgc cttgctgatg    7860
gctgctcctt tggctcttgg ggatgtggag attgaaatca ttgataaatt aatctccatt    7920
ccgtacgtcg aaatgacatt gagattgatg gagcgttttg gtgtgaaagc agagcattct    7980
gatagctggg acagattcta cattaaggga ggtcaaaaat acaagtcccc taaaaatgcc    8040
tatgttgaag gtgatgcctc aagcgcaagc tatttcttgg ctggtgctgc aattactgga    8100
gggactgtga ctgtggaagg ttgtggcacc accagtttgc agggtgatgt gaagtttgct    8160
gaggtactgg agatgatggg agcgaaggtt acatggaccg agactagcgt aactgttact    8220
ggcccaccgc gggagccatt tggggaggaaa cacctcaagg cgattgatgt caacatgaac    8280
aagatgcctg atgtcgccat gactcttgct gtggttgccc tctttgccga tggcccgaca    8340
gccatcagag acgtggcttc ctggagagta aaggagaccg agaggatggt tgcgatccgg    8400
acggagctaa ccaagctggg agcatctgtt gaggaagggc cggactactg catcatcacg    8460
ccgccggaga agctgaacgt gacggcgatc gacacgtacg acgaccacag gatggcgatg    8520
gctttctccc ttgccgcctg tgccgaggtc cccgtcacca tccgggaccc tgggtgcacc    8580
cggaagacct cccccgacta cttcgatgtg ctgagcactt tcgtcaagaa ttaagctcta    8640
gaactagtgg atccccccgat ccgcgtttgt gttttctggg tttctcactt aagcgtctgc    8700
gttttacttt tgtattgggt ttggcgttta gtagtttgcg gtagcgttct tgttatgtgt    8760
aattacgctt tttcttcttg cttcagcagt ttcggttgaa atataaatcg aatcaagttt    8820
cactttatca gcgttgtttt aaattttggc attaaattgg tgaaaattgc ttcaattttg    8880
tatctaaata gaagagacaa catgaaattc gactttttgac ctcaaatctt cgaacattta    8940
tttcctgatt tcacgatgga tgaggataac gaaagggcgg ttcctatgtc cgggaaagtt    9000
cccgtagaag acaatgagca aagctactga acgcggaca cgacgtcgca ttggtacgga    9060
tatgagttaa accgactcaa ttcctttatt aagacataaa ccgattttgg ttaaagtgta    9120
acagtgagct gatataaaac cgaaacaaac cggtacaagt ttgattgagc aacttgatga    9180
caaacttcag aattttggtt attgaatgaa aatcatagtc taatcgtaaa aatgtacag    9240 aagaaaagct agagcagaac aaagattcta tattctggtt ccaatttatc atcgctttaa    9300
cgtccctcag atttgatcgg gctgcaggaa ttaaacgccc gggcacgtgg gatcctctag    9360
cagatctggc cggcccaccg gtgggccata tgggcccgcg gccgcgaatt cgagctcggt    9420
acctacctgg cgaaaggggg atgtgctgca aggcgattaa gttgggtaac gccagggttt    9480
tcccagtcac gacgttgtaa aacgacggcc agtgaattgc ggccgcaatt cccgatctag    9540
taacatagat gacaccgcgc gcgataattt atcctagttt gcgcgctata ttttgttttc    9600
tatcgcgtat aaatgtata attgcgggac tctaatcata aaacccatc tcataaataa    9660 cgtcatgcat tacatgttaa ttattacatg cttaacgtaa ttcaacagaa attatatgat    9720
aatcatcgca agaccggcaa caggattcaa tcttaagaaa ctttattgcc aaatgtttga    9780
acgatcgggg aaattcgtcg agtcaccctc ggccggcctt tttgacgctt aatcggcggt    9840
caatacacca cgacgcacct ggtcacgttc gatggactcg aacagcgcct tgaagttcca    9900
ctcgccaaac ccatcgtcgc ccttgcgctg gatgaattcg aagaacaccg ggcccatcag    9960
ggtttccgag aagatctgca gcagcaggcg tttgtcgcct tccacggaag atccgtccag   10020
caggataccg cgtgcctgca gttgatccac cggctcgccg tggtcaggca ggcggccttc   10080
```

```
gagcatttcg taataagtgt ctggcggcgc ggtcatgaag cgcatgccga ttttcttcaa    10140
cgcgtcccag gtcttgacca ggtcgtcggt gaggaacgcc acgtgctgga tgccttcgcc    10200
gttgaactgc atcaggaact cttcgatctg ccccgcgccc ttggacgact cttcgttcag    10260
cgggatgcgg atcatgccgt ccggcgcact catggccttg gaagtcaggc cggtgtactc    10320
gcccttgata tcgaagtaac gcgcttcacg gaagttgaac aatttctcgt agaagttggc    10380
ccagtagacc atgcggccgc gatagacgtt gtgggtcagg tggtcgatga ctttgagacc    10440
tgcaccgacc ggattgcgct ccacaccttc gaggtacacg aagtcgatgt cgtagatcga    10500
gctgccttcg ccgaaacggt cgatcaggta aacggcgcg ccgccgatgc ccttgatcgc     10560
cggcaggttc aattccatcg gcccggtgtc aatatggatc ggctgggcgc cgagttccag    10620
ggcgcggttg taggcctttt gcgagtcctt cacgcggaac gccatgccgc acaccgacgg    10680
gccgtgttcg gccgcaaagt aggaggcgat gctgttgggc tcgttgttga ggatcaggtt    10740
gatctcgccc tggcggtaca ggtgcacgtt cttggaacgg tgggtcgcga ctttggtgaa    10800
gcccatgatc tcgaagatcg gctccagggt accggcgtc ggcgacgcga attcgatgaa     10860
ttcaaagccc atcaggccca tgggttttc gtatagatct gccatgcacc ggatccttcc     10920
gccgttgctg acgttgccga ggcttctgga ggagcggcgg gcgacgggga ggctggcggt    10980
ggacttgagc ccctggaacg gagcgacggc ggtggccgac gaggccatca tcacggtggg    11040
cgccatagac agcggcggca ggtacgacag cgtctcgaac ttcttgttgc cgtaggccgg    11100
ccacacctgc atatattgaa ctcttccacc gttgctggga agggtggaga agtcgttagc    11160
cttcttggtg gtggggaagg cggcgttgga cttaaggccg gtgaacggag ccaccatgtt    11220
ggcctgagca gggcggtcc ggctaacggt cgcgactgag gaggagatcg aagccatggc     11280
tatcgttcgt aaatggtgaa aattttcaga aaattgcttt tgctttaaaa gaaatgattt    11340
aaattgctgc aatagaagta gaatgcttga ttgcttgaga ttcgtttgtt ttgtatatgt    11400
tgtgttgaga attctagagt cgagagaaat tgatgtctgt agaagaagaa gaacggttaa    11460
gagtagattt gggtgagaaa gatgtgaaat tgtttttata ggcaaagacg gagagtctat    11520
tttttgagca atcagatcgc atattaaatc taacggctga gatatcgatc cgtgtgtaca    11580
ataaaatgat gtataaaccg tcgatctgtt ttaatcgacg gttcatatta gtgatccgcg    11640
tgatggcagt gatagccact aagaatcgtc ttttgtttta catgtggcgc acaaaattag    11700
ggtaatgaag cggcaatatt ttggaactcg gaaaataaaa ttgcgccatc acattatttg    11760
aaaattttca catgctttta ttttaaaaac ccacgaatta caagttacaa ccgaaaaaga    11820
tttataatat agtgatttat actaattttg tagtagctta atgtatattg atactggaaa    11880
aacaatgaca atcataatcg atccgtgtgt acaataaaat gatgtataaa ccgtcgatct    11940
gttttaatcg acggttcata ttagtgatcc gcgtgatggc agtgatagcc actaagaatc    12000
gtcttttgtt ttacatgtgg cgccacaaat tagggtaatg aagcggcaat attttggaac    12060
tcggaaaata aaattgcgcc atcacattat ttgaaaattt tcacatgctt ttattttaaa    12120
aacccacgaa ttacaagtta caaccgaaaa agatttataa tatagtgatt tatactaatt    12180
ttgtagtagc ttaatgtata ttgatactgg aaaaacaatg acaatcatat gttagtatta    12240
tcaagttatc gtattgatat tgatattgga acatacaatg ggtattgcct tctttcgacc    12300
ataaatatca ccaaatttac aaagtttgtg tataccaagt tatcaattgt aaatgggatg    12360
tcaacatttt aatttccctt tgagaaacta tagaccacag aacacactt caatagataa      12420
```

```
agtaactatt tacataagag gttttaaaat cacattaaca aaaataatta ccaaccggca   12480
ctcacaaata caaacagagc acacgacatg tcaaagccac aagtaaattc gttgagtggt   12540
ggtttcatta caattgtgtc acttgcagca caaactatct tgctctggga atcatctcag   12600
catcaaagat catgctcact tcaggggaac ttagtgtatc catgcctcga ctcatatttc   12660
tcctcgacct gcaggcatgc aagctctaga gcggccgcca ccgcggtgga ggtactcgag   12720
tcgcgacgta cgttcgaaca attggtttta aaagcttgca tgcctgcagg tcgaggagaa   12780
atatgagtcg aggcatggat acactaagtt cccctgaagt gagcatgatc tttgatgctg   12840
agatgattcc cagagcaaga tagtttgtgc tgcaagtgac acaattgtaa tgaaaccacc   12900
actcaacgaa tttacttgtg gctttgacat gtcgtgtgct ctgtttgtat ttgtgagtgc   12960
cggttggtaa ttattttttgt taatgtgatt ttaaaacctc ttatgtaaat agttacttta   13020
tctattgaag tgtgttcttg tggtctatag tttctcaaag ggaaattaaa atgttgacat   13080
cccatttaca attgataact tggtatacac aaactttgta aatttggtga tatttatggt   13140
cgaaagaagg caatacccat tgtatgttcc aatatcaata tcaatacgat aacttgataa   13200
tactaacata tgattgtcat tgttttttcca gtatcaatat acattaagct actacaaaat   13260
tagtataaat cactatatta taaatctttt tcggttgtaa cttgtaattc gtgggttttt   13320
aaaataaaag catgtgaaaa ttttcaaata atgtgatggc gcaattttat tttccgagtt   13380
ccaaaatatt gccgcttcat taccctaatt tgtggcgcca catgtaaaac aaaagacgat   13440
tcttagtggc tatcactgcc atcacgcgga tcactaatat gaaccgtcga ttaaaacaga   13500
tcgacggttt atacatcatt ttattgtaca cacggatcga tatctcagcc gttagattta   13560
atatgcgatc tgattgctca aaaaatagac tctccgtctt tgcctataaa aacaatttca   13620
catctttctc acccaaatct actcttaacc gttcttcttc ttctacagac atcaatttct   13680
ctcgactcta gaggatccaa gcttatcgat ttcgaacccc tcaggcgaag aacaggtatg   13740
atttgtttgt aattagatca ggggtttagg tcttttccatt acttttttaat gttttttctg   13800
ttactgtctc cgcgatctga ttttacgaca atagagtttc gggttttgtc ccattccagt   13860
ttgaaaataa aggtccgtct tttaagtttg ctggatcgat aaacctgtga agattgagtc   13920
tagtcgattt attggatgat ccattcttca tcgttttttt cttgcttcga agttctgtat   13980
aaccagattt gtctgtgtgc gattgtcatt acctagccgt gtatcgagaa ctagggtttt   14040
cgagtcaatt ttgccccttt tggttatatc tggttcgata acgattcatc tggattaggg   14100
ttttaagtgg tgacgtttag tattccaatt tcttcaaaat ttagttatgg ataatgaaaa   14160
tccccaattg actgttcaat ttcttgttaa atgcgcagat ccccatggct tcgatctcct   14220
cctcagtcgc gaccgttagc cggaccgccc ctgctcaggc caacatggtg gctccgttca   14280
ccggccttaa gtccaacgcc gccttcccca ccaccaagaa ggctaacgac ttctccaccc   14340
ttcccagcaa cggtggaaga gttcaatgta tgcaggtgtg gccggcctac ggcaacaaga   14400
agttcgagac gctgtcgtac ctgccgccgc tgtctatggc gcccaccgtg atgatggcct   14460
cgtcggccac cgccgtcgct ccgttccagg ggctcaagtc caccgccagc ctccccgtcg   14520
cccgccgctc ctccagaagc ctcggcaacg tcagcaacgg cggaaggatc cggtgcatgg   14580
ccggcgccga ggagatcgtg ctgcagccca tcaaggagat ctccggcacc gtcaagctgc   14640
cggggtccaa gtcgctttcc aaccggatcc tcctactcgc cgccctgtcc gaggggacaa   14700
cagtggttga taacctgctg aacagtgagg atgtccacta catgctcggg gccttgagga   14760
ctcttggtct ctctgtcgaa gcggacaaag ctgccaaaag agctgtagtt gttggctgtg   14820
```

```
gtggaaagtt cccagttgag gatgctaaag aggaagtgca gctcttcttg gggaatgctg    14880
gaatcgcaat gcggtccttg acagcagctg ttactgctgc tggtggaaat gcaacttacg    14940
tgcttgatgg agtaccaaga atgagggaga gacccattgg cgacttggtt gtcggattga    15000
agcagcttgg tgcagatgtt gattgtttcc ttggcactga ctgcccacct gttcgtgtca    15060
atggaatcgg agggctacct ggtggcaagg tcaagctgtc tggctccatc agcagtcagt    15120
acttgagtgc cttgctgatg gctgctcctt ggctcttgg ggatgtggag attgaaatca    15180
ttgataaatt aatctccatt ccgtacgtcg aaatgacatt gagattgatg gagcgttttg    15240
gtgtgaaagc agagcattct gatagctggg acagattcta cattaaggga ggtcaaaaat    15300
acaagtcccc taaaaatgcc tatgttgaag gtgatgcctc aagcgcaagc tatttcttgg    15360
ctggtgctgc aattactgga gggactgtga ctgtggaagg ttgtggcacc accagtttgc    15420
agggtgatgt gaagtttgct gaggtactgg agatgatggg agcgaaggtt acatggaccg    15480
agactagcgt aactgttact ggcccaccgc gggagccatt tgggaggaaa cacctcaagg    15540
cgattgatgt caacatgaac aagatgcctg atgtcgccat gactcttgct gtggttgccc    15600
tctttgccga tggcccgaca gccatcagag acgtggcttc ctggagagta aaggagaccg    15660
agaggatggt tgcgatccgg acggagctaa ccaagctggg agcatctgtt gaggaagggc    15720
cggactactg catcatcacg ccgcggaga agctgaacgt gacggcgatc gacacgtacg    15780
acgaccacag gatggcgatg gctttctccc ttgccgcctg tgccgaggtc cccgtcacca    15840
tccgggaccc tgggtgcacc cggaagacct tccccgacta cttcgatgtg ctgagcactt    15900
tcgtcaagaa ttaagctcta gaactagtgg atcccccgat ccgcgtttgt gttttctggg    15960
tttctcactt aagcgtctgc gttttacttt tgtattgggt ttggcgttta gtagtttgcg    16020
gtagcgttct tgttatgtgt aattacgctt tttcttcttg cttcagcagt ttcggttgaa    16080
atataaatcg aatcaagttt cactttatca gcgttgtttt aaattttggc attaaattgg    16140
tgaaaattgc ttcaattttg tatctaaata gaagagacaa catgaaattc gacttttgac    16200
ctcaaatctt cgaacattta tttcctgatt tcacgatgga tgaggataac gaaagggcgg    16260
ttcctatgtc cgggaaagtt cccgtagaag acaatgagca aagctactga aacgcggaca    16320
cgacgtcgca ttggtacgga tatgagttaa accgactcaa ttcctttatt aagacataaa    16380 ccgatttttgg ttaaagtgta acagtgagct gatataaaac cgaaacaaac cggtacaagt    16440
ttgattgagc aacttgatga caaacttcag aattttggtt attgaatgaa atcatagtc     16500 taatcgtaaa aaatgtacag aagaaaagct agagcagaac aaagattcta tattctggtt    16560
ccaatttatc atcgctttaa cgtccctcag atttgatcgg gctgcaggaa ttaatgtggt    16620
tcatccgtct ttttgttaat gcggtcatca atacgtgcct caaagattgc caaatagatt    16680
aatgtggttc atctccctat atgttttgct tgttggattt tgctatcaca tgtttattgc    16740
tccaaactaa ttataataaa atgactttca aatgattggt gttgacattc ttttcaaatt    16800
gttcgctgaa gaaaagataa tctcgaggcc ttgatttgtt aatgctttca ttaataaata    16860
aataaaataa ctcttttccaa atttcaattc atgcttttat attgtgtggt tcatcctcat    16920
cttatgtcac tattatcatt tcatgtttga gactttactt ggccatattt gagaagacct    16980
tcttcattat aggcaatttt atctccacaa taatataaga gaatatcttg aattaataat    17040
tattgaggat atattatagg gttctatgtg gaactaaaga catggttacc ccattaagag    17100
agagtataga ggaattactt ttatttgcca cgaggcgacg cgacttgtat ttattttgga    17160
```

```
attgtacttt tgcgtgagca gtgtggctct atgttggggc ctccacttgt tggtgtttta  17220
tatatgtgaa aggaggatga gggtgatggt tcatttcttt gcattatttt tgttattcgc  17280
gcgaatgata tatgccctgt ttttgaagat tgatagggaa gtccatatat aggaattgaa  17340
gtgtcaaaag ggtgtgagta tgtgctatga taatcaccca attaatgtac atctggtgtg  17400
gtgtttgaat ttgtaggtca ttaattaata ttcctcttgg tgaagtttgg agttcttttg  17460
caattacaat tctgttttgt aagtgattat gatggacttt tagatgtttc tcaaacagta  17520
ggtgtaaaga aaaatgggcc ctggtatgaa aatttgtttt cactctttct cattcatatc  17580
tttaaaaaaa gaatgataat tttgtaataa aaataaaaaa atattaaata ttttctcaaa  17640
tcaaacaacc tttatttttt atgccaacaa taattttgtt aaagatggag atttcaatta  17700
ttatataaga gttcattata gttgaaaatt gaatgaatgt atatgtttac gttttttgtc  17760
tcaagtgaaa ctaagatcaa atattcatat ctattgagct ggtctt            17806
```

<210> SEQ ID NO 12
<211> LENGTH: 23
<212> TYPE: DNA
<213> ORGANISM: Artificial Sequence
<220> FEATURE:
<223> OTHER INFORMATION: primer SHA130

<400> SEQUENCE: 12
ctatattctg gttccaattt atc                                              23

<210> SEQ ID NO 13
<211> LENGTH: 20
<212> TYPE: DNA
<213> ORGANISM: Artificial Sequence
<220> FEATURE:
<223> OTHER INFORMATION: primer SMP178

<400> SEQUENCE: 13
tgaggcacgt attgatgacc                                                  20

The invention claimed is:

1. A method for identifying elite event EE-GM3 in biological samples, which method comprises detection of an EE-GM3 specific region with a specific primer pair or probe which specifically recognizes the 5' or 3' flanking region of foreign DNA comprising herbicide tolerance genes in EE-GM3 and the inserted foreign DNA contiguous therewith; reference seed comprising elite event EE-GM3 having been deposited at the NCIMB under deposit number NCIMB 41659.

2. The method of claim 1, said method comprising amplifying a DNA fragment of between 50 and 1000 bp from a nucleic acid present in said biological samples using a polymerase chain reaction with at least two primers, one of said primers recognizing the 5' flanking region of foreign DNA comprising herbicide tolerance genes in EE-GM3, said 5' flanking region comprising the nucleotide sequence of SEQ ID No. 2 from nucleotide 1 to nucleotide 1451 or the 3' flanking region of foreign DNA comprising herbicide tolerance genes in EE-GM3, said 3' flanking region comprising the nucleotide sequence of the complement of SEQ ID No. 3 from nucleotide 241 to nucleotide 1408, the other primer of said primers recognizing a sequence within the foreign DNA comprising the nucleotide sequence of the complement of SEQ ID No. 2 from nucleotide 1452 to nucleotide 1843 or the nucleotide sequence of SEQ ID No. 3 from nucleotide 1 to nucleotide 240 or the other primer of said primers recognizing a sequence within the foreign DNA comprising the nucleotide sequence of SEQ ID No. 1 or its complement, or comprising the nucleotide sequence of SEQ ID No. 11 from nucleotide position 1452 to nucleotide position 16638 or its complement.

3. The method of claim 2, wherein said primer recognizing the 5' flanking region comprises a nucleotide sequence of 17 to 200 consecutive nucleotides selected from the nucleotide sequence of SEQ ID No. 2 from nucleotide 1 to nucleotide 1451 or said primer recognizing the 3' flanking region of EE-GM3 comprises a nucleotide sequence of 17 to 200 consecutive nucleotides selected from the nucleotide sequence of the complement of SEQ ID No. 3 from nucleotide 241 to nucleotide 1408, and said primer recognizing a sequence within the foreign DNA comprises 17 to 200 consecutive nucleotides selected from the nucleotide sequence of the complement of SEQ ID No. 2 from nucleotide 1452 to nucleotide 1843 or the nucleotide sequence of SEQ ID No. 3 from nucleotide 1 to nucleotide 240, or the nucleotide sequence of SEQ ID No. 1 or its complement, or the nucleotide sequence of SEQ ID No. 11 from nucleotide position 1452 to nucleotide position 16638 or its complement.

4. The method of claim 2, wherein said primer recognizing the 5' flanking region comprises at its extreme 3' end a nucleotide sequence of at least 17 consecutive nucleotides selected from the nucleotide sequence of SEQ ID No. 2 from nucleotide 1 to nucleotide 1451 or said primer recognizing the 3' flanking region of EE-GM3 comprises at its extreme 3' end a nucleotide sequence of at least 17 consecutive nucleotides selected from the nucleotide sequence of the complement of SEQ ID No. 3 from nucleotide 241 to nucleotide 1408, and said primer recognizing a sequence within the foreign DNA comprises at its 3' end at least 17 consecutive nucleotides selected from the nucleotide sequence of the complement of SEQ ID No. 2 from nucleotide 1452 to nucleotide 1843 or the nucleotide sequence of SEQ ID No. 3 from nucleotide 1 to nucleotide 240 or the nucleotide sequence of SEQ ID No. 1 or its complement, or the nucleotide sequence of SEQ ID No. 11 from nucleotide position 1452 to nucleotide position 16638 or its complement.

5. The method of claim 4, wherein said primers comprise the sequence of SEQ ID No. 5 and SEQ ID No. 4, respectively, or the sequence of SEQ ID No. 5 and SEQ ID No. 7 respectively.

6. The method of claim 5, which method comprises amplifying a fragment of about 263 or 706 bp using the EE-GM3 PCR identification protocol.

7. A kit comprising one primer recognizing the 5' flanking region of foreign DNA comprising herbicide tolerance genes in EE-GM3, said 5' flanking region comprising the nucleotide sequence of SEQ ID No. 2 from nucleotide 1 to nucleotide 1451 or one primer recognizing the 3' flanking region of foreign DNA comprising herbicide tolerance genes in EE-GM3, said 3' flanking region comprising the nucleotide sequence of the complement of SEQ ID No. 3 from nucleotide 241 to nucleotide 1408, and one primer recognizing a sequence within the foreign DNA, said foreign DNA comprising the nucleotide sequence of the complement of SEQ ID No. 2 from nucleotide 1452 to nucleotide 1843 or the nucleotide sequence of SEQ ID No. 3 from nucleotide 1 to nucleotide 240 or the nucleotide sequence of SEQ ID No. 1 or its complement, or the nucleotide sequence of SEQ ID No. 11 from nucleotide position 1452 to nucleotide position 16638 or its complement, wherein
  at least one of said primers is labeled;
  the 5' end of at least one of said primers comprises one or more mismatches or a nucleotide sequence unrelated to the 5' or 3' flanking sequence of foreign DNA sequence;
  at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3; or
  at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

8. The kit of claim 7, wherein said primer recognizing the 5' flanking region comprises a nucleotide sequence of 17 to 200 consecutive nucleotides selected from the nucleotide sequence of SEQ ID No. 2 from nucleotide 1 to nucleotide 1451 or said primer recognizing the 3' flanking region of EE-GM3 comprises a nucleotide sequence of 17 to 200 consecutive nucleotides selected from the nucleotide sequence of the complement of SEQ ID No. 3 from nucleotide 241 to nucleotide 1408, and said primer recognizing a sequence within the foreign DNA comprises 17 to 200 consecutive nucleotides selected from the nucleotide sequence of the complement of SEQ ID No. 2 from nucleotide 1452 to nucleotide 1843 or the nucleotide sequence of SEQ ID No. 3 from nucleotide 1 to nucleotide 240, or the nucleotide sequence of SEQ ID No. 1 or its complement, or the nucleotide sequence of SEQ ID No. 11 from nucleotide position 1452 to nucleotide position 16638 or its complement.

9. The kit of claim 7, wherein said primer recognizing the 5' flanking region comprises at its extreme 3' end a nucleotide sequence of at least 17 consecutive nucleotides selected from the nucleotide sequence of SEQ ID No. 2 from nucleotide 1 to nucleotide 1451 or said primer recognizing the 3' flanking region of EE-GM3 comprises at its extreme 3' end a nucleotide sequence of at least 17 consecutive nucleotides selected from the nucleotide sequence of the complement of SEQ ID No. 3 from nucleotide 241 to nucleotide 1408, and said primer recognizing a sequence within the foreign DNA comprises at its 3' end at least 17 consecutive nucleotides selected from the nucleotide sequence of the complement of SEQ ID No. 2 from nucleotide 1452 to nucleotide 1843 or the nucleotide sequence of SEQ ID No. 3 from nucleotide 1 to nucleotide 240, or the nucleotide sequence of SEQ ID No. 1 or its complement, or the nucleotide sequence of SEQ ID No. 11 from nucleotide position 1452 to nucleotide position 16638 or its complement.

10. The kit of claim 7, comprising a primer comprising the sequence of SEQ ID No. 4 and a primer comprising the sequence of SEQ ID No. 5 or comprising a primer comprising the sequence of SEQ ID No. 5 and a primer comprising the sequence of SEQ ID No. 7.

11. A pair of primers suitable for use in an EE-GM3 specific detection, comprising a first primer which, under optimized detection conditions specifically recognizes a sequence within the 5' or 3' flanking region of foreign DNA comprising herbicide tolerance genes in EE-GM3, said 5' flanking region comprising the nucleotide sequence of SEQ ID No. 2 from nucleotide 1 to nucleotide 1451 and said 3' flanking region comprising the nucleotide sequence of the complement of SEQ ID No. 3 from nucleotide 241 to nucleotide 1408, and a second primer recognizing a sequence within the foreign DNA contiguous with said 5' or 3' flanking region in EE-GM3, said foreign DNA comprising the nucleotide sequence of the complement of SEQ ID No. 2 from nucleotide 1452 to nucleotide 1843 or the nucleotide sequence of SEQ ID No. 3 from nucleotide 1 to nucleotide 240 or the nucleotide sequence of SEQ ID No. 1 or its complement, or the nucleotide sequence of SEQ ID No. 11 from nucleotide position 1452 to nucleotide position 16638 or its complement, wherein
  at least one of said primers is labeled;
  the 5' end of at least one of said primers comprises one or more mismatches or a nucleotide sequence unrelated to the 5' or 3' flanking sequence of foreign DNA sequence;
  at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3; or at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

12. The primer pair of claim 11, wherein said first primer comprises a nucleotide sequence of 17 to 200 consecutive nucleotides selected from the nucleotide sequence of the complement of SEQ ID No. 3 from nucleotide 241 to nucleotide 1408, and said second primer comprises a nucleotide sequence of 17 to 200 consecutive nucleotides selected from the nucleotide sequence of SEQ ID No. 3 from nucleotide 1 to nucleotide 240.

13. The primer pair of claim 11, wherein said first primer comprises at its extreme 3' end a nucleotide sequence of at least 17 consecutive nucleotides selected from the nucleotide sequence of SEQ ID No. 2 from nucleotide 1 to nucleotide 1451 or a nucleotide sequence of at least 17 consecutive nucleotides selected from the nucleotide sequence of the complement of SEQ ID No. 3 from nucleotide 241 to nucleotide 1408.

14. The primer pair of claim 11, wherein said first primer comprises at its extreme 3' end the sequence of SEQ ID No. 5.

15. A primer pair comprising a first primer comprising at its extreme 3' end the sequence of SEQ ID No. 5 and a second primer comprising at its extreme 3' end the sequence of SEQ ID No. 4, wherein at least one of said primers is labeled;

the 5' end of at least one of said primers comprises one or more mismatches or a nucleotide sequence unrelated to the 5' or 3' flanking sequence of foreign DNA sequence;

at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3; or at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

16. The method of claim 1, which method comprises hybridizing a nucleic acid of biological samples with a specific probe for EE-GM3.

17. The method of claim 16, wherein the sequence of said specific probe has at least 80% sequence identity with a sequence comprising part of the 5' flanking sequence or the 3' flanking sequence of EE-GM3 and the sequence of the foreign DNA contiguous therewith.

18. The method of claim 17, wherein the sequence of said specific probe has at least 80% sequence identity with SEQ ID No. 2 from nucleotide 1431 to 1472 or SEQ ID No. 3 from nucleotide 220 to 261, or the complement of said sequences.

19. A kit comprising a specific probe, capable of hybridizing specifically to a specific region of EE-GM3, wherein the sequence of said specific probe has at least 80% sequence identity with a sequence comprising part of the 5' flanking sequence or the 3' flanking sequence of foreign DNA comprising herbicide tolerance genes in EE-GM3 and the sequence of the foreign DNA contiguous therewith; reference seed comprising elite event EE-GM3 having been deposited at the NCIMB under deposit number NCIMB 41659.

20. The kit of claim 19, wherein the sequence of said specific probe comprises a nucleotide sequence having at least 80% sequence identity with SEQ ID No. 2 from nucleotide 1441 to 1462 or SEQ ID No. 3 from nucleotide 230 to 251, or the complement of said sequences.

21. A specific probe for the identification of elite event EE-GM3 in biological samples, which comprises a nucleotide sequence having at least 80% sequence identity with a sequence comprising part of the 5' flanking sequence or the 3' flanking sequence of foreign DNA comprising herbicide tolerance genes in EE-GM3 and the sequence of the foreign DNA contiguous therewith, or the complement thereof; reference seed comprising elite event EE-GM3 having been deposited at the NCIMB under deposit number NCIMB 41659.

22. The probe of claim 21 which has at least 80% sequence identity with SEQ ID No. 2 from nucleotide 1441 to 1462 or SEQ ID No. 3 from nucleotide 230 to 251, or the complement of said sequences.

23. A specific probe comprising the nucleotide sequence of SEQ ID No. 2 from nucleotide 1441 to 1462 or SEQ ID No. 3 from nucleotide 230 to 251, or the complement of said sequences.

24. A method for confirming seed purity, which method comprises detection of an EE-GM3 specific region with a specific primer or probe which specifically recognizes the 5' or 3' flanking region of foreign DNA comprising herbicide tolerance genes in EE-GM3 and the inserted, foreign DNA contiguous therewith, in seed samples; reference seed comprising elite event EE-GM3 having been deposited at the NCIMB under deposit number NCIMB 41659.

25. A method for screening seeds for the presence of EE-GM3, which method comprises detection of an EE-GM3 specific region with a specific primer or probe which specifically recognizes the 5' or 3' flanking region of foreign DNA comprising herbicide tolerance genes in EE-GM3 and the inserted, foreign DNA contiguous therewith, in samples of seed lots; reference seed comprising elite event EE-GM3 having been deposited at the NCIMB under deposit number NCIMB 41659.

26. A method of detecting the presence of elite event EE-GM3 in biological samples through hybridization with a substantially complementary labeled nucleic acid probe in which the probe:target nucleic acid ratio is amplified through recycling of the target nucleic acid sequence, said method comprising:

a) hybridizing said target nucleic acid sequence to a first nucleic acid oligonucleotide comprising the nucleotide sequence of SEQ ID No. 2 from nucleotide 1452 to nucleotide 1469 or its complement or said first nucleic acid oligonucleotide comprising the nucleotide sequence of SEQ ID No. 3 from nucleotide 223 to nucleotide 240 or its complement;

b) hybridizing said target nucleic acid sequence to a second nucleic acid oligonucleotide comprising the nucleotide sequence of SEQ ID No. 2 from nucleotide 1434 to nucleotide 1451 or its complement or said labeled nucleic acid probe comprising the nucleotide sequence of SEQ ID No. 3 from nucleotide 241 to nucleotide 258 or its complement, wherein said first and second oligonucleotide overlap by at least one nucleotide and wherein either said first or said second oligonucleotide is labeled to be said labeled nucleic acid probe;

c) cleaving only the labeled probe within the probe:target nucleic acid sequence duplex with an enzyme which causes selective probe cleavage resulting in duplex disassociation, leaving the target sequence intact;

d) recycling of the target nucleic acid sequence by repeating steps (a) to (c); and e) detecting cleaved labeled probe, thereby determining the presence of said target nucleic acid sequence.

27. The kit of claim 7, wherein at least one of said primers is labeled.

28. The kit of claim 8, wherein at least one of said primers is labeled.

29. The kit of claim 9, wherein at least one of said primers is labeled.

30. The kit of claim 10, wherein at least one of said primers is labeled.

31. The primer pair of claim 11, wherein at least one of said primers is labeled.

32. The primer pair of claim 12, wherein at least one of said primers is labeled.

33. The primer pair of claim 13, wherein at least one of said primers is labeled.

34. The primer pair of claim 14, wherein at least one of said primers is labeled.

35. The primer pair of claim 15, wherein at least one of said primers is labeled.

36. The kit of claim 7, wherein the 5' end of at least one of said primers comprises one or more mismatches or a nucleotide sequence unrelated to the 5' or 3' flanking sequence of foreign DNA sequence.

37. The kit of claim 8, wherein the 5' end of at least one of said primers comprises one or more mismatches or a nucleotide sequence unrelated to the 5' or 3' flanking sequence of foreign DNA sequence.

38. The kit of claim 9, wherein the 5' end of at least one of said primers comprises one or more mismatches or a nucleotide sequence unrelated to the 5' or 3' flanking sequence of foreign DNA sequence.

39. The kit of claim 10, wherein the 5' end of at least one of said primers comprises one or more mismatches or a nucleotide sequence unrelated to the 5' or 3' flanking sequence of foreign DNA sequence.

40. The primer pair of claim 11, wherein the 5' end of at least one of said primers comprises one or more mismatches or a nucleotide sequence unrelated to the 5' or 3' flanking sequence of foreign DNA sequence.

41. The primer pair of claim 12, wherein the 5' end of at least one of said primers comprises one or more mismatches or a nucleotide sequence unrelated to the 5' or 3' flanking sequence of foreign DNA sequence.

42. The primer pair of claim 13, wherein the 5' end of at least one of said primers comprises one or more mismatches or a nucleotide sequence unrelated to the 5' or 3' flanking sequence of foreign DNA sequence.

43. The primer pair of claim 14, wherein the 5' end of at least one of said primers comprises one or more mismatches or a nucleotide sequence unrelated to the 5' or 3' flanking sequence of foreign DNA sequence.

44. The primer pair of claim 15, wherein the 5' end of at least one of said primers comprises one or more mismatches or a nucleotide sequence unrelated to the 5' or 3' flanking sequence of foreign DNA sequence.

45. The kit of claim 7, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

46. The kit of claim 8, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

47. The kit of claim 9, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

48. The kit of claim 10, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

49. The primer pair of claim 11, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

50. The primer pair of claim 12, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

51. The primer pair of claim 13, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

52. The primer pair of claim 14, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

53. The primer pair of claim 15, wherein at least one of said primers comprises a nucleotide sequence at their 3' end spanning the joining region between the plant DNA derived sequences and the foreign DNA sequences, said joining region being at nucleotides 1451-1452 in SEQ ID No 2 or nucleotides 240-241 in SEQ ID No 3, provided that the 17 consecutive nucleotides at the 3' end are not derived exclusively from either the foreign DNA or plant-derived sequences in SEQ ID Nos. 2 or 3.

54. The kit of claim 7, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

55. The kit of claim 8, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

56. The kit of claim 9, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

57. The kit of claim 10, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

58. The primer pair of claim 11, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

59. The primer pair of claim 12, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

60. The primer pair of claim 13, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

61. The primer pair of claim 14, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

62. The primer pair of claim 15, wherein at least one of said primers comprises a sequence which is between 80 and 100% identical to a sequence within the 5' or 3' flanking region of the elite event or the foreign DNA of the elite event, respectively, and said primer sequence comprises at least one mismatch with said 5' or 3' flanking region or said foreign DNA, provided the at least one mismatch still allows specific identification of the elite event with these primers under optimized PCR conditions.

* * * * *